(12) United States Patent
Kawaue et al.

(10) Patent No.: US 8,338,076 B2
(45) Date of Patent: Dec. 25, 2012

(54) RESIST COMPOSITION, METHOD OF FORMING RESIST PATTERN, NOVEL COMPOUND, AND ACID GENERATOR

(75) Inventors: Akiya Kawaue, Kawasaki (JP); Yoshiyuki Utsumi, Kawasaki (JP); Hideo Hada, Kawasaki (JP); Takehiro Seshimo, Kawasaki (JP); Kensuke Matsuzawa, Kawasaki (JP); Keita Ishiduka, Kawasaki (JP); Kotaro Endo, Kawasaki (JP)

(73) Assignee: Tokyo Ohka Kogyo Co., Ltd., Kanagawa-ken (JP)

( * ) Notice: Subject to any disclaimer, the term of this patent is extended or adjusted under 35 U.S.C. 154(b) by 264 days.

(21) Appl. No.: 12/591,639

(22) Filed: Nov. 25, 2009

(65) Prior Publication Data

US 2010/0136478 A1    Jun. 3, 2010

(30) Foreign Application Priority Data

Nov. 28, 2008 (JP) ................ P2008-304398
Sep. 18, 2009 (JP) ................ P2009-217673

(51) Int. Cl.
- *G03F 7/004* (2006.01)
- *G03F 7/028* (2006.01)
- *G03F 7/039* (2006.01)
- *G03F 7/26* (2006.01)
- *C07C 381/12* (2006.01)

(52) U.S. Cl. ............. 430/270.1; 430/326; 430/921; 430/923; 568/28; 568/31; 568/33; 568/75; 568/77

(58) Field of Classification Search ........... 430/270.1, 430/326, 322, 921, 922, 923, 924; 568/28, 568/31, 33, 75, 77

See application file for complete search history.

(56) References Cited

U.S. PATENT DOCUMENTS

| | | | |
|---|---|---|---|
| 5,945,517 A | 8/1999 | Nitta et al. | |
| 6,153,733 A | 11/2000 | Yukawa et al. | |
| 6,949,325 B2 | 9/2005 | Li et al. | |
| 7,074,543 B2 | 7/2006 | Iwai et al. | |
| 2001/0049073 A1 | 12/2001 | Hada et al. | |
| 2006/0241200 A1* | 10/2006 | Herilhy et al. | 522/50 |
| 2007/0148592 A1* | 6/2007 | Wada et al. | 430/270.1 |
| 2008/0311522 A1 | 12/2008 | Iwai et al. | |
| 2009/0075204 A1 | 3/2009 | Takeshita et al. | |
| 2009/0087786 A1 | 4/2009 | Hatakeyama | |
| 2010/0015552 A1 | 1/2010 | Kawaue et al. | |
| 2010/0015555 A1* | 1/2010 | Utsumi et al. | 430/286.1 |
| 2011/0008728 A1* | 1/2011 | Nakamura et al. | 430/270.1 |
| 2012/0009521 A1 | 1/2012 | Kawaue et al. | |

FOREIGN PATENT DOCUMENTS

| | | |
|---|---|---|
| JP | 8-157451 | 6/1996 |
| JP | 09-208554 | 8/1997 |
| JP | 11-035551 | 2/1999 |
| JP | 11-035552 | 2/1999 |
| JP | 11-035573 | 2/1999 |
| JP | 11-322707 | 11/1999 |
| JP | 2000-206694 | 7/2000 |
| JP | 2001-255647 | 9/2001 |
| JP | 2003-241385 | 8/2003 |
| JP | 2005-037888 | 2/2005 |
| JP | 2005-336452 | 12/2005 |
| JP | 2006-259582 | 9/2006 |
| JP | 2006-317803 | 11/2006 |
| JP | 2008-3540 | 1/2008 |
| JP | 2008-107377 | 5/2008 |
| JP | 2009-019028 | 1/2009 |
| JP | 2009-515944 | 4/2009 |
| WO | 2004/074242 A2 | 9/2004 |

OTHER PUBLICATIONS

Gil et al., "First Microprocessors with Immersion Lithography", Proceedings of SPIE, vol. 5754, pp. 119-128, 2005.
Ebihara et al., "Beyond $K_1$=0.25 lithography: 70nm L/S patterning using KrF scanners", Proceedings of SPIE, vol. 5256, pp. 958-994, 2003.
Borodovsky, "Marching to the beat of Moore's Law", Proceedings of SPIE, vol. 6153, pp. 615301-1 to 615301-19, 2006.
Office Action issued Apr. 10, 2012 in U.S. Appl. No. 12/788,160.

* cited by examiner

*Primary Examiner* — Anca Eoff
(74) *Attorney, Agent, or Firm* — Wenderoth, Lind & Ponack, L.L.P.

(57) ABSTRACT

A resist composition including a base component (A) which exhibits changed solubility in an alkali developing solution under action of acid and an acid-generator component (B) which generates acid upon exposure, the acid-generator component (B) including an acid generator (B1) containing a compound having a cation moiety comprising a group represented by general formula (I) (in the formula, $R^5$ represents an organic group having a carbonyl group, an ester bond or a sulfonyl group; and Q represents a divalent linking group).

[Chemical Formula 1]

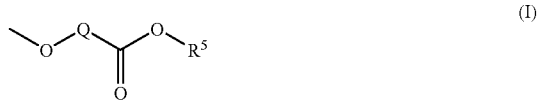

(I)

24 Claims, 1 Drawing Sheet

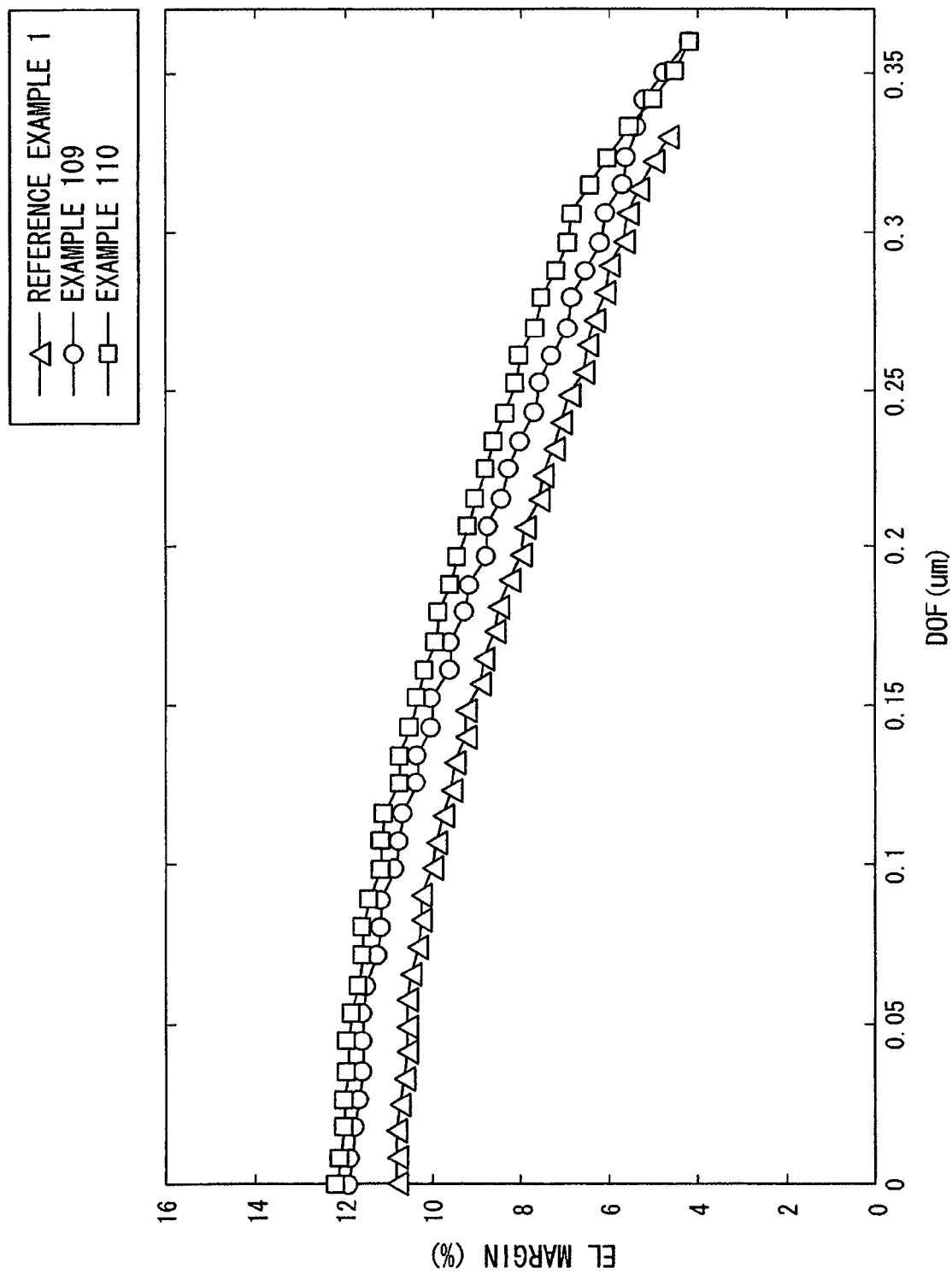

RESIST COMPOSITION, METHOD OF FORMING RESIST PATTERN, NOVEL COMPOUND, AND ACID GENERATOR

TECHNICAL FIELD

The present invention relates to a resist composition, a method of forming a resist pattern using the same, a novel compound useful as an acid generator for a resist composition, and an acid generator.

Priority is claimed on Japanese Patent Application No. 2008-304398, filed Nov. 28, 2008, and Japanese Patent Application No. 2009-217673, filed Sep. 18, 2009, the contents of which are incorporated herein by reference.

BACKGROUND ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film. A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are starting to be introduced in mass production. Furthermore, research is also being conducted into lithography techniques that use an exposure light source having a wavelength shorter than these excimer lasers, such as $F_2$ excimer lasers, electron beam, extreme ultraviolet radiation (EUV), and X-ray.

Resist materials for use with these types of exposure light sources require lithography properties such as a high resolution capable of reproducing patterns of minute dimensions, and a high level of sensitivity to these types of exposure light sources. As a resist material which satisfies these conditions, a chemically amplified resist is used, which includes a base resin that exhibits a changed solubility in an alkali developing solution under action of acid and an acid generator that generates acid upon exposure. For example, a chemically amplified positive resist contains, as a base resin, a resin which exhibits increased solubility in an alkali developing solution under action of acid, and an acid generator. In the formation of a resist pattern, when acid is generated from the acid generator upon exposure, the exposed portions become soluble in an alkali developing solution.

Until recently, polyhydroxystyrene (PHS) or derivative resins thereof in which the hydroxyl groups are protected with acid-dissociable, dissolution-inhibiting groups (PHS-based resins), which exhibit high transparency to a KrF excimer laser (248 nm), have been used as the base resin component of chemically amplified resists. However, because PHS-based resins contain aromatic rings such as benzene rings, their transparency is inadequate for light with wavelengths shorter than 248 nm, such as light of 193 nm. Accordingly, chemically amplified resists that use a PHS-based resin as the base resin component suffer from low levels of resolution in processes that use light of 193 nm. As a result, resins that contain structural units derived from (meth)acrylate esters within the main chain (acrylic resins) are now widely used as base resins for resists that use ArF excimer laser lithography, as they exhibit excellent transparency in the vicinity of 193 nm. In the case of a positive resist, as the base resin, those which have a structural unit derived from (meth)acrylate ester including an aliphatic polycyclic group-containing, tertiary alkyl ester-type acid dissociable, dissolution inhibiting group, such as a structural unit derived from 2-alkyl-2-adamantyl (meth)acrylate are mainly used (for example, see Patent Document 1).

Here, the term "(meth)acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position. The term "(meth)acrylic acid" is a generic term that includes either or both of acrylic acid having a hydrogen atom bonded to the α-position and methacrylic acid having a methyl group bonded to the α-position.

On the other hand, as acid generators usable in a chemically amplified resist, various types have been proposed including, for example, onium salt acid generators such as iodonium salts and sulfonium salts; oxime sulfonate acid generators; diazomethane acid generators; nitrobenzylsulfonate acid generators; iminosulfonate acid generators; and disulfone acid generators.

Currently, as acid generators, onium salt acid generators having an onium ion such as triphenylsulfonium as the cation moiety are used (for example, see Patent Document 2).

DOCUMENTS OF RELATED ART

Patent Document

[Patent Document 1] Japanese Unexamined Patent Application, First Publication No. 2003-241385
[Patent Document 2] Japanese Unexamined Patent Application, First Publication No. 2005-037888

SUMMARY OF THE INVENTION

In recent years, as requirements for high resolution increase with progress in the miniaturization of resist patterns, further improvement in various lithography properties has been demanded. Further, development of a novel resist material has been demanded.

In the aforementioned onium salt-based acid generator having a cation such as triphenylsulfonium, the cation exhibits a relatively high hydrophobicity, and the acid generator exhibits excellent affinity for the base component of a resist composition and an excellent solubility in an organic solvent. Therefore, it is presumed that such an acid generator contributes to improvement in various lithography properties.

However, as the hydrophobicity of the cation becomes higher, the solubility of the acid generator in an alkali developing solution tends to become poor. When the solubility of the acid generator in an alkali developing solution becomes poor, the acid generator cannot be satisfactorily dissolved during development. As a result, it becomes highly possible that defects are generated and lithography properties are deteriorated. Further, it becomes difficult to obtain a resist pattern with a high rectangularity, for example, the formed pattern is likely to have a rounded top portion.

The term "defects" refers to general abnormalities within a resist film that are detected when observed from directly above the developed resist pattern using, for example, a surface defect detection apparatus (product name: "KLA") manufactured by KLA-TENCOR Corporation. Examples of these abnormalities include post-developing scum, foam, dust, bridges formed between resist patterns, and color irregularities.

Therefore, there is a demand for a compound useful as an acid generator for a resist composition, which can achieve excellent solubility in a developing solution, excellent lithography properties and an excellent resist pattern shape.

The present invention takes the above circumstances into consideration, with an object of providing a novel compound useful as an acid generator for a resist composition, an acid generator including the compound, a resist composition containing the acid generator, and a method of forming a resist pattern using the resist composition.

For solving the above-mentioned problems, the present invention employs the following aspects.

Specifically, a first aspect of the present invention is a resist composition including a base component (A) which exhibits changed solubility in an alkali developing solution under action of acid and an acid-generator component (B) which generates acid upon exposure, the acid-generator component (B) including an acid generator (B1) containing a compound having a cation moiety comprising a group represented by general formula (I) shown below.

[Chemical Formula 1]

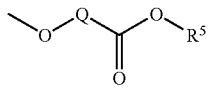

(I)

In formula (I), $R^5$ represents an organic group having a carbonyl group, an ester bond or a sulfonyl group; and Q represents a divalent linking group.

A second aspect of the present invention is a method of forming a resist pattern, including forming a resist film on a substrate using a resist composition according to the first aspect, subjecting the resist film to exposure, and subjecting the resist film to alkali developing to form a resist pattern.

A third aspect of the present invention is a compound represented by general formula (b1-11) shown below.

[Chemical Formula 2]

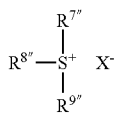

(b1-11)

In formula (b1-11), each of $R^{7'''}$ to $R^{9'''}$ independently represents an aryl group or an alkyl group, and two of $R^{7'''}$ to $R^{9'''}$ may be bonded to each other to form a ring with the sulfur atom, with the provision that at least one of $R^{7'''}$ to $R^{9'''}$ represents a substituted aryl group having a group represented by general formula (I) shown below as a substituent; and $X^-$ represents an anion.

[Chemical Formula 3]

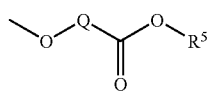

(I)

In formula (I), $R^5$ represents an organic group having a carbonyl group, an ester bond or a sulfonyl group; and Q represents a divalent linking group.

A fourth aspect of the present invention is an acid generator including the compound of the third aspect.

In the present description and claims, an "alkyl group" includes linear, branched or cyclic, monovalent saturated hydrocarbon, unless otherwise specified.

The term "alkylene group" includes linear, branched or cyclic divalent saturated hydrocarbon, unless otherwise specified.

A "lower alkyl group" is an alkyl group of 1 to 5 carbon atoms.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

The term "aliphatic" is a relative concept used in relation to the term "aromatic", and defines a group or compound that has no aromaticity.

The term "structural unit" refers to a monomer unit that contributes to the formation of a polymeric compound (polymer, copolymer).

The term "exposure" is used as a general concept that includes irradiation with any form of radiation.

According to the present invention, there are provided a novel compound useful as an acid generator for a resist composition, an acid generator including the compound, a resist composition containing the acid generator, and a method of forming a resist pattern using the resist composition.

BRIEF DESCRIPTION OF THE DRAWINGS

FIG. 1 is a graph showing a relationship between the EL margin and the DOF with respect to a dense CH pattern.

DETAILED DESCRIPTION OF THE INVENTION

Resist Composition

The resist composition according to the first aspect of the present invention includes a base component (A) which exhibits changed solubility in an alkali developing solution under action of acid (hereafter, referred to as "component (A)") and an acid-generator component (B) which generates acid upon exposure (hereafter, referred to as "component (B)").

With respect to a resist film formed using the resist composition, when a selective exposure is conducted during formation of a resist pattern, acid is generated from the component (B), and the generated acid acts on the component (A) to change the solubility of the component (A) in an alkali developing solution. As a result, the solubility of the exposed portions in an alkali developing solution is changed, whereas the solubility of the unexposed portions in an alkali developing solution remains unchanged. Therefore, the exposed portions are dissolved and removed by alkali developing in the case of a positive resist composition, whereas unexposed portions are dissolved and removed in the case of a negative resist composition, and hence, a resist pattern can be formed.

The resist composition of the present invention may be either a negative resist composition or a positive resist composition.

Furthermore, the resist composition of the present invention may include a nitrogen-containing organic compound (D), in addition to the component (A) and the component (B).

<Component (A)>

As the component (A), an organic compound typically used as a base component for a chemically amplified resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compounds having a molecular weight of 500 or more are broadly classified into low molecular weight organic compounds having a molecular weight of 500 to less than 2,000 (hereafter, referred to as "low molecular weight materials") and high molecular weight resins having a molecular weight of 2,000 or more (namely, "polymeric materials"). Generally, as the aforementioned low molecular weight compound, a non-polymer is used. With respect to the aforementioned resin (polymer or copolymer), the molecular weight is the polystyrene equivalent value determined by gel permeation chromatography (GPC). Hereafter, a "resin" refers to a resin having a molecular weight of 2,000 or more.

As the component (A), a resin component which exhibits changed solubility in an alkali developing solution under action of acid may be used. Alternatively, as the component (A), a low molecular weight material which exhibits changed solubility in an alkali developing solution under action of acid may be used.

When the resist composition of the present invention is a negative resist composition, for example, as the component (A), a base component that is soluble in an alkali developing solution is used, and a cross-linking agent is blended in the negative resist composition.

In the negative resist composition, when acid is generated from the component (B) upon exposure, the action of the generated acid causes cross-linking between the base component and the cross-linking agent, and the cross-linked portion becomes insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the component (A) for a negative resist composition, a resin that is soluble in an alkali developing solution (hereafter, referred to as "alkali-soluble resin") is used.

As the alkali-soluble resin, it is preferable to use a resin having a structural unit derived from at least one of α-(hydroxyalkyl)acrylic acid and a lower alkyl ester of α-(hydroxyalkyl)acrylic acid, or a resin having a fluorinated alcohol as disclosed in Japanese Unexamined Patent Application, First Publication No. 2005-336452 or 2006-259582, as it enables formation of a satisfactory resist pattern with minimal swelling. Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group is preferable, as it enables formation of a resist pattern with minimal swelling. The amount of the cross-linker added is preferably within a range from 1 to 50 parts by weight, relative to 100 parts by weight of the alkali-soluble resin.

When the resist composition of the present invention is a positive resist composition, as the component (A), a base component (A') which exhibits increased solubility in an alkali developing solution by action of acid (hereafter, referred to as "component (A')") is used.

The component (A') is insoluble in an alkali developing solution prior to exposure, and when acid is generated from the component (B) upon exposure, the solubility of the component (A') in an alkali developing solution increases. Therefore, in the formation of a resist pattern, by conducting selective exposure of a resist film formed by applying the positive resist composition onto a substrate, the exposed portions changes from an insoluble state to a soluble state in an alkali developing solution, whereas the unexposed portions remain insoluble in an alkali developing solution, and hence, a resist pattern can be formed by alkali developing.

In the resist composition of the present invention, the component (A) is preferably a base component (A') which exhibits increased solubility in an alkali developing solution under action of acid. That is, the resist composition of the present invention is preferably a positive resist composition.

The component (A') may be a resin component (A1) that exhibits increased solubility in an alkali developing solution under the action of acid (hereafter, frequently referred to as "component (A1)"), a low molecular weight material (A2) that exhibits increased solubility in an alkali developing solution under the action of acid (hereafter, frequently referred to as "component (A2)"), or a mixture thereof.

[Component (A1)]

As the component (A1), a resin component (base resin) typically used as a base component for a chemically amplified resist composition can be used alone, or two or more of such resin components can be mixed together.

In the present invention, it is preferable that the component (A1) include a structural unit derived from an acrylate ester.

In the present descriptions and claims, the term "structural unit derived from an acrylate ester" refers to a structural unit which is formed by the cleavage of the ethylenic double bond of an acrylate ester.

The term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. As the substituent, a lower alkyl group or a halogenated lower alkyl group can be used.

With respect to the "structural unit derived from an acrylate ester", the "α-position (the carbon atom on the α-position)" refers to the carbon atom having the carbonyl group bonded thereto, unless specified otherwise.

With respect to the acrylate ester, specific examples of the lower alkyl group for the substituent at the α-position include linear or branched alkyl groups such as a methyl group, an ethyl group, a propyl group, an isopropyl group, an n-butyl group, an isobutyl group, a tert-butyl group, a pentyl group, an isopentyl group, and a neopentyl group.

Specific examples of the halogenated lower allyl group include groups in which part or all of the hydrogen atoms of the aforementioned "lower alkyl group for the substituent at the α-position" are substituted with halogen atoms. Examples of halogen atoms include fluorine atoms, chlorine atoms, bromine atoms and iodine atoms, and fluorine atoms are particularly desirable.

In the present invention, it is preferable that a hydrogen atom, a lower alkyl group or a halogenated lower alkyl group is bonded to the α-position of the acrylate ester, a hydrogen atom, a lower alkyl group or a fluorinated lower alkyl group is more preferable, and in terms of industrial availability, a hydrogen atom or a methyl group is the most desirable.

In the resist composition of the present invention, it is particularly desirable that the component (A1) include a structural unit (a1) derived from an acrylate ester containing an acid dissociable, dissolution inhibiting group.

Further, it is preferable that the component (A1) have a structural unit (a2) derived from an acrylate ester containing a lactone-containing cyclic group, as well as the structural unit (a1).

Furthermore, it is preferable that the component (A1) have a structural unit (a3) derived from an acrylate ester containing a polar group-containing aliphatic hydrocarbon group, as well as the structural unit (a1), or the structural unit (a1) and the structural unit (a2).

Structural Unit (a1)

The structural unit (a1) is a structural unit derived from an acrylate ester containing an acid dissociable, dissolution inhibiting group.

As the acid dissociable, dissolution inhibiting group in the structural unit (a1), any of the groups that have been proposed as acid dissociable, dissolution inhibiting groups for the base resins of chemically amplified resists can be used, provided the group has an alkali dissolution-inhibiting effect that renders the entire component (A1) insoluble in an alkali developing solution prior to dissociation, and then following dissociation by action of acid, increases the solubility of the entire component (A1) in the alkali developing solution. Generally, groups that form either a cyclic or chain-like tertiary alkyl ester with the carboxyl group of the (meth)acrylic acid, and acetal-type acid dissociable, dissolution inhibiting groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

In the present description and claims, the term "aliphatic branched" refers to a branched structure having no aromaticity.

The "aliphatic branched, acid dissociable, dissolution inhibiting group" is not limited to be constituted of only carbon atoms and hydrogen atoms (not limited to hydrocarbon groups); but is preferably a hydrocarbon group.

Further, the "hydrocarbon group" may be either saturated or unsaturated, but is preferably saturated.

Examples of aliphatic branched, acid dissociable, dissolution inhibiting groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of substituents include lower alkyl groups of 1 to 5 carbon atoms, lower alkoxy groups of 1 to 5 carbon atoms, fluorine atom, fluorinated lower alkyl groups of 1 to 5 carbon atoms, and oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated lower alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

As the aliphatic cyclic group-containing acid dissociable, dissolution inhibiting group, for example, a group which has a tertiary carbon atom on the ring structure of the cycloalkyl group can be used. Specific examples include 2-methyl-2-adamantyl group and a 2-ethyl-2-adamantyl group. Further, groups having an aliphatic cyclic group such as an adamantyl group, cyclohexyl group, cyclopentyl group, norbornyl group, tricyclodecanyl group or tetracyclododecanyl group, and a branched alkylene group having a tertiary carbon atom bonded thereto, as the groups bonded to the oxygen atom of the carbonyl group (—C(O)—O—) within the structural units represented by general formulas (a1"-1) to (a1"-6) shown below, can be used.

[Chemical Formula 4]

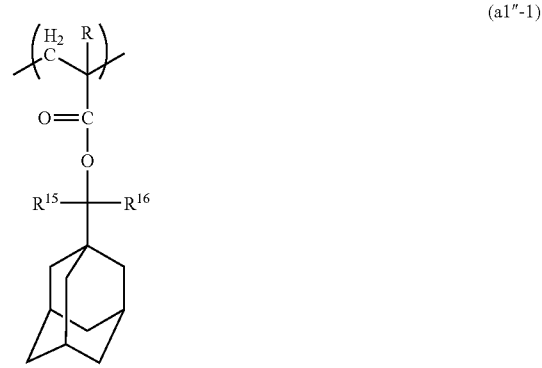

(a1"-1)

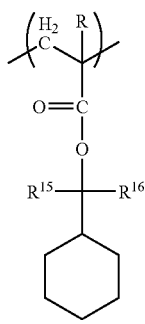

(a1″-2)

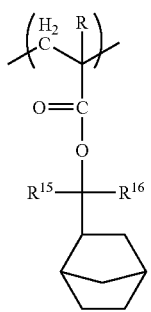

(a1″-3)

(a1″-4)

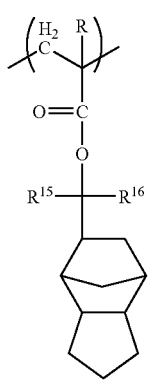

(a1″-5)

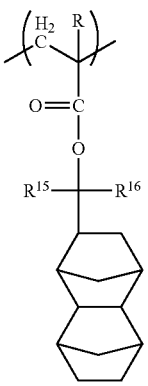

(a1″-6)

In the formulas, R represents a hydrogen atom, a lower alkyl group or a halogenated lower alkyl group; and $R^{15}$ and $R^{16}$ each independently represent an alkyl group (which may be linear or branched, and preferably has 1 to 5 carbon atoms).

In general formulas (a1″-1) to (a1″-6) above, the lower alkyl group or halogenated lower alkyl group for R are the same as the lower alkyl group or halogenated lower alkyl group which can be bonded to the α-position of the aforementioned acrylate ester.

An "acetal-type acid dissociable, dissolution inhibiting group" generally substitutes a hydrogen atom at the terminal of an alkali-soluble group such as a carboxy group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 5]

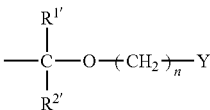

(p1)

In the formula, $R^{1\prime}$ and $R^{2\prime}$ each independently represent a hydrogen atom or a lower alkyl group; n represents an integer of 0 to 3; and Y represents a lower alkyl group or an aliphatic cyclic group.

In general formula (p1) above, n is preferably an integer of 0 to 2, more preferably 0 or 1, and most preferably 0.

As the lower alkyl group for $R^{1\prime}$ and $R^{2\prime}$, the same lower alkyl groups as those described above for R can be used, although a methyl group or ethyl group is preferable, and a methyl group is particularly desirable.

In the present invention, it is preferable that at least one of $R^{1\prime}$ and $R^{2\prime}$ be a hydrogen atom. That is, it is preferable that the acid dissociable, dissolution inhibiting group (p1) is a group represented by general formula (p1-1) shown below.

[Chemical Formula 6]

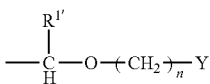
(p1-1)

In the formula, $R^{1\prime}$, n and Y are the same as defined above.

As the lower alkyl group for Y, the same as the lower alkyl groups for R above can be used.

As the aliphatic cyclic group for Y, any of the aliphatic monocyclic/polycyclic groups which have been proposed for conventional ArF resists and the like can be appropriately selected for use. For example, the same groups described above in connection with the "aliphatic cyclic group" can be used.

Further, as the acetal-type, acid dissociable, dissolution inhibiting group, groups represented by general formula (p2) shown below can also be used.

[Chemical Formula 7]

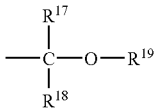
(p2)

In the formula, $R^{17}$ and $R^{18}$ each independently represent a linear or branched alkyl group or a hydrogen atom; and $R^{19}$ represents a linear, branched or cyclic alkyl group; or $R^{17}$ and $R^{19}$ each independently represents a linear or branched alkylene group, and the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable. It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4 to 7-membered ring, and more preferably a 4 to 6-membered ring. Specific examples of the cyclic group include tetrahydropyranyl group and tetrahydrofuranyl group.

As the structural unit (a1), it is preferable to use at least one member selected from the group consisting of structural units represented by formula (a1-0-1) shown below and structural units represented by formula (a1-0-2) shown below.

[Chemical Formula 8]

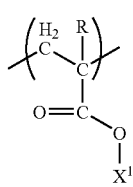
(a1-0-1)

In the formula, R represents a hydrogen atom, a lower alkyl group, or a halogenated lower alkyl group; and $X^1$ represents an acid dissociable, dissolution inhibiting group.

[Chemical Formula 9]

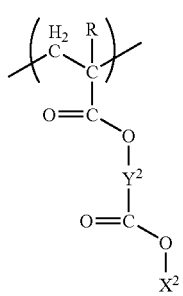
(a1-0-2)

In the formula, R represents a hydrogen atom, a lower alkyl group or a halogenated lower alkyl group; $X^2$ represents an acid dissociable, dissolution inhibiting group; and $Y^2$ represents a divalent linking group.

In general formula (a1-0-1) shown above, lower alkyl group and halogenated lower alkyl group for R are the same as the lower alkyl group and halogenated lower alkyl group which can be bonded to the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is the same as defined above.

$X^2$ is the same as defined for $X^1$ in general formula (a1-0-1).

As the divalent linking group for $Y^2$, an alkylene group, a divalent aliphatic cyclic group or a divalent linking group containing a hetero atom can be mentioned.

As the aliphatic cyclic group, the same as those used above in connection with the explanation of "aliphatic cyclic group" can be used, except that two hydrogen atoms have been removed therefrom.

When $Y^2$ represents an alkylene group, it preferably has 1 to 10 carbon atoms, more preferably 1 to 6, still more preferably 1 to 4, and most preferably 1 to 3.

When $Y^2$ represents a divalent aliphatic cyclic group, it is particularly desirable that the divalent aliphatic cyclic group be a group in which two or more hydrogen atoms have been removed from cyclopentane, cyclohexane, norbornane, isobornane, adamantane, tricyclodecane or tetracyclododecane.

When $Y^2$ represents a divalent linking group containing a hetero atom, examples thereof include —O—, —C(=O)—O—, —C(=O)—, —O—C(=O)—O—, —C(=O)—NH—, —NH— (H may be substituted with a substituent such as an alkyl group or an acyl group), —S—, —S(=O)$_2$—, —S(=O)$_2$—O—, and "-A-O—B— (wherein O is an oxygen atom, and each of A and B independently represents a divalent hydrocarbon group which may have a substituent).

When $Y^2$ represents a divalent linking group —NH— and the H in the formula is replaced with a substituent such as an alkyl group or an acyl group, the substituent preferably has 1 to 10 carbon atoms, more preferably 1 to 8 carbon atoms, and most preferably 1 to 5 carbon atoms.

When $Y^2$ is "A-O—B", each of A and B independently represents a divalent hydrocarbon group which may have a substituent.

A hydrocarbon "has a substituent" means that part or all of the hydrogen atoms within the hydrocarbon group is substituted with groups or atoms other than hydrogen atom.

The hydrocarbon group for A may be either an aliphatic hydrocarbon group, or an aromatic hydrocarbon group. An "aliphatic hydrocarbon group" refers to a hydrocarbon group that has no aromaticity.

The aliphatic hydrocarbon group for A may be either saturated or unsaturated. In general, the aliphatic hydrocarbon group is preferably saturated.

As specific examples of the aliphatic hydrocarbon group for A, a linear or branched aliphatic hydrocarbon group, and an aliphatic hydrocarbon group having a ring in the structure thereof can be given.

The linear or branched aliphatic hydrocarbon group preferably has 1 to 10 carbon atoms, more preferably 1 to 8, still more preferably 2 to 5, and most preferably 2.

As a linear aliphatic hydrocarbon group, a linear alkylene group is preferable, and specific examples include a methylene group, an ethylene group [—(CH$_2$)$_2$—], a trimethylene group [—(CH$_2$)$_3$—], a tetramethylene group [—(CH$_2$)$_4$—] and a pentamethylene group [—(CH$_2$)$_5$—].

As the branched aliphatic hydrocarbon group, a branched alkylene group is preferable, and specific examples include alkylalkylene groups, e.g., alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—; allyltrimethylene groups such as —CH(CH$_3$)CH$_2$CH$_2$— and —CH$_2$CH(CH$_3$)CH$_2$—; and alkyltetramethylene groups such as —CH(CH$_3$)CH$_2$CH$_2$CH$_2$— and —CH$_2$CH(CH$_3$)CH$_2$CH$_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of substituents include a fluorine atom, a fluorinated lower alkyl group of 1 to 5 carbon atoms, and an oxygen atom (=O).

As examples of the hydrocarbon group containing a ring, a cyclic aliphatic hydrocarbon group (a group in which two hydrogen atoms have been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of substituents include a lower alkyl group of 1 to 5 carbon atoms, a fluorine atom, a fluorinated lower alkyl group of 1 to 5 carbon atoms, and an oxygen atom (=O).

As A, a linear aliphatic hydrocarbon group is preferable, more preferably a linear alkylene group, still more preferably a linear alkylene group of 2 to 5 carbon atoms, and most preferably an ethylene group.

As the hydrocarbon group for B, the same divalent hydrocarbon groups as those described above for A can be used.

As B, a linear or branched aliphatic hydrocarbon group is preferable, and a methylene group or an alkylmethylene group is particularly desirable.

The alkyl group within the alkyl methylene group is preferably a linear alkyl group of 1 to 5 carbon atoms, more preferably a linear alkyl group of 1 to 3 carbon atoms, and most preferably a methyl group.

Specific examples of the structural unit (a1) include structural units represented by general formulas (a1-1) to (a1-4) shown below.

[Chemical Formula 10]

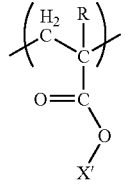

(a1-1)

(a1-2)
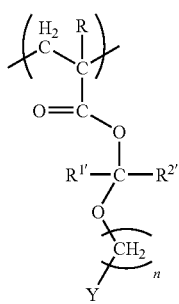

(a1-3)
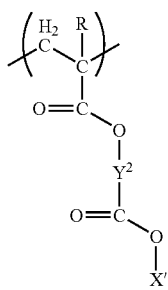

(a1-4)
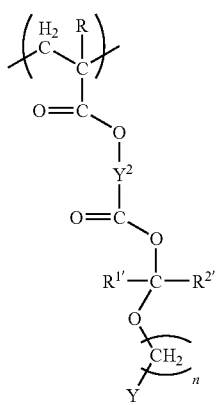

In the formulas, X' represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ represents a divalent linking group; R is the same as defined above; and each of $R^{1'}$ and $R^{2'}$ independently represents a hydrogen atom or a lower alkyl group of 1 to 5 carbon atoms.

Examples of the tertiary alkyl ester-type acid dissociable, dissolution inhibiting group for X' include the same tertiary alkyl ester-type acid dissociable, dissolution inhibiting groups as those described above for $X^1$.

As $R^{1'}$, $R^{2'}$, n and Y are respectively the same as defined for $R^{1'}$, $R^{2'}$, n and Y in general formula (p1) described above in connection with the "acetal-type acid dissociable, dissolution inhibiting group".

As examples of $Y^2$, the same groups as those described above for $Y^2$ in general formula (a1-0-2) can be given.

Specific examples of structural units represented by general formula (a1-1) to (a1-4) are shown below.

In the formulas shown below, $R^\alpha$ represents a hydrogen atom, a methyl group or a trifluoromethyl group.

[Chemical Formula 11]

(a1-1-1)
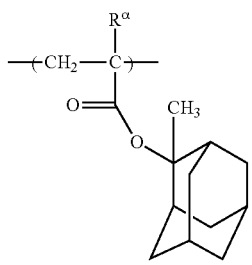

(a1-1-2)
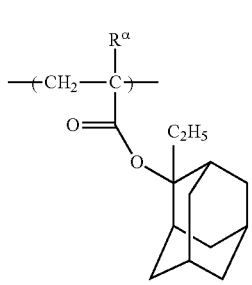

(a1-1-3)
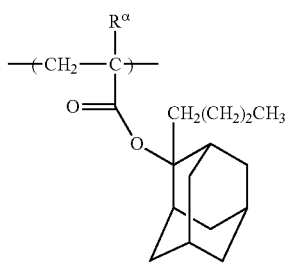

(a1-1-4)
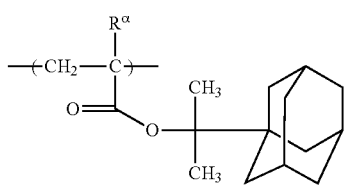

(a1-1-5)
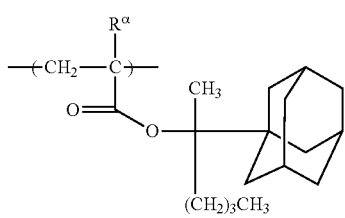

(a1-1-6)
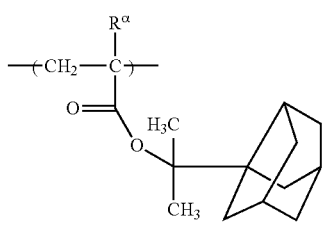

(a1-1-7)
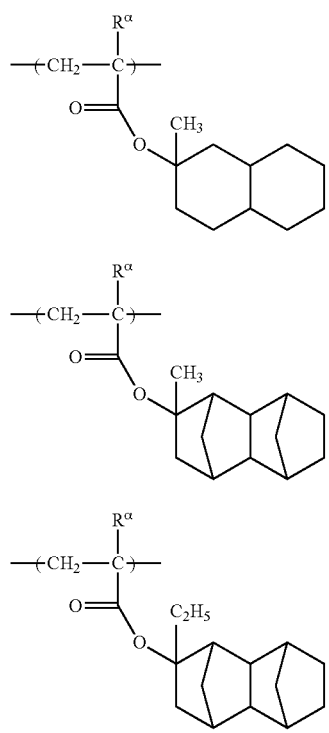
(a1-1-8)
(a1-1-9)
[Chemical Formula 12]
(a1-1-10)
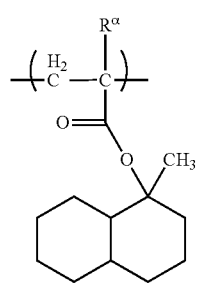
(a1-1-11)
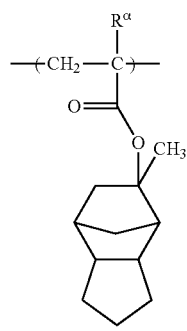
(a1-1-12)
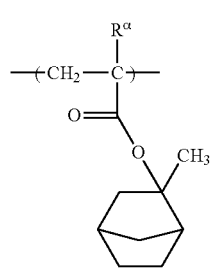
(a1-1-13)
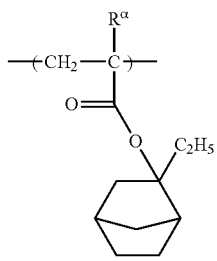
(a1-1-14)
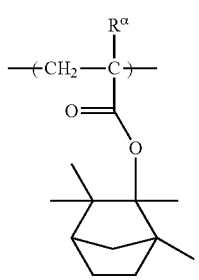
(a1-1-15)
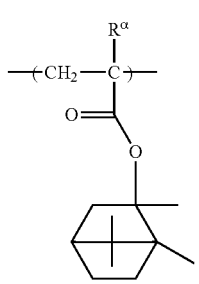
(a1-1-16)
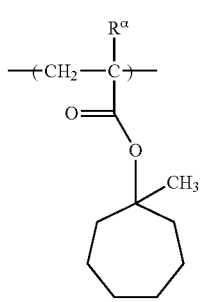
(a1-1-17)
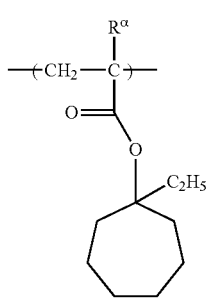

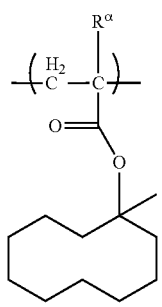 (a1-1-18)
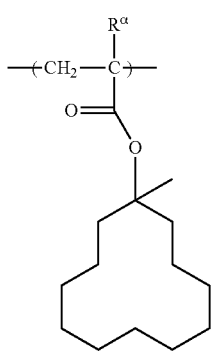 (a1-1-19)
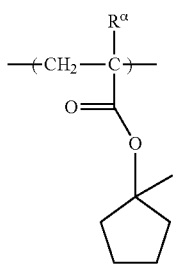 (a1-1-20)
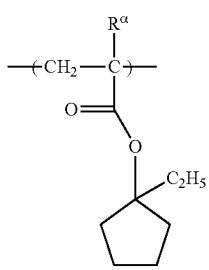 (a1-1-21)
[Chemical Formula 13]
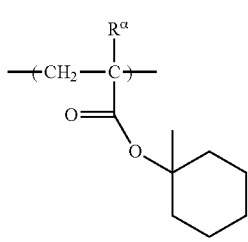 (a1-1-22)
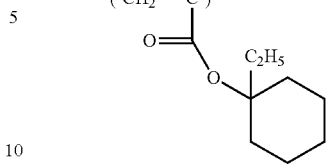 (a1-1-23)
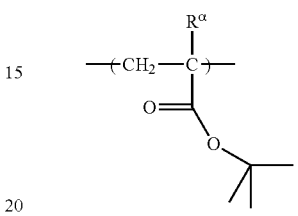 (a1-1-24)
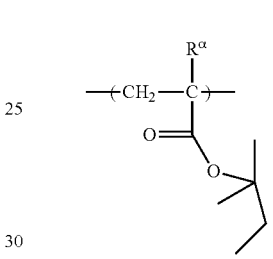 (a1-1-25)
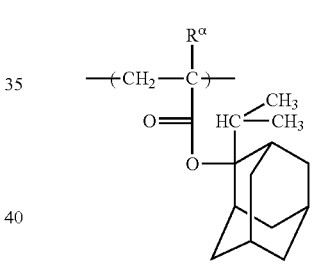 (a1-1-26)
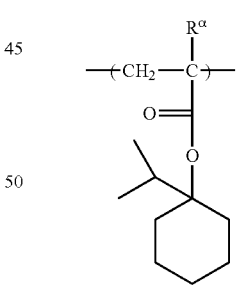 (a1-1-27)
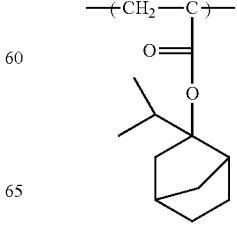 (a1-1-28)

-continued
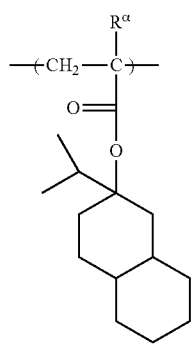 (a1-1-29)
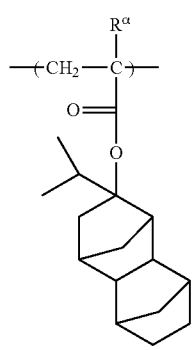 (a1-1-30)
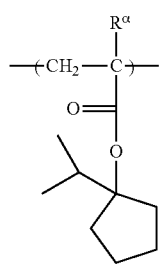 (a1-1-31)
[Chemical Formula 14]
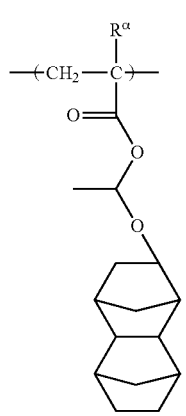 (a1-2-1)
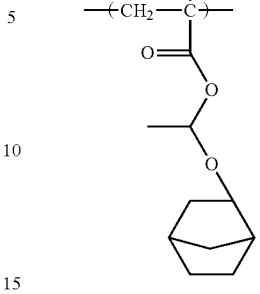 (a1-2-2)
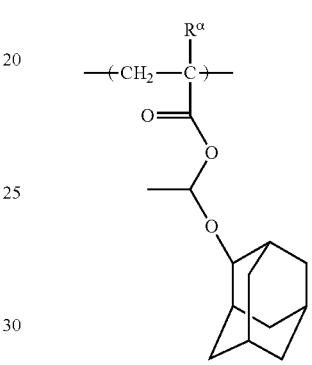 (a1-2-3)
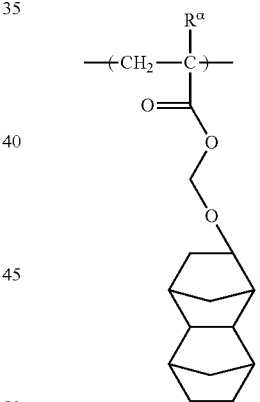 (a1-2-4)
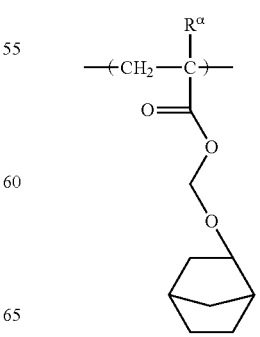 (a1-2-5)

(a1-2-6) 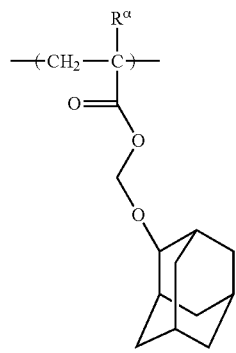
(a1-2-10) 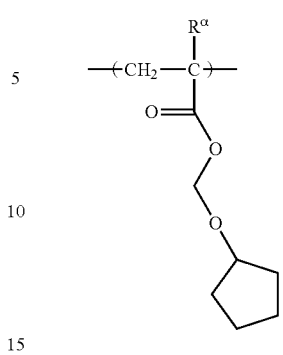
(a1-2-7) 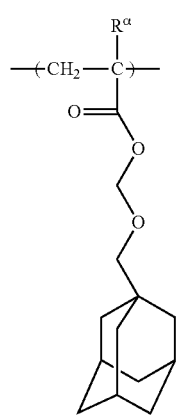
(a1-2-11) 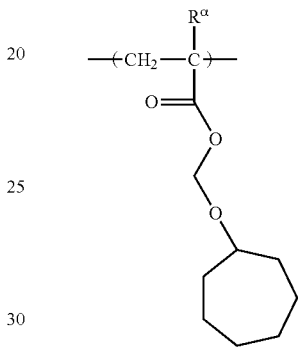
(a1-2-8) 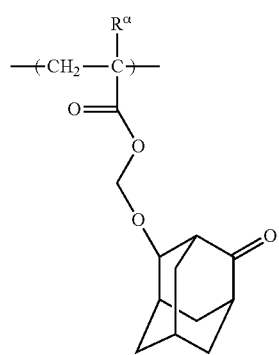
(a1-2-12) 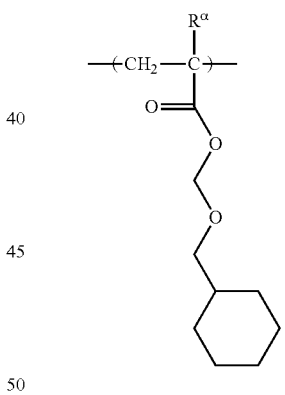
(a1-2-9) 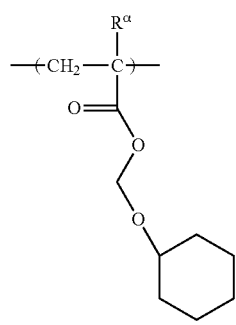
(a1-2-13) 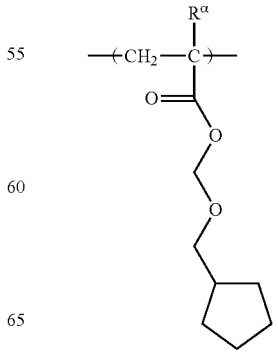

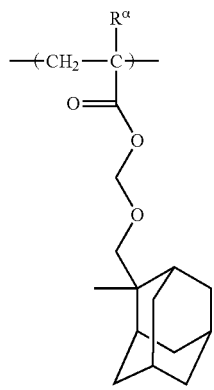 (a1-2-14)
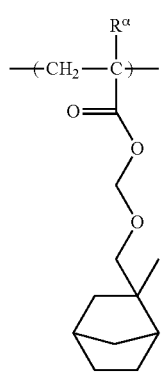 (a1-2-15)
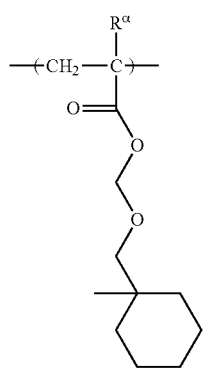 (a1-2-16)
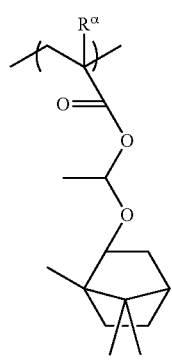 (a1-2-17)
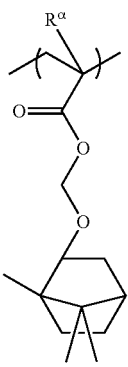 (a1-2-18)
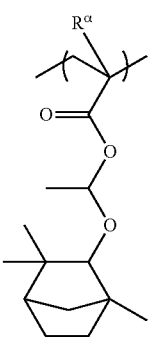 (a1-2-19)
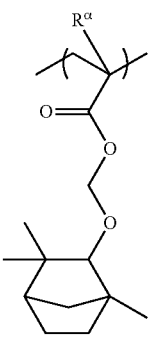 (a1-2-20)
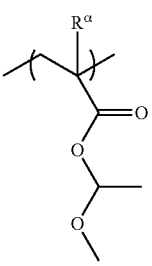 (a1-2-21)
(a1-2-22)

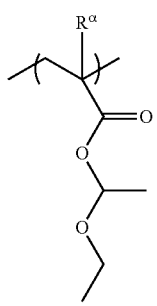
(a1-2-23)
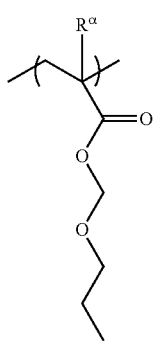
(a1-2-24)
[Chemical Formula 15]
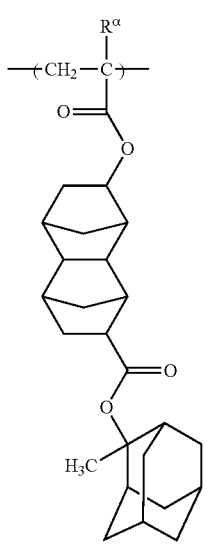
(a1-3-1)
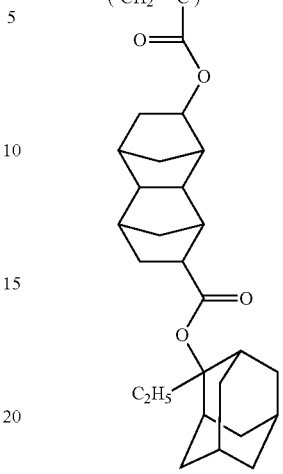
(a1-3-2)
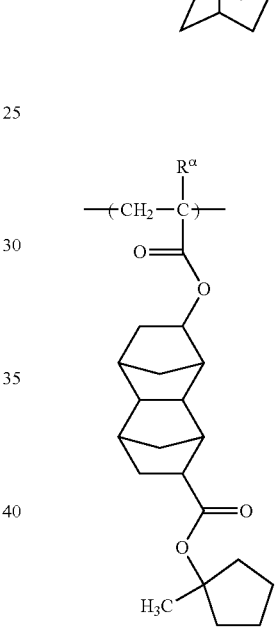
(a1-3-3)
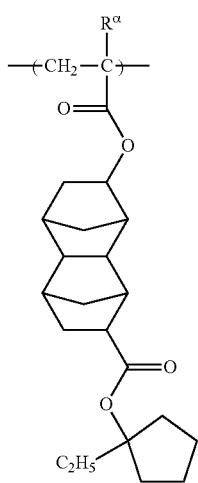
(a1-3-4)

(a1-3-5)
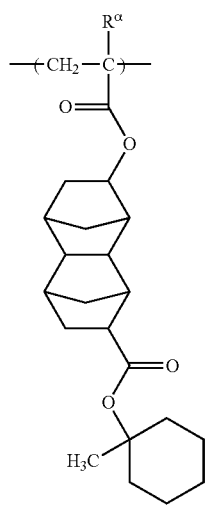
(a1-3-8)
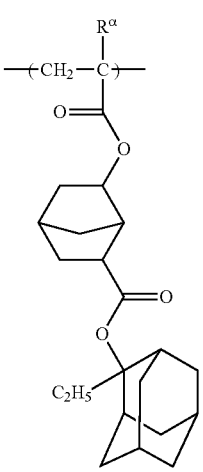
(a1-3-6)
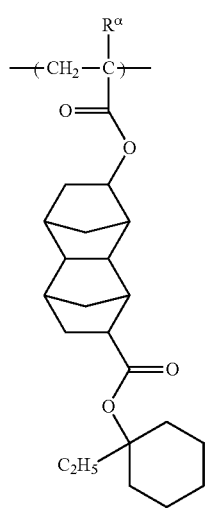
(a1-3-9)
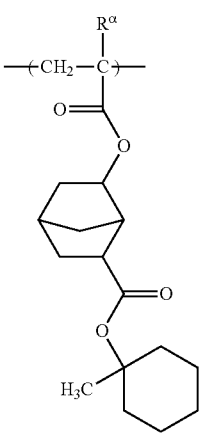
(a1-3-7)
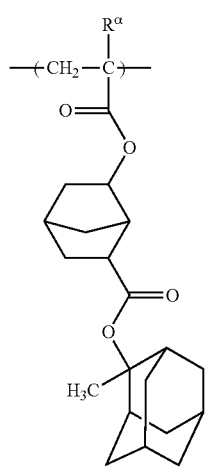
(a1-3-10)
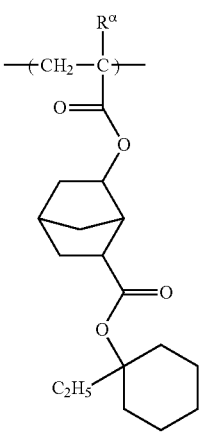

(a1-3-11) 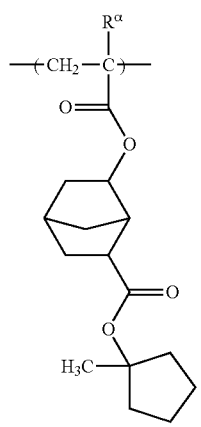
(a1-3-12) 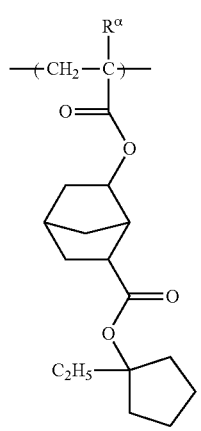
(a1-3-13) 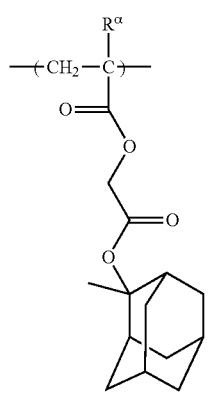
(a1-3-14) 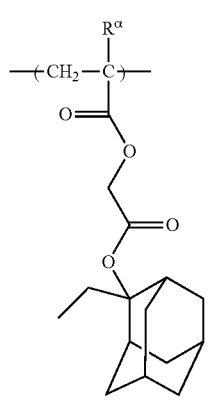
(a1-3-15) 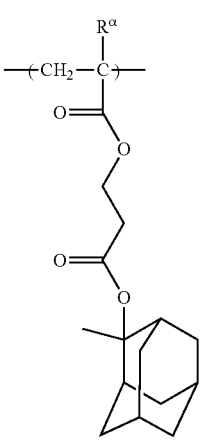
(a1-3-16) 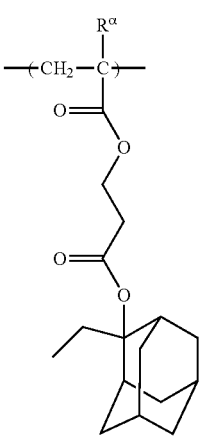
(a1-3-17) 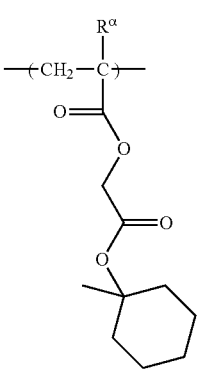
(a1-3-18) 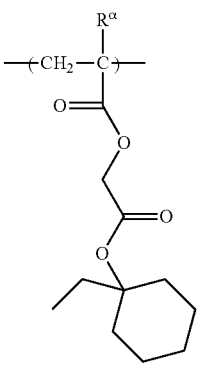

[Chemical Formula 16]
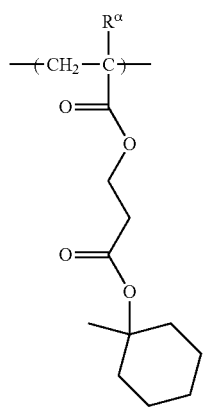 (a1-3-19)
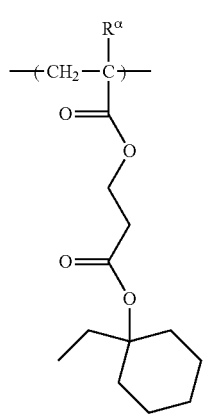 (a1-3-20)
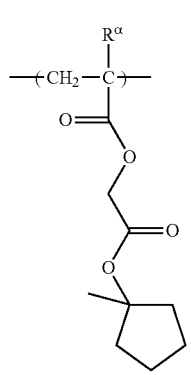 (a1-3-21)
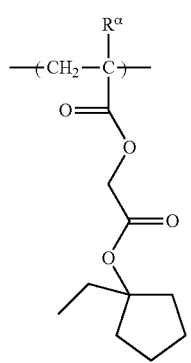 (a1-3-22)
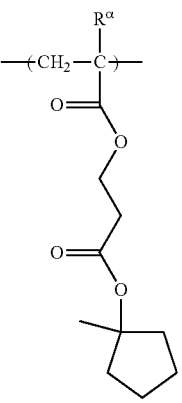 (a1-3-23)
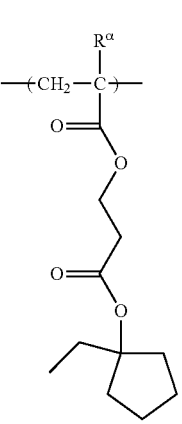 (a1-3-24)
[Chemical Formula 17]
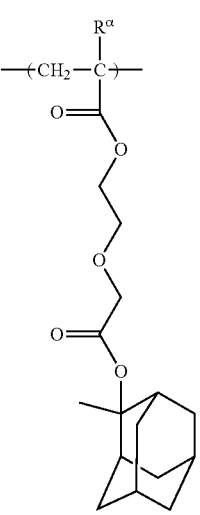 (a1-3-25)

(a1-3-26)
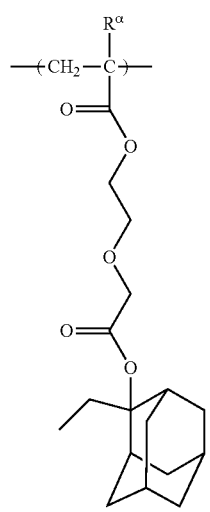
(a1-3-29)
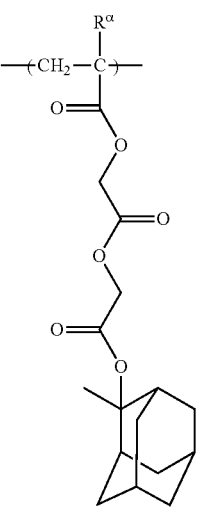
(a1-3-27)
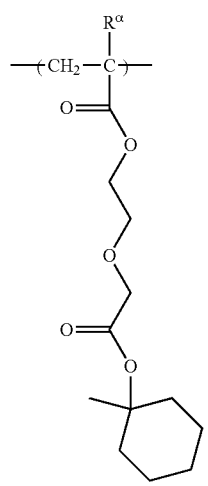
(a1-3-30)
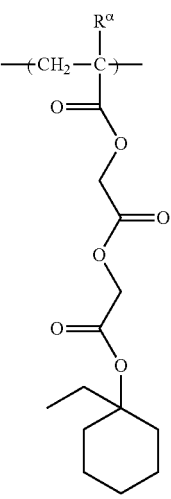
(a1-3-28)
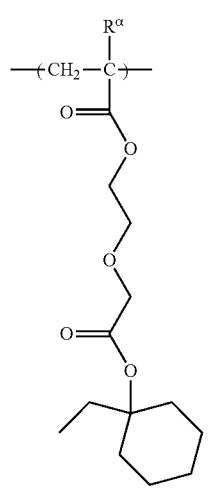
(a1-3-31)
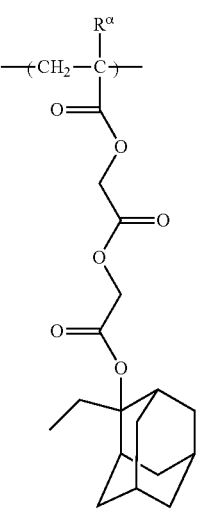

(a1-3-32)
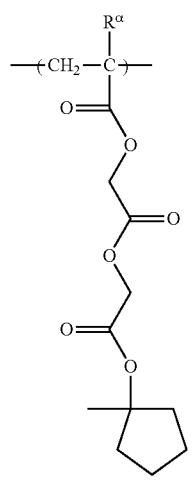
[Chemical Formula 18]
(a1-4-1)
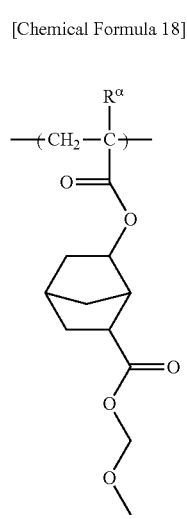
(a1-4-2)
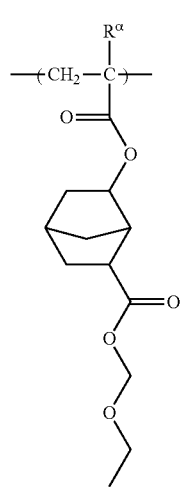
(a1-4-3)
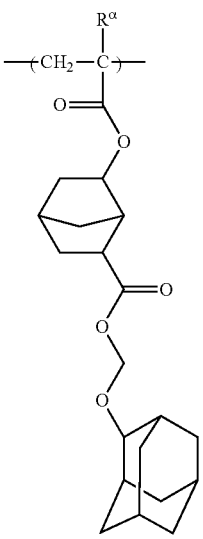
(a1-4-4)
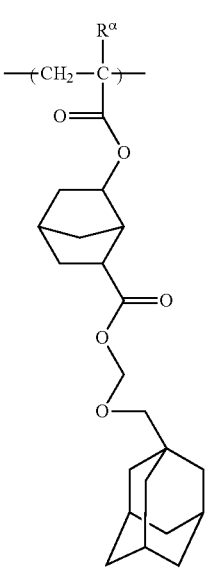
(a1-4-5)
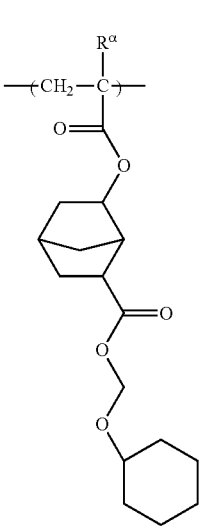

(a1-4-6) 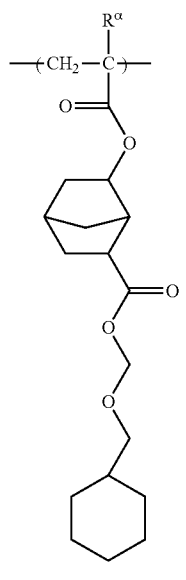
(a1-4-7) 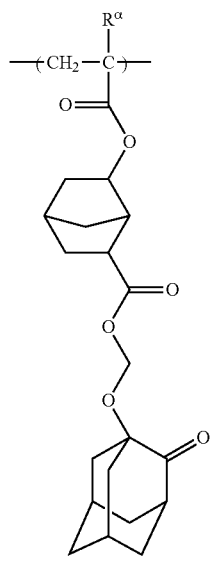
(a1-4-8) 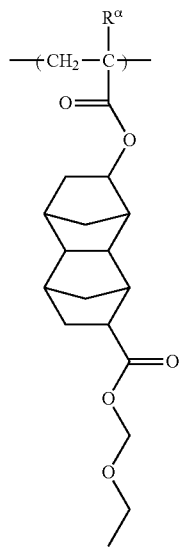
(a1-4-9) 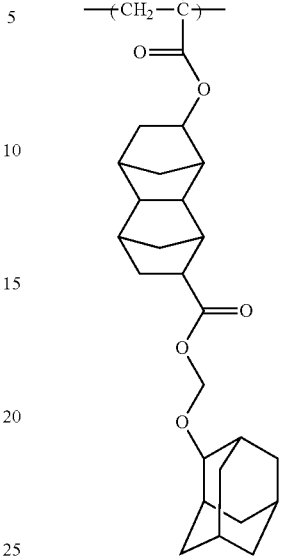
(a1-4-10) 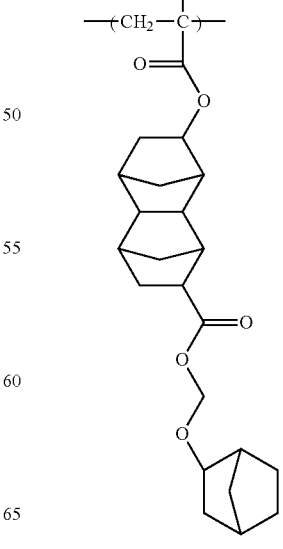

(a1-4-11)
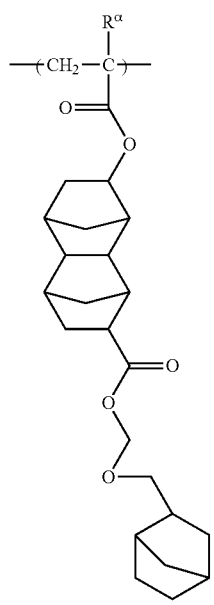
(a1-4-12)
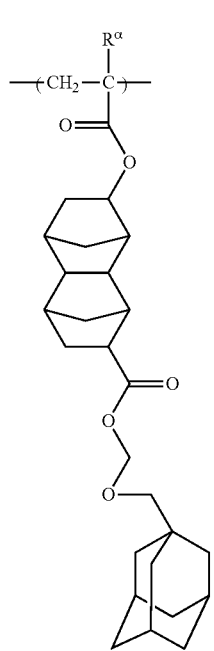
(a1-4-13)
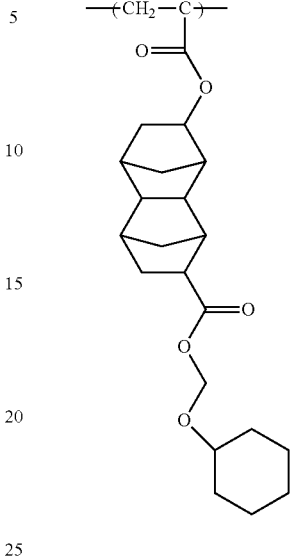
(a1-4-14)
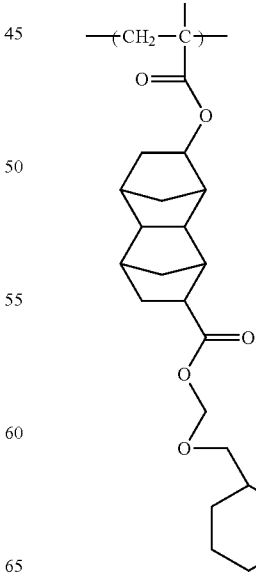

As the structural unit (a1), one type of structural unit may be used alone, or two or more types of structural units may be used in combination.

Among these, structural units represented by general formula (a1-1) or (a1-3) are preferable. More specifically, at least one structural unit selected from the group consisting of structural units represented by formulas (a1-1-1) to (a-1-1-4), (a1-1-20) to (a1-1-23) and (a1-3-25) to (a1-3-28) is more preferable.

Further, as the structural unit (a1), structural units represented by general formula (a1-1-01) shown below which includes the structural units represented by formulas (a1-1-1) to (a1-1-3), structural units represented by general formula (a1-1-02) shown below which includes the structural units represented by formulas (a1-1-16), (a1-1-17) and (a1-1-20) to (a1-1-23), structural units represented by general formula (a1-3-01) shown below which include the structural units represented by formulas (a1-3-25) and (a1-3-26), and structural units represented by general formula (a1-3-02) shown below which include the structural units represented by formulas (a1-3-27) and (a1-3-28) are also preferable.

[Chemical Formula 19]

(a1-1-01)

In the formula, R represents a hydrogen atom, a lower alkyl group or a halogenated lower alkyl group; and $R^{11}$ represents a lower alkyl group. $R^{12}$ represents a lower alkyl group. h represents an integer of 1 to 6.

In general formula (a1-1-01), it is the same as defined above. The lower alkyl group for $R^{11}$ is the same as defined for the lower alkyl group for R above, and is preferably a methyl group, an ethyl group or an isopropyl group.

In general formula (a1-1-02), R is the same as defined above. The lower alkyl group for $R^{12}$ is the same as the lower alkyl group for R above. $R^{12}$ is preferably a methyl group or an ethyl group, and most preferably an ethyl group. h is preferably 1 or 2, and most preferably 2.

[Chemical Formula 20]

(a1-3-01)

In the formula, R represents a hydrogen atom, a lower alkyl group or a halogenated lower alkyl group; $R^{14}$ represents a lower alkyl group; $R^{13}$ represents a hydrogen atom or a methyl group; and a represents an integer of 1 to 10.

[Chemical Formula 21]

(a1-3-02)

In the formula, R represents a hydrogen atom, a lower alkyl group or a halogenated lower alkyl group; $R^{14}$ represents a lower alkyl group; $R^{13}$ represents a hydrogen atom or a methyl group; a represents an integer of 1 to 10; and n' represents an integer of 1 to 6.

In general formulas (a1-3-01) and (a1-3-02), R is the same as defined above.

$R^{13}$ is preferably a hydrogen atom.

The lower alkyl group for $R^{14}$ is the same as the lower alkyl group for R, and is preferably a methyl group or an ethyl group.

a is preferably an integer of 1 to 8, more preferably an integer of 2 to 5, and most preferably 2.

[Chemical Formula 22]

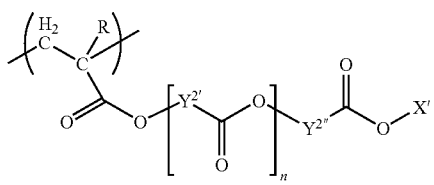
(a1-3-03)

In the formula, R is as defined above; each of $Y^{2'}$ and $Y^{2''}$ independently represents a divalent linking group; X' represents an acid dissociable, dissolution inhibiting group; and n represents an integer of 1 to 3.

In general formula (a1-3-03), as the divalent linking group for $Y^{2'}$ and $Y^{2''}$, the same groups as those described above for $Y^2$ in general formula (a1-3) can be used.

As $Y^{2'}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As $Y^{2''}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As the acid dissociable, dissolution inhibiting group for X', the same groups as those described above can be used. X' is preferably a tertiary alkyl ester-type acid dissociable, dissolution inhibiting group, more preferably a cyclic alkyl group (a monovalent aliphatic cyclic group) having a tertiary carbon atom on the ring skeleton, and specific examples thereof include a 2-methyl-2-adamantyl group.

n is the same as defined above, preferably an integer of 0 to 2, more preferably 0 or 1, and most preferably 0.

As the structural unit represented by general formula (a1-3-03), a structural unit represented by general formula (a1-3-03-1) or (a1-3-03-2) shown below is preferable. Among these, a structural unit represented by general formula (a1-3-03-1) is preferable, and a structural unit represented by the aforementioned formula (a1-3-29) or (a1-3-30) is particularly desirable.

[Chemical Formula 23]

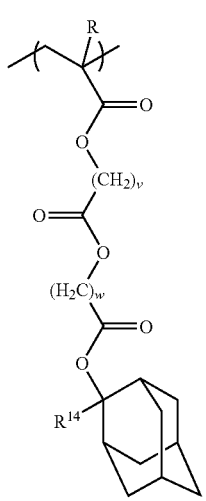
(a1-3-03-1)

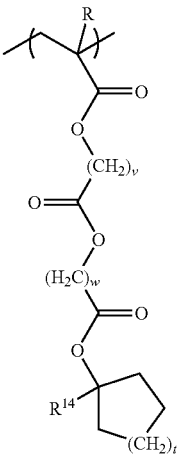
(a1-3-03-2)

In the formulas, R and $R^{14}$ are the same as defined above; v represents an integer of 1 to 10; w represents an integer of 1 to 10; and t represents an integer of 0 to 3.

v is preferably an integer of 1 to 5, and most preferably 1 or 2.

w is preferably an integer of 1 to 5, and most preferably 1 or 2.

t is preferably an integer of 1 to 3, and most preferably 1 or 2.

In the component (A1), the amount of the structural unit (a1) based on the combined total of all structural units constituting the component (A1) is preferably 10 to 80 mol %, more preferably 20 to 70 mol %, and still more preferably 25 to 50 mol %. When the amount of the structural unit (a1) is at least as large as the lower limit of the above-mentioned range, a pattern can be easily formed using a resist composition prepared from the component (A1). On the other hand, when the amount of the structural unit (a1) is no more than the upper limit of the above-mentioned range, a good balance can be achieved with the other structural units.

The monomers for deriving the structural units represented by general formulas (a1-3-01) and (a1-3-02) above (hereafter, these monomers are collectively referred to as "monomers W") can be produced by a production method shown below.

Production Method of Monomer W:

A compound represented by general formula (X-2) shown below is added to a compound represented by general formula (X-1) shown below dissolved in a reaction solvent, in the presence of a base, and a reaction is effected to obtain a compound represented by general formula (X-3) shown below (hereafter, referred to as "compound (X-3)"). Then, a compound represented by general formula (X-4) shown below is added to the resulting solution having the compound (X-3) dissolved therein, in the presence of a base, and a reaction is effected to thereby obtain a monomer W.

Examples of the base include inorganic bases such as sodium hydride, $K_2CO_3$ and $Cs_2CO_3$; and organic bases such as triethylamine, 4-dimethylaminopyridine (DMAP) and pyridine.

As the reaction solvent, any reaction solvent capable of dissolving the compounds (X-1) and (X-2) as raw materials can be used, and specific examples include tetrahydrofuran (THF), acetone, dimethylformamide (DMF), dimethylacetamide, dimethylsulfoxide (DMSO) and acetonitrile.

[Chemical Formula 24]

 (X-1)

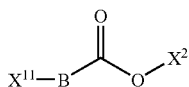 (X-2)

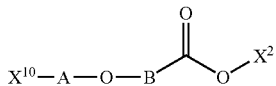 (X-3)

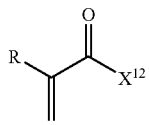 (X-4)

In the formulas, R represents a hydrogen atom, a lower alkyl group or a halogenated lower alkyl group; each of A and B independently represents a divalent hydrocarbon group which may have a substituent; $X^2$ represents an acid dissociable, dissolution inhibiting group; each of $X^{10}$ and $X^{12}$ independently represents a hydroxyl group or a halogen atom, with the provision that either one of $X^{10}$ and $X^{12}$ represents a hydroxyl group and the other represents a halogen atom; and $X^{11}$ represents a halogen atom.

In the formulas above, R, $X^2$, A and B are the same as defined above.

Examples of halogen atoms for $X^{10}$, $X^{11}$ and $X^{12}$ include a bromine atom, a chlorine atom, an iodine atom and a fluorine atom.

In terms of reactivity, the halogen atom for $X^{10}$ or $X^{12}$ is preferably a chlorine atom or a bromine atom.

As $X^{11}$, in terms of reactivity, a bromine atom or a chlorine atom is preferable, and a bromine atom is particularly desirable.

Structural Unit (a2)

The structural unit (a2) is a structural unit derived from an acrylate ester containing a lactone-containing cyclic group.

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the compatibility with the developing solution containing water.

As the structural unit (a2), there is no particular limitation, and an arbitrary structural unit may be used.

Specific examples of lactone-containing monocyclic groups include a group in which one hydrogen atom has been removed from a 4- to 6-membered lactone ring, such as a group in which one hydrogen atom has been removed from β-propionolatone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 25]

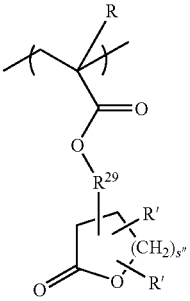 (a2-1)

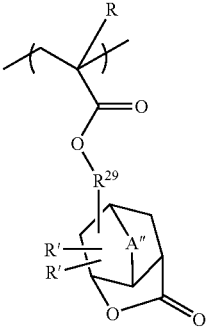 (a2-2)

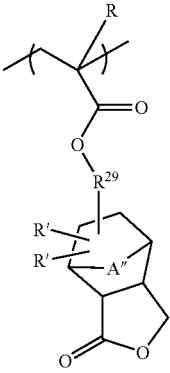 (a2-3)

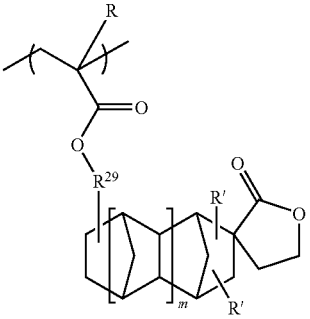 (a2-4)

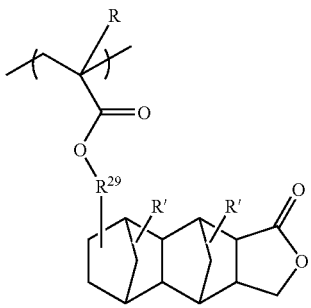
(a2-5)

In the formulas, R represents a hydrogen atom, a lower alkyl group or a halogenated lower alkyl group; each R' independently, represents a hydrogen atom, an alkyl group of 1 to 5 carbon atoms, an alkoxy group of 1 to 5 carbon atoms or —COOR", wherein R" represents a hydrogen atom or an alkyl group; $R^{29}$ represents a single bond or a divalent linking group; s" represents an integer of 0 to 2; A" represents an oxygen atom, a sulfur atom or an alkylene group of 1 to 5 carbon atoms which may contain an oxygen atom or a sulfur atom; and m represents 0 or 1.

In general formulas (a2-1) to (a2-5), R is the same as defined for R in the structural unit (a 1).

Examples of the alkyl group of 1 to 5 carbon atoms for R' include a methyl group, an ethyl group, a propyl group, an n-butyl group and a tert-butyl group.

Examples of the alkoxy group of 1 to 5 carbon atoms for R' include a methoxy group, an ethoxy group, an n-propoxy group, an iso-propoxy group, an n-butoxy group and a tert-butoxy group In terms of industrial availability, R' is preferably a hydrogen atom.

When R" is a linear or branched alkyl group, it preferably has 1 to 10 carbon atoms, more preferably 1 to 5 carbon atoms.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

As A", an alkylene group of 1 to 5 carbon atoms or —O— is preferable, more preferably an alkylene group of 1 to 5 carbon atoms, and most preferably a methylene group.

$R^{29}$ represents a single bond or a divalent linking group. Examples of divalent linking groups include the same divalent linking groups as those described above for $Y^2$ in general formula (a1-0-2). Among these, an alkylene group, an ester bond (—C(=O)—O—) or a combination thereof is preferable. The alkylene group as a divalent linking group for $R^{29}$ is preferably a linear or branched alkylene group. Specific examples include the same linear alkylene groups and branched alkylene groups as those described above for the aliphatic cyclic group A in $Y^2$.

s" is preferably 1 or 2.

Specific examples of structural units represented by general formulas (a2-1) to (a2-5) are shown below. In the formulas shown below, $R^\alpha$ represents a hydrogen atom, a methyl group or a trifluoromethyl group.

[Chemical Formula 26]

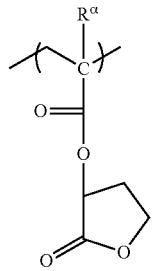
(a2-1-1)

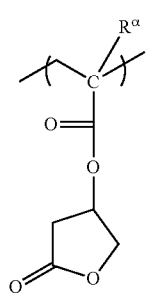
(a2-1-2)

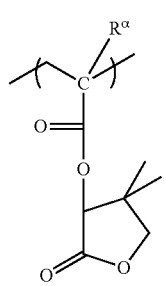
(a2-1-3)

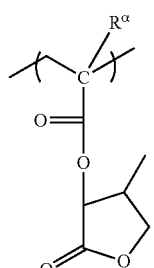
(a2-1-4)

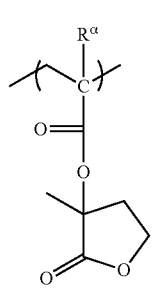
(a2-1-5)

(a2-1-6)
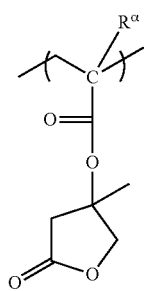
(a2-1-7)
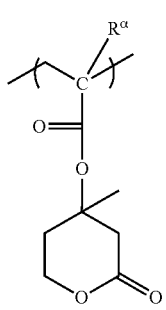
(a2-1-8)
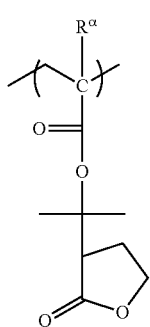
(a2-1-9)
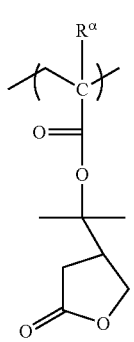
(a2-1-10)
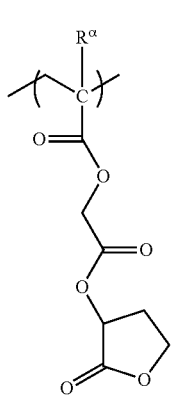
(a2-1-11)
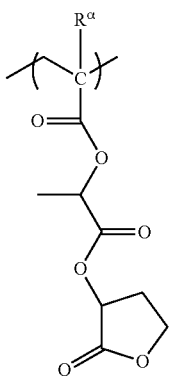
(a2-1-12)
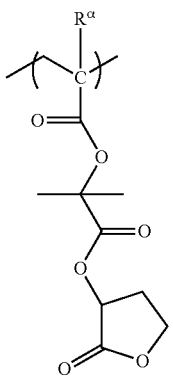
(a2-1-13)
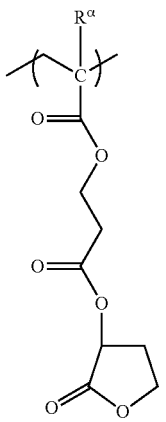
[Chemical Formula 27]
(a2-2-1)
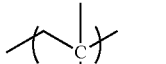

(a2-2-2)
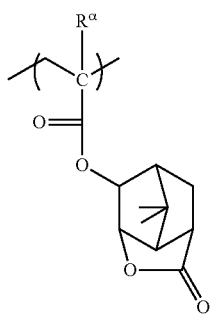
(a2-2-3)
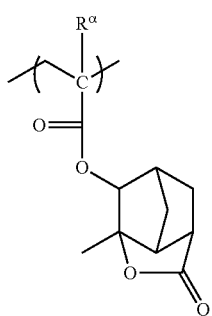
(a2-2-4)
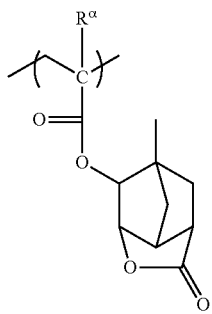
(a2-2-5)
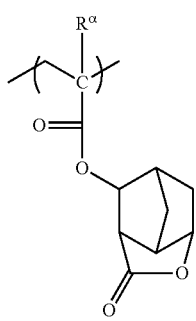
(a2-2-6)
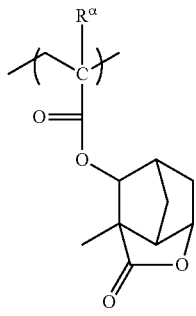
(a2-2-7)
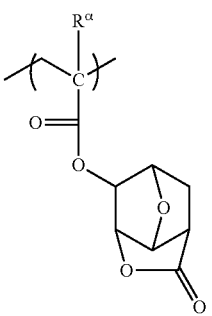
(a2-2-8)
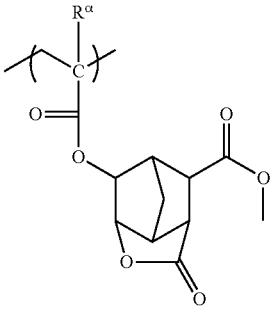
(a2-2-9)
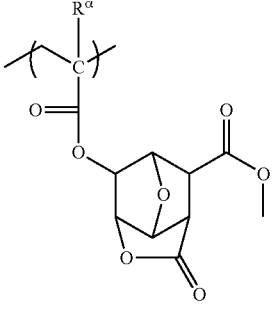
(a2-2-10)
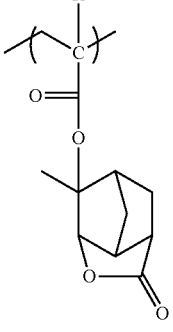
(a2-2-11)
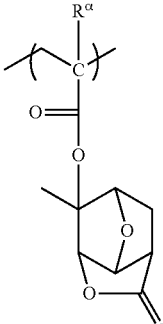

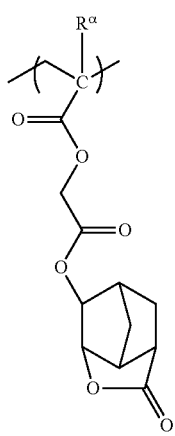 (a2-2-12)
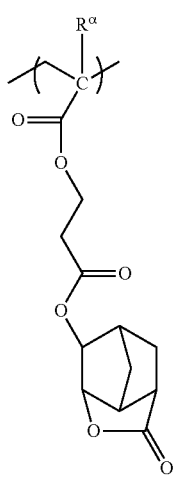 (a2-2-13)
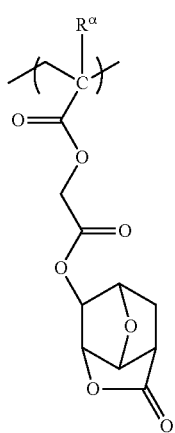 (a2-2-14)
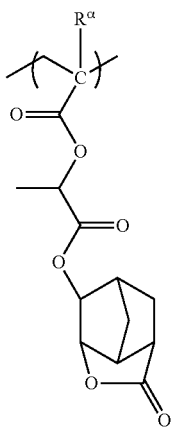 (a2-2-15)
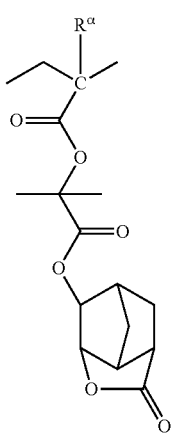 (a2-2-16)
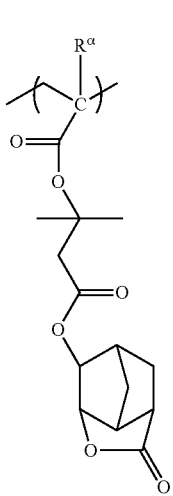 (a2-2-17)

[Chemical Formula 28]
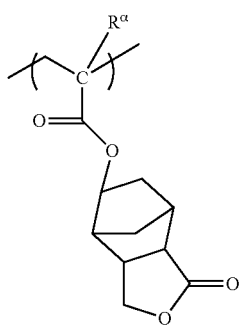 (a2-3-1)
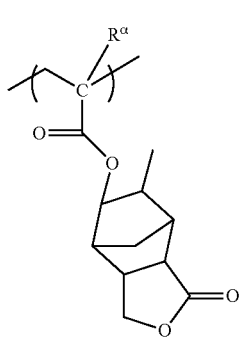 (a2-3-2)
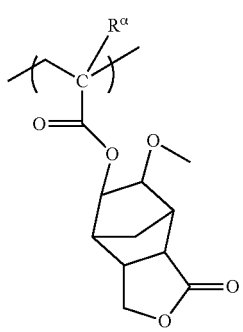 (a2-3-3)
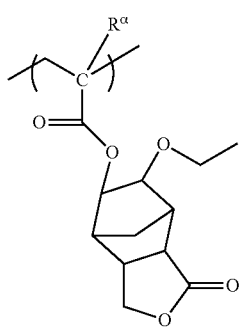 (a2-3-4)
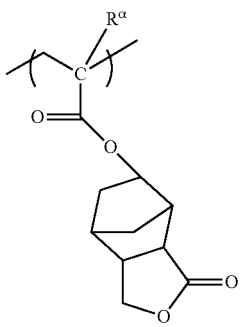 (a2-3-5)
[Chemical Formula 29]
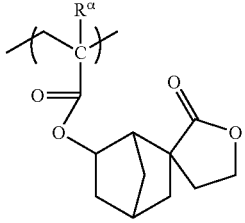 (a2-4-1)
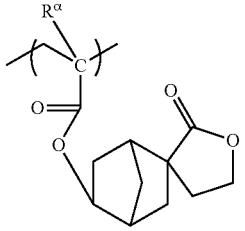 (a2-4-2)
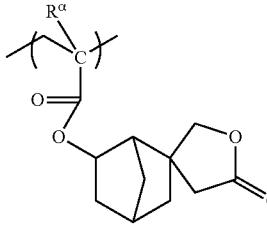 (a2-4-3)
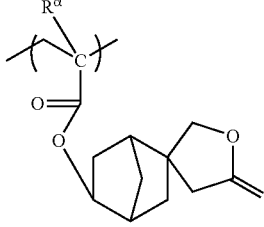 (a2-4-4)
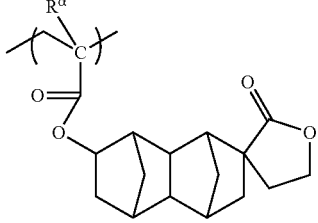 (a2-4-5)

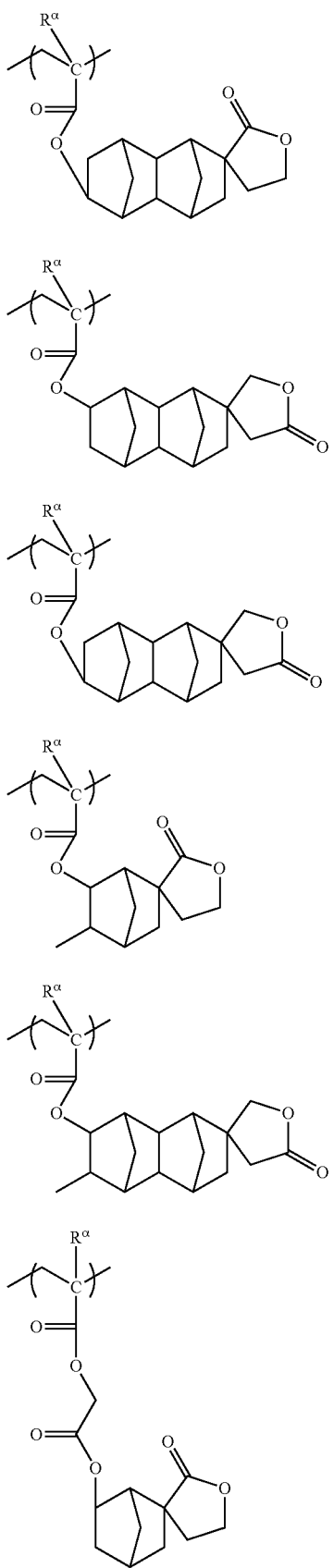
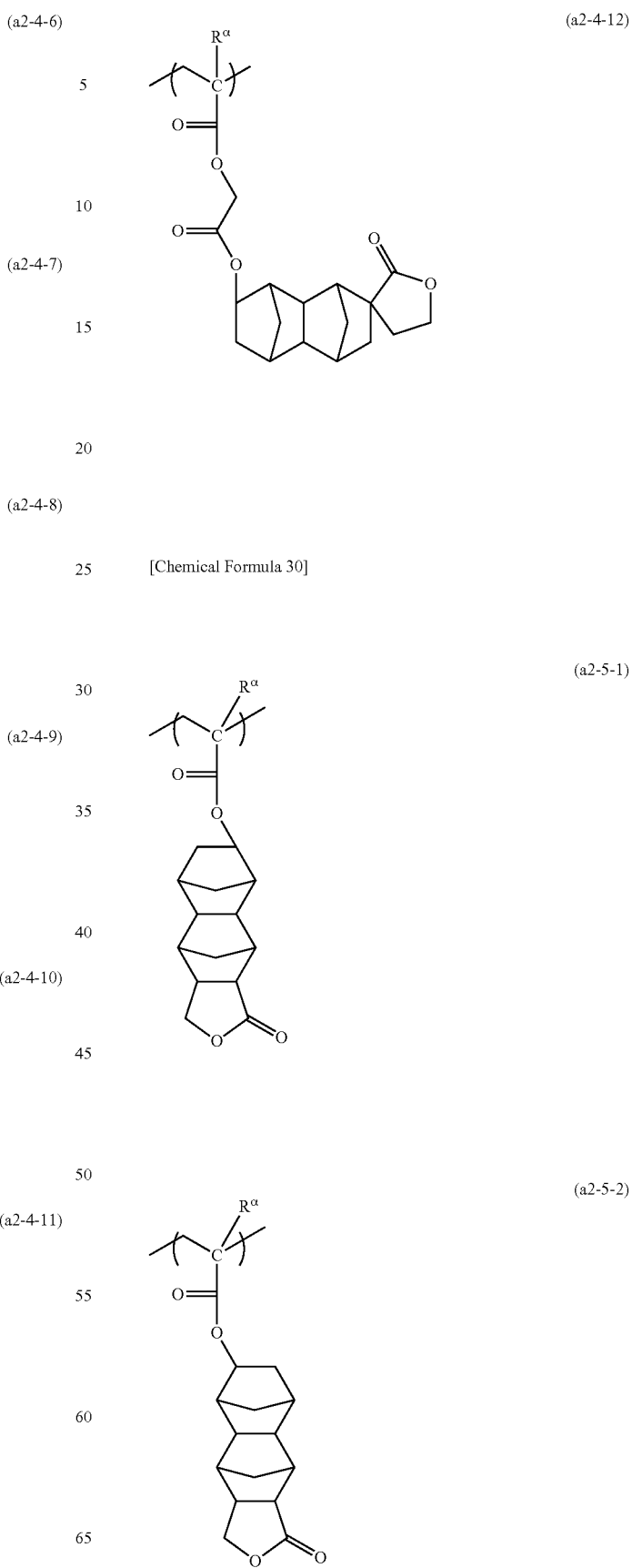

(a2-5-3) 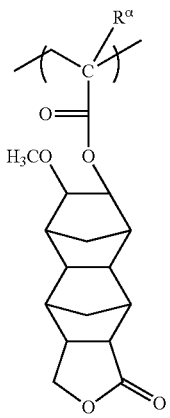

(a2-5-4) 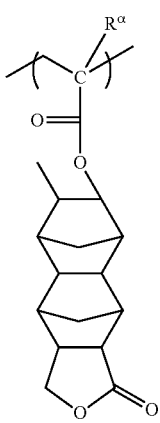

(a2-5-5) 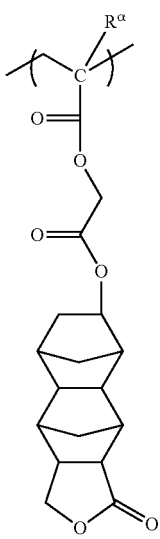

(a2-5-6) 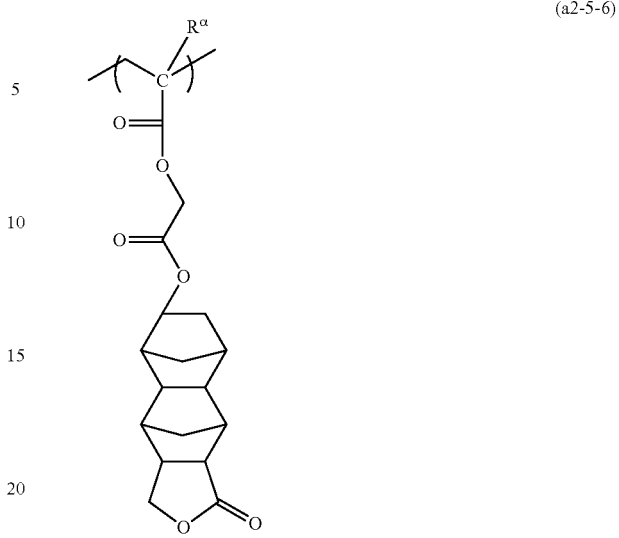

In the component (A1), as the structural unit (a2), one type of structural unit may be used, or two or more types may be used in combination.

As the structural unit (a2), at least one structural unit selected from the group consisting of formulas (a2-1) to (a2-5) is preferable, and at least one structural unit selected from the group consisting of formulas (a2-1) to (a2-3) is more preferable. Of these, it is preferable to use at least one structural unit selected from the group consisting of structural units represented by formulas (a2-1-1), (a2-2-1), (a2-2-7), (a2-3-1) and (a2-3-5).

In the component (A1), the amount of the structural unit (a2) based on the combined total of all structural units constituting the component (A1) is preferably 5 to 60 mol %, more preferably 10 to 50 mol %, and still more preferably 20 to 50 mol %. When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units.

Structural Unit (a3)

The structural unit (a3) is a structural unit derived from an acrylate ester containing a polar group-containing aliphatic hydrocarbon group.

When the component (A1) includes the structural unit (a3), the hydrophilicity of the component (A) is improved, and hence, the compatibility of the component (A) with the developing solution is improved. As a result, the alkali solubility of the exposed portions improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups).

These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of polycyclic groups include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 31]

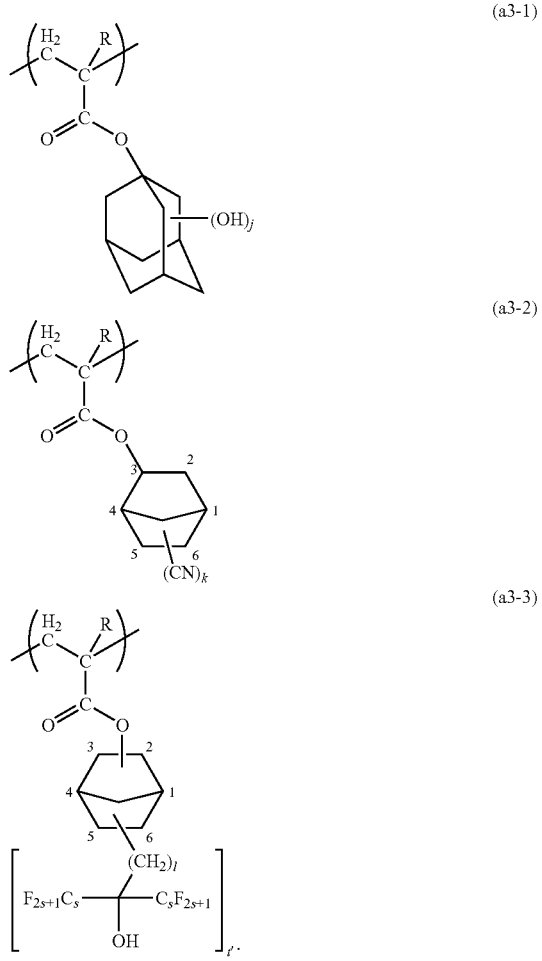

In the formulas, R is the same as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, in formula (a3-3), it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

As the structural unit (a3), one type of structural unit may be used, or two or more types may be used in combination.

In the component (A1), the amount of the structural unit (a3) based on the combined total of all structural units constituting the component (A1) is preferably 5 to 50 mol %, more preferably 5 to 40 mol %, and still more preferably 5 to 25 mol %. When the amount of the structural unit (a3) is at least as large as the lower limit of the above-mentioned range, the effect of using the structural unit (a3) can be satisfactorily achieved. On the other hand, when the amount of the structural unit (a3) is no more than the upper limit of the above-mentioned range, a good balance can be achieved with the other structural units.

Structural Unit (a4)

The component (A1) may also have a structural unit (a4) which is other than the above-mentioned structural units (a1) to (a3), as long as the effects of the present invention are not impaired.

As the structural unit (a4), any other structural unit which cannot be classified as one of the above structural units (a1) to (a3) can be used without any particular limitation, and any of the multitude of conventional structural units used within resist resins for ArF excimer lasers or KrF excimer lasers (and particularly for ArF excimer lasers) can be used.

As the structural unit (a4), a structural unit which contains a non-acid-dissociable aliphatic polycyclic group, and is also derived from an acrylate ester is preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 32]

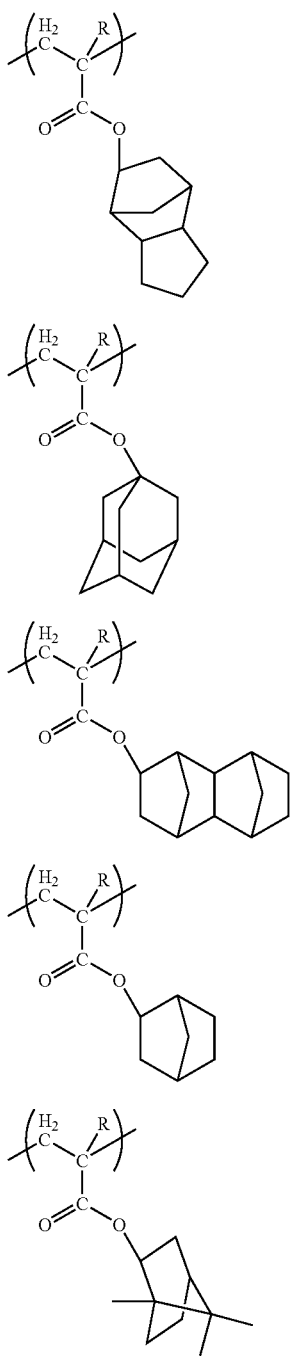

(a4-1)

(a4-2)

(a4-3)

(a4-4)

(a4-5)

In the formulas, R is the same as defined above.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

Structural Unit (a0)

The component (A1) may also have a structural unit (a0) which is other than the above-mentioned structural units (a1) to (a4), as long as the effects of the present invention are not impaired.

As the structural unit (a0), a structural unit represented by general formula (a0-1) shown below is preferable.

[Chemical Formula 33]

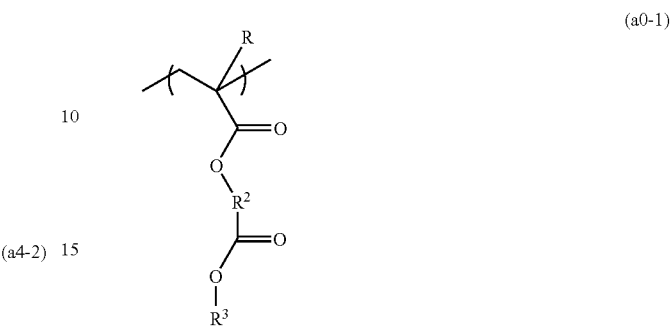

(a0-1)

In the formula, R represents a hydrogen atom, an alkyl group of 1 to 5 carbon atoms or a halogenated lower alkyl group of 1 to 5 carbon atoms; $R^2$ represents a divalent linking group; and $R^3$ represents a cyclic group which forms a ring skeleton and has a S atom of an —$SO_2$— group in the ring skeleton.

In general formula (a0-1), R represents a hydrogen atom, an alkyl group of 1 to 5 carbon atoms or a halogenated alkyl group of 1 to 5 carbon atoms.

As the alkyl group for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group.

The halogenated alkyl group for R is a group in which part or all of the hydrogen atoms of the aforementioned alkyl group has been substituted with halogen atoms. Examples of halogen atoms include fluorine atoms, chlorine atoms, bromine atoms and iodine atoms, and fluorine atoms are particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable in terms of industrial availability.

In general formula (a0-2), $R^2$ represents a divalent linkage group.

Preferable examples of $R^2$ include a divalent hydrocarbon group which may have a substituent, and a divalent linkage group containing a hetero atom.

Divalent Hydrocarbon Group which May have a Substituent

With respect to $R^2$, the hydrocarbon group "has a substituent" means that part or all of the hydrogen atoms within the hydrocarbon group has been substituted with a group or an atom other than a hydrogen atom.

The hydrocarbon group may be either an aliphatic hydrocarbon group or an aromatic hydrocarbon group. An "aliphatic hydrocarbon group" refers to a hydrocarbon group that has no aromaticity.

The aliphatic hydrocarbon group may be saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear or branched aliphatic hydrocarbon group preferably has 1 to 10 carbon atoms, more preferably 1 to 8, still more preferably 2 to 5, and most preferably 2.

As the linear aliphatic hydrocarbon group, a linear alkylene group is preferable. Specific examples thereof include a methylene group [—$CH_r$], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of substituents include a fluorine atom, a fluorinated alkyl group of 1 to 5 carbon atoms, and an oxygen atom (=O).

As examples of the hydrocarbon group containing a ring in the structure thereof, a cyclic aliphatic hydrocarbon group (a group in which two hydrogen atoms have been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group.

As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent.

Examples of the substituent include an alkyl group of 1 to 5 carbon atoms, a fluorine atom, a fluorinated alkyl group of 1 to 5 carbon atoms, and an oxygen atom (=O).

Examples of the aforementioned aromatic hydrocarbon group include a divalent aromatic hydrocarbon group in which one hydrogen atom has been removed from a benzene ring of a monovalent aromatic hydrocarbon group such as a phenyl group, a biphenyl group, a fluorenyl group, a naphthyl group, an anthryl group or a phenanthryl group; an aromatic hydrocarbon group in which part of the carbon atoms constituting the ring of the aforementioned divalent aromatic hydrocarbon group has been substituted with a hetero atom such as an oxygen atom, a sulfur atom or a nitrogen atom; and an aromatic hydrocarbon group in which one hydrogen atom has been removed from a benzene ring of an arylalkyl group such as a benzyl group, a phenethyl group, a 1-naphthylmethyl group, a 2-naphthylmethyl group, a 1-naphthylethyl group or a 2-naphthylethyl group.

The aromatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O).

Divalent Linkage Group Containing a Hetero Atom

With respect to the "divalent linkage group containing a hetero atom" for $R^2$, a hetero atom refers to an atom other than a carbon atom and a hydrogen atom, and examples thereof include an oxygen atom, a nitrogen atom, a sulfur atom and a halogen atom.

Specific examples of the divalent linking group containing a hetero atom include —O—, —C(=O)—, —C(=O)—O—, a carbonate bond (—O—C(=O)—O—), —NH—, —$NR^{04}$— ($R^{04}$ represents a substituent such as an alkyl group or an acyl group), —NH—C(=O)—, =N—, —S—, —$S(=O)_2$—, and —$S(=O)_2$—O—. Further, a combination of any one of these "divalent linkage groups containing a hetero atom" with a divalent hydrocarbon group can also be used. As examples of the divalent hydrocarbon group, the same groups as those described above for the hydrocarbon group which may have a substituent can be given, and a linear or branched aliphatic hydrocarbon group is preferable.

In the —$NR^{04}$— group, $R^{04}$ represents a substituent such as an alkyl group or an acyl group. The substituent (an alkyl group, an acyl group or the like) preferably has 1 to 10 carbon atoms, more preferably 1 to 8, and most preferably 1 to 5.

$R^2$ may or may not have an acid dissociable portion in the structure thereof.

An "acid dissociable portion" refers to a portion within the $R^2$ group which is dissociated from the group by action of acid generated upon exposure. When $R^2$ group has an acid dissociable portion, it preferably has an acid dissociable portion having a tertiary carbon atom.

In the present invention, as the divalent linking group for $R^2$, an alkylene group, a divalent aliphatic cyclic group or a divalent linkage group containing a hetero atom is preferable. Among these, an alkylene group is particularly desirable.

When $R^2$ represents an alkylene group, it preferably has 1 to 10 carbon atoms, more preferably 1 to 6, still more preferably 1 to 4, and most preferably 1 to 3. Specific examples of alkylene groups include the aforementioned linear alkylene groups and branched alkylene groups.

When $R^2$ represents a divalent aliphatic cyclic group, as the aliphatic cyclic group, the same aliphatic cyclic groups as those described above for the "aliphatic hydrocarbon group containing a ring in the structure thereof" can be used.

As the aliphatic cyclic group, a group in which two hydrogen atoms have been removed from cyclopentane, cyclohexane, norbornane, isobornane, adamantane, tricyclodecane or tetracyclododecane is particularly desirable.

When $R^2$ represents a divalent linking group containing a hetero, atom, preferable examples of the divalent linking groups containing a hetero atom include —O—, —C(=O)—O—, —C(=O)—, —O—C(=O)—O—, —C(=O)—NH—, —$NR^{04}$—($R^{04}$ represents a substituent such as an alkyl group or an acyl group), —S—, —$S(=O)_2$—, —$S(=O)_2$—O—, a group represented by the formula -A-O—B—, and a group represented by the formula -[A-C(=O)—O]$_q$—B—. Herein, each of A and B independently represents a divalent hydrocarbon group which may have a substituent, and q represents an integer of 0 to 3.

In the group represented by the formula -A-O—B— or -[A-C(=O)—O]$_q$—B—, each of A and B independently represents a divalent hydrocarbon group which may have a substituent.

Examples of divalent hydrocarbon groups for A and B which may have a substituent include the same groups as those described above for the "divalent hydrocarbon group which may have a substituent" usable as $R^2$.

As A, a linear aliphatic hydrocarbon group is preferable, more preferably a linear alkylene group, still more preferably a linear alkylene group of 1 to 5 carbon atoms, and a methylene group or an ethylene group is particularly desirable.

As B, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula -[A-C(=O)—O]$_q$—B—, q represents an integer of 0 to 3, preferably an integer of 0 to 2, more preferably 0 or 1, and most preferably 1.

In general formula (a0-1), $R^3$ represents a cyclic group which forms a ring skeleton and has a S atom of an —SO$_2$— group in the ring skeleton.

The cyclic group for $R^3$ refers to a cyclic group including a ring that contains a S atom of an —SO$_2$— group in the ring skeleton thereof, and this ring is counted as the first ring. A cyclic group in which the only ring structure is the ring that contains —SO$_2$— in the ring skeleton thereof is referred to as a monocyclic group, and a group containing other ring structures is described as a polycyclic group regardless of the structure of the other rings. The cyclic group for $R^3$ may be either a monocyclic group or a polycyclic group.

As $R^3$, a cyclic group containing —O—SO$_2$— within the ring skeleton thereof, i.e., a sultone ring is particularly desirable.

The cyclic group for $R^3$ preferably has 3 to 30 carbon atoms, more preferably 4 to 20, still more preferably 4 to 15, and most preferably 4 to 12.

Herein, the number of carbon atoms refers to the number of carbon atoms constituting the ring skeleton, excluding the number of carbon atoms within a substituent.

The cyclic group for $R^3$ may be either an aliphatic cyclic group or an aromatic cyclic group, and is preferably an aliphatic cyclic group.

Examples of aliphatic cyclic groups for $R^3$ include the aforementioned cyclic aliphatic hydrocarbon groups in which a part of the carbon atoms constituting the ring skeleton thereof has been substituted with —SO$_2$— or —O—SO$_2$—.

More specifically, examples of monocyclic groups include a monocycloalkane in which one hydrogen atom have been removed therefrom and a —CH$_2$— group constituting the ring skeleton thereof has been substituted with —SO$_2$—; and a monocycloalkane in which one hydrogen atom have been removed therefrom and a —CH$_2$—CH$_2$— group constituting the ring skeleton thereof has been substituted with —O—SO$_2$—. Examples of polycyclic groups include a polycycloalkane (a bicycloalkane, a tricycloalkane, a tetracycloalkane or the like) in which one hydrogen atom have been removed therefrom and a —CH$_2$— group constituting the ring skeleton thereof has been substituted with —SO$_2$—; and a polycycloalkane in which one hydrogen atom have been removed therefrom and a —CH$_2$—CH$_2$— group constituting the ring skeleton thereof has been substituted with —O—SO$_2$—.

The cyclic group for $R^3$ may have a substituent. Examples of substituents include an alkyl group, an alkoxy group, a halogen atom, a halogenated alkyl group, a hydroxy group, an oxygen atom (=O), —COOR'', —OC(=O)R'', a hydroxyalkyl group and a cyano group. R'' represents a hydrogen atom or an alkyl group.

The alkyl group for the substituent is preferably an alkyl group of 1 to 6 carbon atoms. Further, the alkyl group is preferably a linear alkyl group or a branched alkyl group. Specific examples include a methyl group, ethyl group, propyl group, isopropyl group, n-butyl group, isobutyl group, tert-butyl group, pentyl group, isopentyl group, neopentyl group and hexyl group. Among these, a methyl group or ethyl group is preferable, and a methyl group is particularly desirable.

As the alkoxy group for the substituent, an alkoxy group of 1 to 6 carbon atoms is preferable. Further, the alkoxy group is preferably a linear alkoxy group or a branched alkyl group. Specific examples of the alkoxy groups include the aforementioned alkyl groups for the substituent having an oxygen atom (—O—) bonded thereto.

Examples of halogen atoms for the substituent include a fluorine atom, a chlorine atom, a bromine atom and an iodine atom, and a fluorine atom is preferable.

Examples of halogenated alkyl groups for the substituent include groups in which part or all of the hydrogen atoms within the aforementioned alkyl groups has been substituted with the aforementioned halogen atoms.

As examples of the halogenated lower alkyl group for the substituent, groups in which part or all of the hydrogen atoms of the aforementioned alkyl groups for the substituent have been substituted with the aforementioned halogen atoms can be given. As the halogenated alkyl group, a fluorinated alkyl group is preferable, and a perfluoroalkyl group is particularly desirable.

In the —COOR'' group and the —OC(=O)R'' group, R'' preferably represents a hydrogen atom or a linear, branched or cyclic alkyl group of 1 to 15 carbon atoms.

When R'' represents a linear or branched alkyl group, it is preferably an alkyl group of 1 to 10 carbon atoms, more preferably an alkyl group of 1 to 5 carbon atoms, and most preferably a methyl group or an ethyl group.

When R'' is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

The hydroxyalkyl group for the substituent preferably has 1 to 6 carbon atoms, and specific examples thereof include the aforementioned alkyl groups for the substituent in which at least one hydrogen atom has been substituted with a hydroxy group.

More specific examples of $R^3$ include groups represented by general formulas (3-1) to (3-4) shown below.

[Chemical Formula 34]

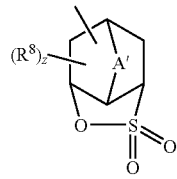
(3-1)

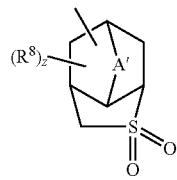
(3-2)

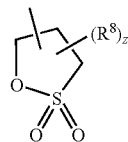
(3-3)

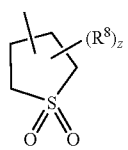
(3-4)

In the formulas, A' represents an alkylene group of 1 to 5 carbon atoms which may contain an oxygen atom or a sulfur atom, an oxygen atom, or a sulfur atom; z represents an integer of 0 to 2; and $R^8$ represents an alkyl group, an alkoxy group, a halogenated alkyl group, a hydroxyl group, —COOR", —OC(=O)R", a hydroxyalkyl group or a cyano group, wherein R" represents a hydrogen atom or an alkyl group.

In general formulas (3-1) to (3-4) above, A' represents an alkylene group of 1 to 5 carbon atoms which may contain an oxygen atom (—O—) or a sulfur atom (—S—), an oxygen atom, or a sulfur atom.

As the alkylene group of 1 to 5 carbon atoms for A', a linear or branched alkylene group is preferable, and examples thereof include a methylene group, an ethylene group, an n-propylene group and an isopropylene group.

Examples of alkylene groups that contain an oxygen atom or a sulfur atom include the aforementioned alkylene groups in which —O— or —S— is bonded to the terminal of the alkylene group or interposed within the alkyl group. Specific examples of such alkylene groups include —O—CH$_2$—, —CH$_2$—O—CH$_2$—, —S—CH$_2$—, —CH$_2$—S—CH$_2$—.

As A', an alkylene group of 1 to 5 carbon atoms or —O— is preferable, more preferably an alkylene group of 1 to 5 carbon atoms, and most preferably a methylene group.

z represents an integer of 0 to 2, and is most preferably 0.

When z is 2, the plurality of $R^8$ may be the same or different from each other.

As the alkyl group, alkoxy group, halogenated alkyl group, halogenated alkyl group, hydroxyl group, —COOR", —OC(=O)R", hydroxyalkyl group and cyano group for $R^8$, the same alkyl groups, alkoxy groups, halogenated alkyl groups, halogenated alkyl groups, hydroxyl groups, —COOR", —OC(=O)R", hydroxyalkyl groups and cyano groups as those described above as the substituent which the cyclic group for $R^3$ may have can be used.

Specific examples of the cyclic groups represented by general formulas (3-1) to (3-4) are shown below. In the formulas shown below, "Ac" represents an acetyl group.

[Chemical Formula 35]

(3-1-1)

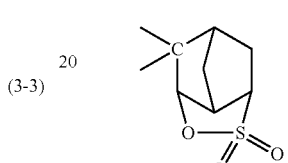
(3-1-2)

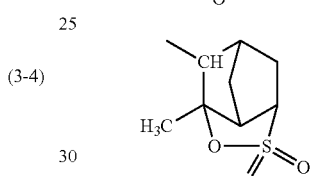
(3-1-3)

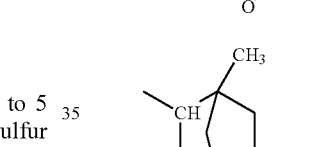
(3-1-4)

(3-1-5)

(3-1-6)

(3-1-7)

-continued
(3-1-8)
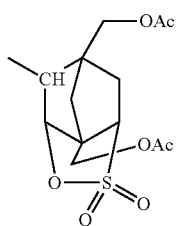
[Chemical Formula 36]
(3-1-9)
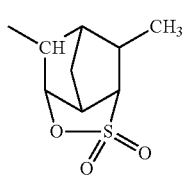
(3-1-10)
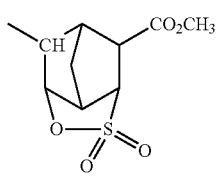
(3-1-11)
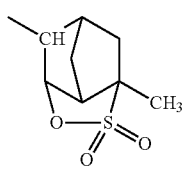
(3-1-12)
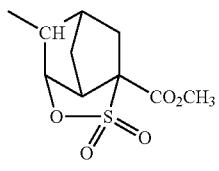
(3-1-13)
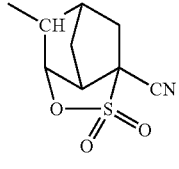
(3-1-14)
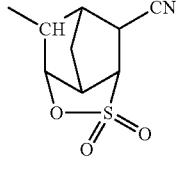
(3-1-15)
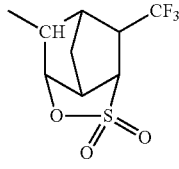
(3-1-16)
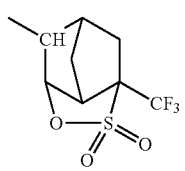
(3-1-17)
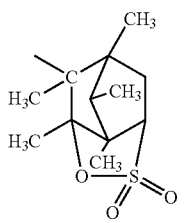
[Chemical Formula 37]
(3-1-18)
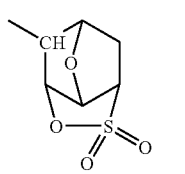
(3-1-19)
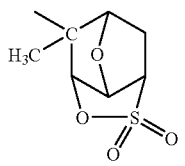
(3-1-20)
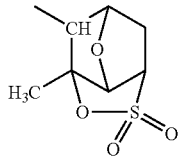
(3-1-21)
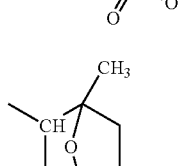
(3-1-22)
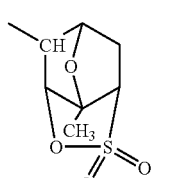
(3-1-23)
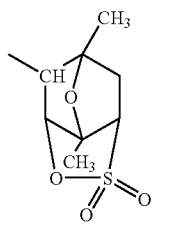

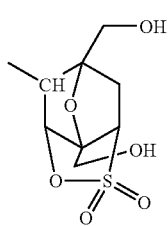 (3-1-24)
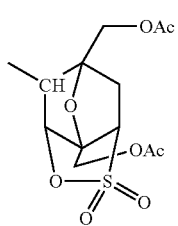 (3-1-25)
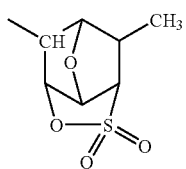 (3-1-26)
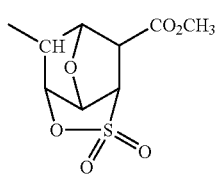 (3-1-27)
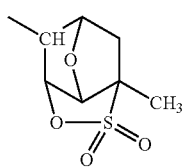 (3-1-28)
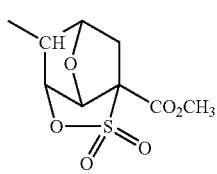 (3-1-29)
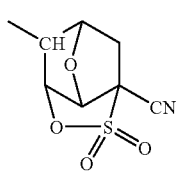 (3-1-30)
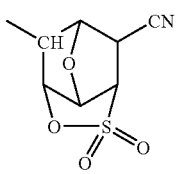 (3-1-31)
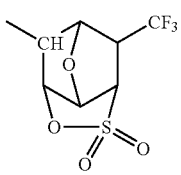 (3-1-32)
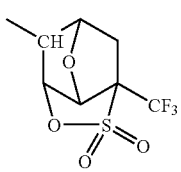 (3-1-33)
[Chemical Formula 38]
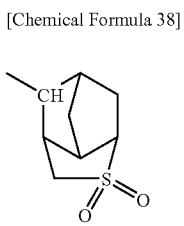 (3-2-1)
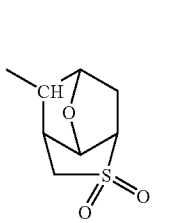 (3-2-2)
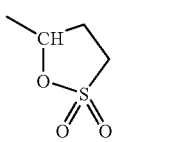 (3-3-1)
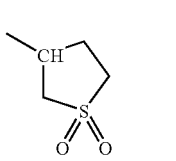 (3-4-1)

Among the examples shown above, as $R^3$, a cyclic group represented by general formula (3-1), (3-3) or (3-4) above is preferable, and a cyclic group represented by general formula (3-1) above is particularly desirable.

More specifically, as $R^3$, it is preferable to use at least one cyclic group selected from the group consisting of cyclic groups represented by chemical formulas (3-1-1), (3-1-18), (3-3-1) and (3-4-1) above, and a cyclic group represented by chemical formula (3-1-1) above is particularly desirable.

In the present invention, as the structural unit (a0), a structural unit represented by general formula (a0-1-11) shown below is particularly desirable.

[Chemical Formula 39]

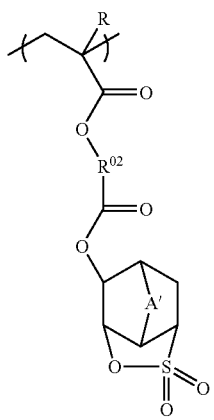

(a0-1-11)

In the formula, R is the same as defined above; $R^{02}$ represents a linear or branched alkylene group or -A-C(=O)—O—B— (wherein A and B are as defined above); and A' is the same as defined above.

The linear or branched alkylene group for $R^{02}$ preferably has 1 to 10 carbon atoms, more preferably 1 to 8, still more preferably 1 to 5, still more preferably 1 to 3, and most preferably 1 or 2.

In the -A-C(=O)—O—B— group, each of A and B preferably represents a linear or branched alkylene group, more preferably an alkylene group of 1 to 5 carbon atoms, and most preferably a methylene group or an ethylene group. Specific examples of A and B include —(CH$_2$)$_2$—C(=O)—O—(CH$_2$)$_2$—, and —(CH$_2$)$_2$—O—C(=O)—(CH$_2$)$_2$—.

A' is preferably a methylene group, an oxygen atom (—O—) or a sulfur atom (—S—).

As the structural unit (a0), one type of structural unit may be used alone, or two or more types of structural units may be used in combination.

In terms of achieving excellent lithography properties such as exposure margin (EL margin), line width roughness (LWR) and the like in the formation of a resist pattern using a positive resist composition containing the component (A1), the amount of the structural unit (a0) within the component (A1), based on the combined total of all structural units constituting the component (A1) is preferably 1 to 60 mol %, more preferably 5 to 55 mol %, still more preferably 10 to 50 mol %, and most preferably 15 to 45 mol %.

As a monomer for deriving the structural unit (a0), a compound represented by general formula (a0-1-0) shown below (hereafter, referred to as "compound (a0-1-0)") can be used.

[Chemical Formula 40]

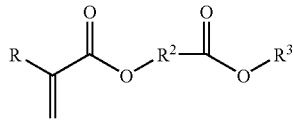

(a0-1-0)

In general formula (a0-1-0), R, $R^2$ and $R^3$ are the same as defined above.

The method for producing the compound (a0-1-0) is not particularly limited, and the compound (a0-1-0) can be produced by a conventional method.

For example, in the presence of a base, a compound (X-6) represented by general formula (X-6) shown below is added to a solution obtained by dissolving a compound (X-5) represented by general formula (X-5) shown below in a reaction solvent, and a reaction is effected to thereby obtain a compound (a0-1-0).

Examples of the base include inorganic bases such as sodium hydride, $K_2CO_3$ and $Cs_2CO_3$; and organic bases such as triethylamine, 4-dimethylaminopyridine (DMAP) and pyridine. Examples of condensing agents include carbodiimide reagents such as ethyldiisopropylaminocarbodiimide hydrochloride (EDCI), dicyclohexylcarboxylmide (DCC), diisopropylcarbodiimide and carbodiimidazole; tetraethyl pyrophosphate; and benzotriazole-N-hydroxytrisdimethylaminophosphonium hexafluorophosphide (Bop reagent).

If desired, an acid may be used. As the acid, any acid generally used for dehydration/condensation may be used. Specific examples include inorganic acids such as hydrochloric acid, sulfuric acid and phosphoric acid; and organic acids such as methanesulfonic acid, trifluoromethanesulfonic acid, benzenesulfonic acid and p-toluenesulfonic acid. These acids can be used individually, or in a combination of two or more.

[Chemical Formula 41]

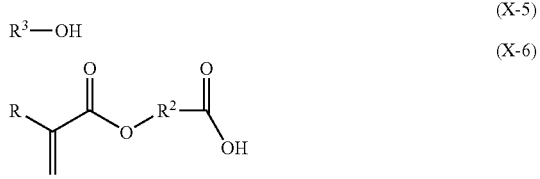

In the present invention, the component (A) is preferably a polymer having the structural unit (a1).

Examples of such a polymer include a copolymer having the structural units (a1) and (a2), a copolymer having the structural units (a1) and (a3), and a copolymer having the structural units (a1), (a2) and (a3). Specific examples include a copolymer consisting of the structural units (a1), (a2) and (a3), a copolymer consisting of the structural units (a1), (a2), (a3) and (a4), and a copolymer consisting of the structural units (a1), (a2), (a3) and (a0).

In the component (A), as the component (A1), one type may be used alone, or two or more types may be used in combination.

In the present invention, as the component (A1), a polymeric compound that includes a combination of structural units such as that shown below is particularly desirable.

[Chemical Formula 42]

(A1-11)

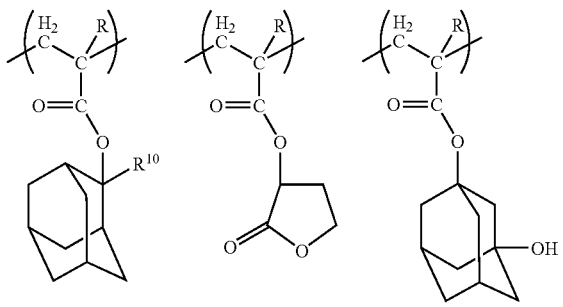

In the formula, R is the same as defined above, and the plurality of R may be either the same or different from each other; and $R^{10}$ represents a lower alkyl group.

In formula (A1-11), the lower alkyl group for $R^{10}$ is the same as the lower alkyl group for R above, preferably a methyl group or an ethyl group, and most preferably a methyl group.

[Chemical Formula 43]

(A1-12)

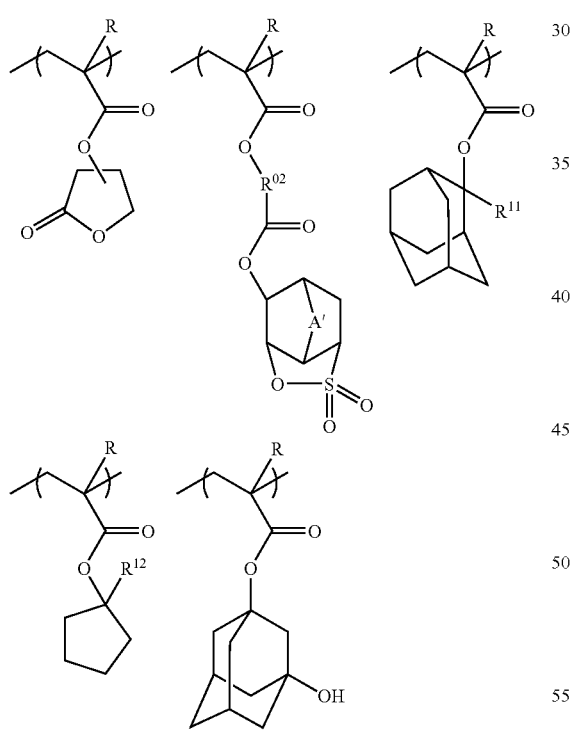

In the formula, R, $R^{02}$, A', $R^{11}$ and $R^{12}$ are the same as defined above; and the plurality of R may be the same or different from each other.

In formula (A1-12), $R^{11}$ is preferably a linear or branched alkyl group, more preferably a branched alkyl group, and most preferably an isopropyl group.

The alkyl group for $R^{12}$ is the same as defined for the alkyl group for R, preferably a methyl group or an ethyl group, and most preferably a methyl group.

$R^{02}$ is the same as defined for $R^{02}$ in general formula (a0-1-11), and is preferably a linear alkylene group, more preferably an alkylene group of 1 to 10 carbon atoms, and most preferably an alkylene group of 1 or 2 carbon atoms.

A' is the same as defined for A' in general formula (a0-1-11), and is preferably an oxygen atom, a methylene group or an ethylene group.

[Chemical Formula 44]

(A1-13)

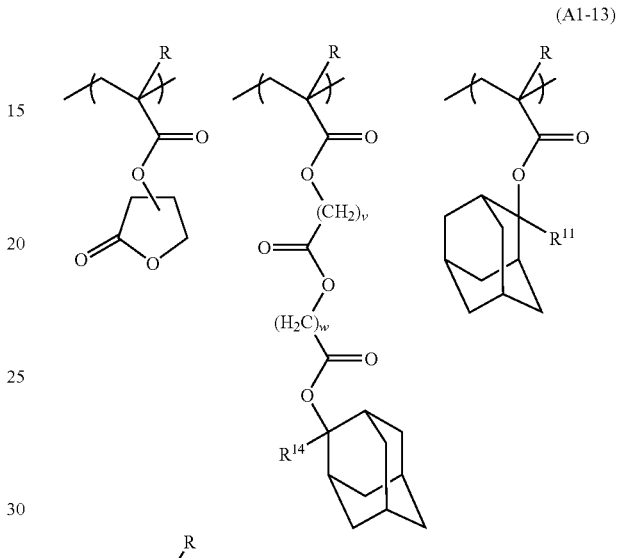

In the formula, R, $R^{14}$, v, w and $R^{11}$ are the same as defined above; and the plurality of R may be the same or different from each other.

In formula (A1-13), $R^{11}$ is preferably a linear or branched alkyl group. A linear alkyl group is more preferable, a methyl group or an ethyl group is still more preferable, and an ethyl group is most preferable.

The alkyl group for $R^{14}$ is the same as defined for the alkyl group for R, preferably a methyl group or an ethyl group, and most preferably a methyl group.

v is preferably an integer of 1 to 5, more preferably 1 or 2, and most preferably 1.

w is preferably an integer of 1 to 5, more preferably 1 or 2, and most preferably 1.

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

As the monomers for deriving the corresponding structural units, commercially available monomers may be used, or the monomers may be synthesized by a conventional method.

The weight average molecular weight (Mw) (the polystyrene equivalent value determined by gel permeation chromatography) of the component (A1) is not particularly limited, but is preferably 2,000 to 50,000, more preferably 3,000 to 30,000, and most preferably 5,000 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (A1) is not particularly limited, but is preferably 1.0 to 5.0, more preferably 1.0 to 3.0, and most preferably 1.2 to 2.5.

Here, Mn is the number average molecular weight.

In the component (A), the amount of the component (A1) based on the total weight of the component (A) is preferably 25% by weight or more, more preferably 50% by weight or more, still more preferably 75% by weight or more, and may be even 100% by weight. When the amount is 25% by weight or more, a resist pattern having an excellent shape can be obtained, and lithography properties are improved.

[Component (A2)]

As the component (A2), it is preferable to use a compound that has a molecular weight of at least 500 and less than 2,000, contains a hydrophilic group, and also contains an acid dissociable, dissolution inhibiting group described above in connection with the component (A1). Specific examples include compounds containing a plurality of phenol skeletons in which a part of the hydrogen atoms within hydroxyl groups have been substituted with the aforementioned acid dissociable, dissolution inhibiting groups.

Examples of the component (A2) include low molecular weight phenolic compounds in which a portion of the hydroxyl group hydrogen atoms have been substituted with an aforementioned acid dissociable, dissolution inhibiting group, and these types of compounds are known, for example, as sensitizers or heat resistance improvers for use in non-chemically amplified g-line or i-line resists.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers and tetramers of formalin condensation products of phenols such as phenol, m-cresol, p-cresol and xylenol. Needless to say, the low molecular weight phenol compound is not limited to these examples.

Also, there are no particular limitations on the acid dissociable, dissolution inhibiting group, and suitable examples include the groups described above.

As the component (A2), one type of resin may be used, or two or more types of resins may be used in combination.

In the resist composition of the present invention, as the component (A), one type may be used, or two or more types of compounds may be used in combination.

Of the examples shown above, as the component (A), it is preferable to use one containing the component (A1).

In the resist composition of the present invention, the amount of the component (A) can be appropriately adjusted depending on the thickness of the resist film to be formed, and the like.

<Component (B)>

[Component (B1)]

The resist composition of the present invention contains an acid-generator component (B) which generates acid upon exposure, and the component (B) includes an acid generator (B1) (hereafter, referred to as "component (B1)") containing a compound having a cation moiety comprising a group represented by general formula (I) shown below.

[Chemical Formula 45]

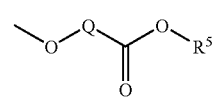

(I)

In formula (I), $R^5$ represents an organic group having a carbonyl group, an ester bond or a sulfonyl group; and Q represents a divalent linking group.

In formula (I), $R^5$ represents an organic group having a carbonyl group, an ester bond or a sulfonyl group.

In general formula (I), the organic group for $R^5$ may be either an aromatic hydrocarbon group or an aliphatic hydrocarbon group.

Examples of the aliphatic hydrocarbon group for $R^5$ include a linear, branched or cyclic, saturated hydrocarbon group, and a linear or branched, unsaturated aliphatic hydrocarbon group.

The linear or branched, saturated hydrocarbon group preferably has 3 to 15 carbon atoms, and more preferably 5 to 12 carbon atoms.

The linear or branched, unsaturated aliphatic hydrocarbon group preferably has 2 to 5 carbon atoms.

When $R^5$ represents any of these chain-like (linear or branched) hydrocarbon groups, examples thereof include groups which have a carbonyl group, an ester bond or a sulfonyl group between carbon atoms constituting the carbon chain.

The aforementioned linear or branched, saturated or unsaturated hydrocarbon group may have a substituent. Examples of the substituent include an alkoxy group, a halogen atom, a halogenated alkyl group, a hydroxyl group and a cyano group. Further, the saturated hydrocarbon group or the unsaturated, aliphatic hydrocarbon group may contain an ester group.

The aforementioned alkoxy group as a substituent is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of halogen atoms for the substituent include a fluorine atom, a chlorine atom, a bromine atom and an iodine atom, and a fluorine atom is preferable.

Examples of the halogenated alkyl group as a substituent include groups in which part or all of the hydrogen atoms within an alkyl group of 1 to 5 carbon atoms (preferably a methyl group, an ethyl group, a propyl group, an n-butyl group, a tert-butyl group, or the like) have been substituted with the aforementioned halogen atoms.

The cyclic, saturated hydrocarbon group for $R^5$ may be either a polycyclic group or a monocyclic group. Examples thereof include cyclic, saturated hydrocarbon groups of 3 to 20 carbon atoms, such as groups in which one hydrogen atom has been removed from a monocycloalkane, or a polycycloalkane including a bicycloalkane, tricycloalkane and tetracycloalkane. More specific examples include groups in which one hydrogen atom has been removed from a monocycloalkane such as cyclopentane, cyclohexane, cycloheptane or cyclooctane; and groups in which one hydrogen atom has been removed from a polycycloalkane such as adamantane, norbornane, isobornane, tricyclodecane or tetracyclododecane.

When $R^5$ represents any of these cyclic, saturated hydrocarbon groups, preferable examples thereof include groups in which part of the carbon atoms constituting the ring of the aforementioned monocycloalkane or polycycloalkane has been substituted with an oxygen atom or a sulfur atom, so as to have an ester bond or a sulfonyl group. More specific examples include a lactone-containing monocyclic group, such as a group in which one hydrogen atom has been removed from γ-butyrolactone; a lactone-containing polycyclic group, such as a group in which one hydrogen atom has been removed from a bicycloalkane, tricycloalkane or tetracycloalkane containing a lactone ring; and a cyclic group containing —O—$SO_2$— within the ring skeleton thereof (i.e., sultone ring). Further, the aforementioned cyclic, saturated hydrocarbon group in which a hydrogen atom bonded to a ring thereof has been substituted with an oxygen atom (=O) (so as to form a carbonyl group) can also be given as a preferable example.

The cyclic, saturated hydrocarbon group may have a substituent other than a carbonyl group, an ester bond and a sulfonyl group. For example, part of the carbon atoms constituting the ring within the cyclic, saturated hydrocarbon group may be substituted with a hetero atom, or a hydrogen atom bonded to the ring within the cyclic, saturated hydrocarbon group may be substituted with a substituent.

In the former example, a heterocycloalkane in which part of the carbon atoms constituting the ring within the aforementioned monocycloalkane or polycycloalkane has been substituted with a nitrogen atom, and one hydrogen atom has been removed therefrom, can be used.

In the latter example, as the substituent for the cyclic alkyl group, an alkyl group of 1 to 5 carbon atoms, an alkoxy group, a halogen atom, a halogenated alkyl group, a hydroxyl group, a cyano group or the like can be used. As the alkoxy group, halogen atom and halogenated alkyl group for the substituent, the same groups as those described above as the substituent for the aforementioned linear or branched, saturated hydrocarbon group can be mentioned.

The aromatic hydrocarbon group for $R^5$ is a hydrocarbon group having an aromatic ring. For example, the aromatic hydrocarbon group may be a group consisting of an aromatic ring, or an alkylene group having an aromatic ring bonded to one terminal thereof.

The aromatic hydrocarbon ring preferably has 3 to 30 carbon atoms, more preferably 5 to 30, still more preferably 5 to 20, still more preferably 6 to 15, and most preferably 6 to 12. Here, the number of carbon atoms within a substituent(s) is not included in the number of carbon atoms of the aromatic hydrocarbon group.

The aromatic hydrocarbon group may be either a group including an aromatic hydrocarbon ring in which the ring skeleton of the aromatic ring is constituted of only carbon atoms, or a group including an aromatic hetero ring in which the ring skeleton of the aromatic ring contains not only carbon atoms but also a hetero atom.

Examples of the aromatic hydrocarbon group include an aryl group which is an aromatic hydrocarbon ring having one hydrogen atom removed therefrom, such as a phenyl group, a biphenyl group, a fluorenyl group, a naphthyl group, an anthryl group or a phenanthryl group; a heteroaryl group in which a part of the carbon atoms constituting the aforementioned aryl group has been substituted with a hetero atom such as an oxygen atom, a sulfur atom or a nitrogen atom; and an arylalkyl group, such as a benzyl group, a phenethyl group, a 1-naphthylmethyl group, a 2-naphthylmethyl group, a 1-naphthylethyl group or a 2-naphthylethyl group. The alkyl chain within the arylalkyl group preferably has 1 to 4 carbon atom, more preferably 1 or 2, and most preferably 1.

When $R^5$ represents any of these aromatic hydrocarbon groups, examples thereof include groups which have a carbonyl group, an ester bond or a sulfonyl group within the ring skeleton of the aromatic ring, between the aromatic ring and the alkylene group, or within the alkylene group bonded to the aromatic ring.

The aromatic hydrocarbon group may have a substituent other than a carbonyl group, an ester bond and a sulfonyl group. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the ring of the aforementioned arylalkyl group has been substituted with the aforementioned heteroatom can be used.

In the latter example, as the substituent for the aromatic hydrocarbon group, an alkyl group of 1 to 5 carbon atoms, an alkoxy group, a halogen atom, a halogenated alkyl group, a hydroxyl group, a cyano group or the like can be used. Further, in the latter example, the aromatic hydrocarbon group may contain an ester group. As the alkoxy group, halogen atom and halogenated alkyl group for the substituent, the same groups as those described above as the substituent for the aforementioned linear or branched, saturated hydrocarbon group can be mentioned.

Among the aforementioned examples, in terms of reducing defects, achieving excellent lithography properties and forming a resist pattern having an excellent shape, the hydrocarbon group for $R^5$ is preferably an aliphatic hydrocarbon group, more preferably a bulky aliphatic hydrocarbon group, and most preferably a cyclic, saturated hydrocarbon group.

By virtue of $R^5$ being a bulky group, the uniformity of the distribution of the component (B1) within a resist film can be improved. Further, dissolution inhibiting effect can be obtained at unexposed portions of the resist film, thereby enabling the formation of a resist pattern having an excellent shape. The reason why such effects can be achieved has not yet been elucidated, but is presumed that, when $R^5$ is a bulky group, the dissolution rate in an alkali developing solution becomes low, thereby suppressing thickness loss especially at unexposed portions.

Preferable examples of $R^5$ include groups represented by formulas (R5-1) to (R5-12) shown below, a group in which a hydrogen atom bonded to a polycyclic group has been substituted with an oxygen atom (═O), and a group in which a hydrogen atom bonded to a monocyclic group has been substituted with an oxygen atom (═O).

[Chemical Formula 46]

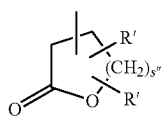
(R5-1)

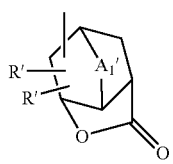
(R5-2)

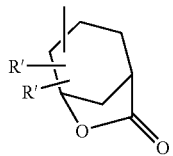
(R5-3)

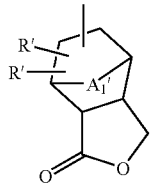
(R5-4)

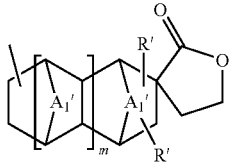
(R5-5)

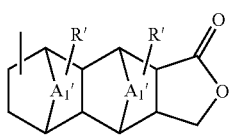
(R5-6)

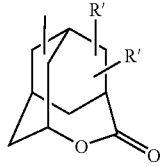
(R5-7)

[Chemical Formula 47]

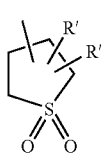
(R5-8)

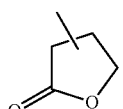
(R5-9)

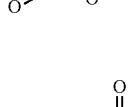
(R5-10)

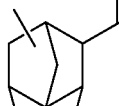
(R5-11)

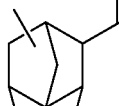
(R5-12)

In the formulas, each R' independently represents a hydrogen atom, an alkyl group of 1 to 5 carbon atoms, an alkoxy group of 1 to 5 carbon atoms or —COOR"; R" represents a hydrogen atom or an alkyl group; $A_1$' represents an oxygen atom, a sulfonyl group or an alkylene group of 1 to 5 carbon atoms which may contain an oxygen atom or a sulfur atom; s" represents an integer of 0 to 2; and m represents 0 or 1.

In the formulas above, R', R", s" and m are respectively the same as defined for R', R", s" and m described above in connection with the aforementioned structural unit (a2).

As $A_1$', an alkylene group of 1 to 5 carbon atoms or an oxygen atom (—O—) is preferable, and a methylene group or —O— is more preferable.

Specific examples of preferable groups for $R^5$ are shown below.

[Chemical Formula 48]

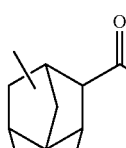

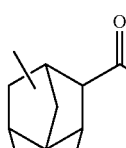

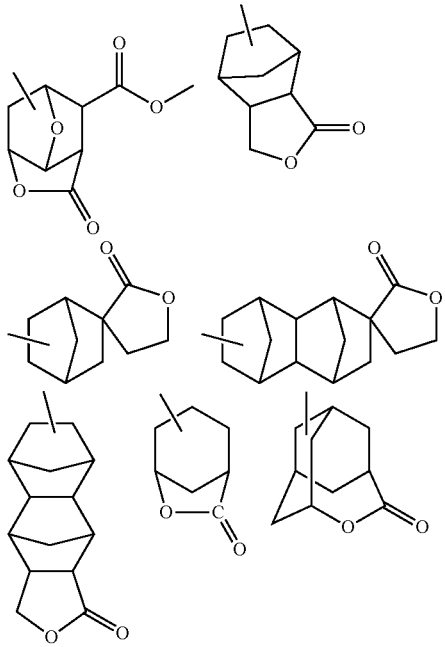

[Chemical Formula 49]

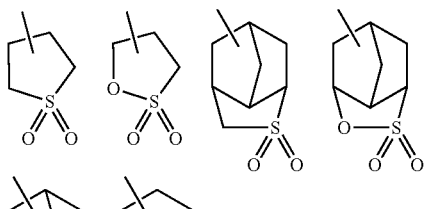

[Chemical Formula 50]

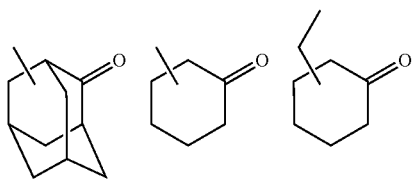

In general formula (I), Q represents a divalent linking group.

Examples of the divalent linking group for Q include an alkylene group and a group containing a hetero atom (hereafter, referred to as "hetero atom-containing linking group").

The alkylene group is preferably a linear or branched alkylene group, more preferably an alkylene group of 1 to 5 carbon atoms, still more preferably an alkylene group of 1 to 3 carbon atoms, still more preferably a methylene group or an ethylene group, and most preferably a methylene group.

The "hetero atom" within the hetero atom-containing linking group is an atom other than carbon and hydrogen, and examples thereof include an oxygen atom, a sulfur atom and a nitrogen atom.

Examples of the hetero atom-containing linking group include non-hydrocarbon, heteroatom-containing linking groups, such as an oxygen atom (ether bond: —O—), a sulfur atom (thioether bond: —S—), an —NH— bond (H may be substituted with a substituent such as an alkyl group or an acyl group), an ester bond (—C(=O)—O—), an amide bond (—C(=O)—NH—) and a carbonyl group (—C(=O)—), a carbonate bond (—O—C(=O)—O—); and a combination of the aforementioned non-hydrocarbon, hetero atom-containing linking group with the aforementioned alkylene group.

Examples of such a combination include —$R^{90}$—O—, —$R^{91}$—C(=O)— and —$R^{92}$—C(=O)—O—$R^{93}$— (in the formulas, $R^{90}$ and $R^{91}$ to $R^{93}$ independently represents an alkylene group).

As the alkylene group for $R^{90}$ and $R^{91}$ to $R^{93}$, the same alkylene groups as those described above as the divalent linking group for Q can be mentioned.

Among these, in terms of reducing defects, achieving excellent lithography properties and forming a resist pattern having an excellent shape, Q is preferably an alkylene group or a divalent linking group containing an ester bond, and an alkylene group or —$R^{92}$—C(=O)—O—$R^{93}$— is particularly desirable.

In the present invention, the component (B1) is not particularly limited, as long as it is a group having a cation moiety comprising a group represented by general formula (I). In terms of reducing defects, achieving excellent lithography properties and forming a resist pattern having an excellent shape, the component (B1) is preferably a compound represented by general formula (b1-11) shown below.

[Chemical Formula 51]

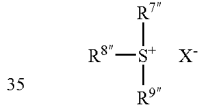

(b1-11)

In formula (b1-11), each of $R^{7\prime\prime}$ to $R^{9\prime\prime}$ independently represents an aryl group or an alkyl group, and two of $R^{7\prime\prime}$ to $R^{9\prime\prime}$ may be bonded to each other to form a ring with the sulfur atom, with the provision that at least one of $R^{7\prime\prime}$ to $R^{9\prime\prime}$ represents a substituted aryl group having a group represented by general formula (I) as a substituent; and $X^-$ represents an anion.

In general formula (b1-11), each of $R^{7\prime\prime}$ to $R^{9\prime\prime}$ independently represents an aryl group or an alkyl group, provided that at least one of $R^{7\prime\prime}$ to $R^{9\prime\prime}$ represents a substituted aryl group having a group represented by general formula (I) as a substituent.

The aryl group for $R^{7\prime\prime}$ to $R^{9\prime\prime}$ is not particularly limited. For example, an aryl group having 6 to 20 carbon atoms may be used in which part or all of the hydrogen atoms of the aryl group may or may not be substituted with a substituent other than those represented by general formula (I), e.g., an alkyl group, an alkoxy group, a halogen atom or a hydroxyl group.

The aryl group is preferably an aryl group having 6 to 10 carbon atoms because it can be synthesized at a low cost. Specific examples thereof include a phenyl group and a naphthyl group.

The alkyl group, with which hydrogen atoms of the aryl group may be substituted, is preferably an alkyl group having 1 to 5 carbon atoms, more preferably a methyl group, an ethyl group, a propyl group, an n-butyl group, or a tert-butyl group, and most preferably a methyl group.

The alkoxy group, with which hydrogen atoms of the aryl group may be substituted, is preferably an alkoxy group having 1 to 5 carbon atoms, more preferably a methoxy group, an ethoxy group, an n-propoxy group, an iso-propoxy group, an n-butoxy group or a tert-butoxy group.

The halogen atom, with which hydrogen atoms of the aryl group may be substituted, is preferably a fluorine atom.

The alkyl group for $R^{7\prime\prime}$ to $R^{9\prime\prime}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples include a methyl group, an ethyl group, an n-propyl group, an isopropyl group, an n-butyl group, an isobutyl group, an n-pentyl group, a cyclopentyl group, a hexyl group, a cyclohexyl group, a nonyl group and a decanyl group. Among these, a methyl group is preferable because it is excellent in resolution and can be synthesized at a low cost.

In general formula (b1-11), two of $R^{7\prime\prime}$ to $R^{9\prime\prime}$ may be bonded to each other to form a ring with the sulfur atom.

In such a case, the ring including the sulfur atom is preferably a 3- to 10-membered ring, and more preferably a 5- to 7-membered ring.

When two of $R^{7\prime\prime}$ to $R^{9\prime\prime}$ are bonded to each other to form a ring with the sulfur atom, the remaining one of $R^{7\prime\prime}$ to $R^{9\prime\prime}$ is preferably an aryl group. The aryl group is preferably a substituted aryl group having a group represented by general formula (I) as a substituent.

The ring structure formed with the sulfur atom may include a hetero atom such as a sulfur atom or an oxygen atom (—O—, =O).

In the present invention, at least one of $R^{7\prime\prime}$ to $R^{9\prime\prime}$ represents a substituted aryl group (hereafter, referred to as "substituted aryl group (I)") having a group represented by general formula (I) as a substituent.

One substituted aryl group (I) preferably has 1 to 3 groups represented by general formula (I), and most preferably 1.

In the substituted aryl group (I), the aryl group to which the group represented by general formula (I) is bonded is preferably a phenyl group or a naphthyl group, and most preferably a phenyl group. In such a case, the group represented by general formula (I) is preferably bonded to the para position of the phenyl group.

The substituted aryl group (I) may have a substituent other than a group represented by general formula (I). Examples of such a substituent include an alkyl group, an alkoxy group, an ether group, a halogen atom, a halogenated alkyl group and a hydroxy group. As specific examples of these substituents, the same groups as those described above for the substituent of the aforementioned substituted aryl group can be mentioned.

The number of such a substituent that one substituted aryl group (I) has is preferably 0 to 2.

Among $R^{7\prime\prime}$ to $R^{9\prime\prime}$, either one, two or three may represent a substituted aryl group (I). However, it is particularly desirable that one of $R^{7\prime\prime}$ to $R^{9\prime\prime}$ represent a substituted aryl group (I).

In such a case, it is preferable that the remaining two represent an aryl group which may have a substituent other than a group represented by general formula (I), or the remaining two be mutually bonded to form a ring with the sulfur atom in the formula.

When each of the remaining two represents an aryl group which may have a substituent, the aryl group is preferably an unsubstituted aryl group, more preferably a phenyl group or a naphthyl group, and most preferably a phenyl group.

Specific examples of preferable cation moieties for the component (B1) are shown below.

[Chemical Formula 52]

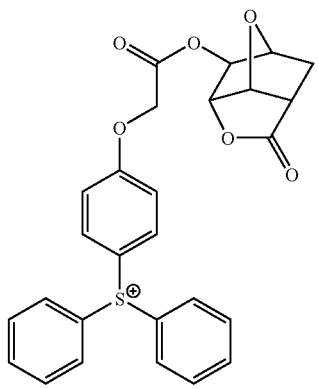

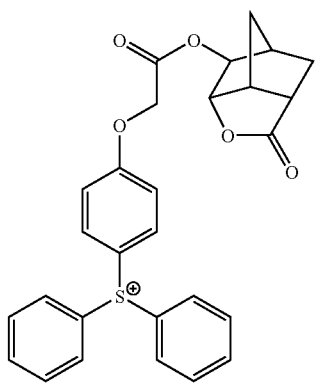

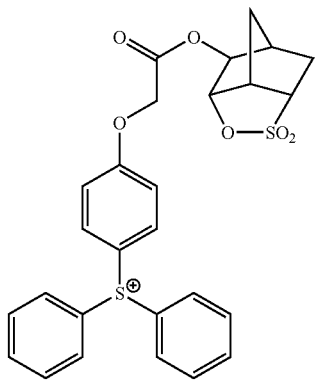

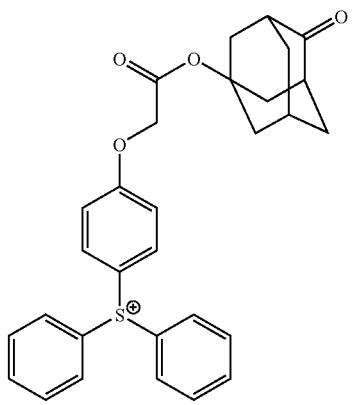

91
-continued
92
-continued
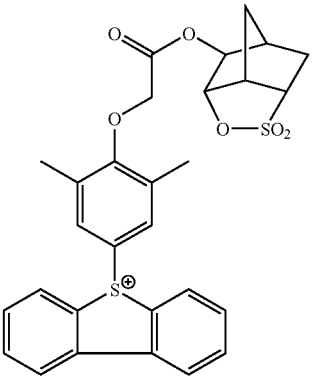
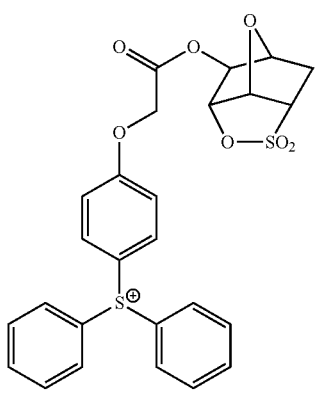
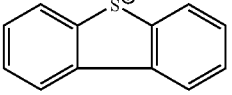
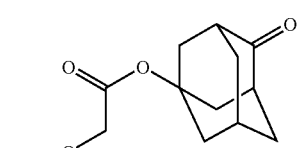
[Chemical Formula 53]
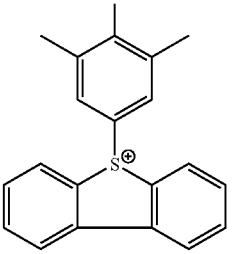
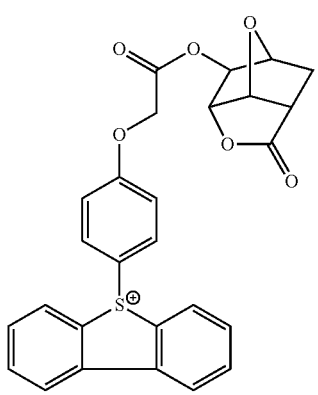
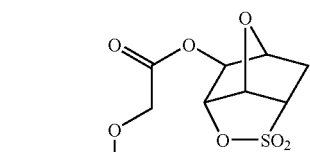
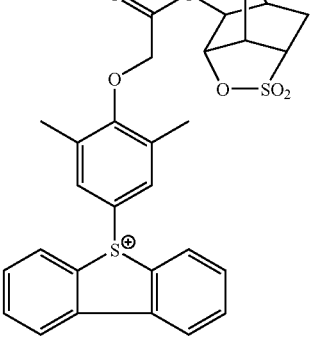
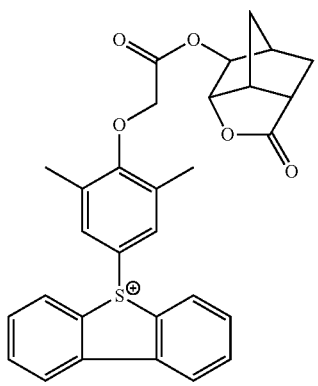
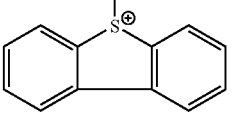
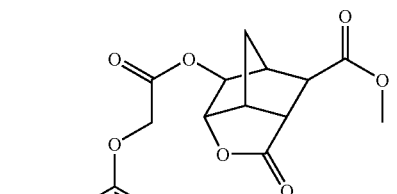
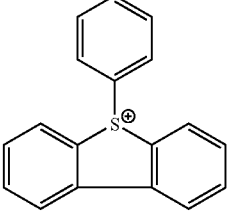

[Chemical Formula 54]
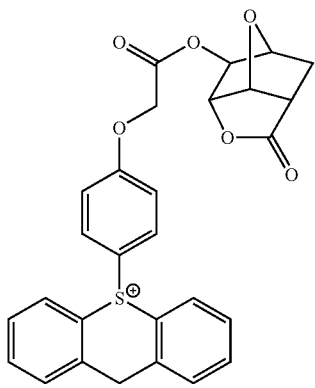
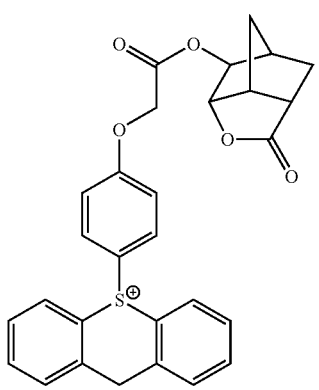
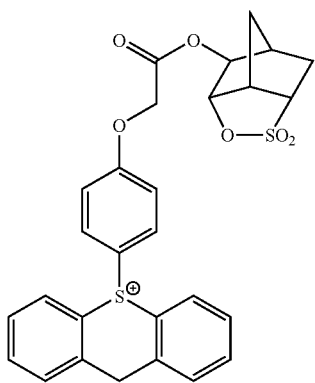
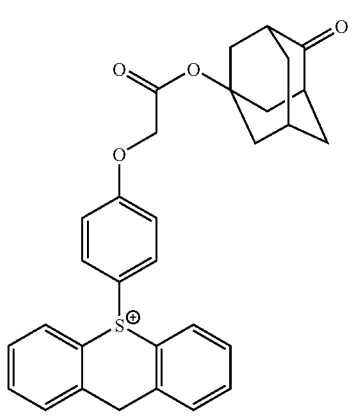
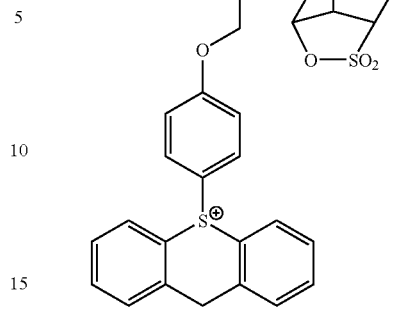
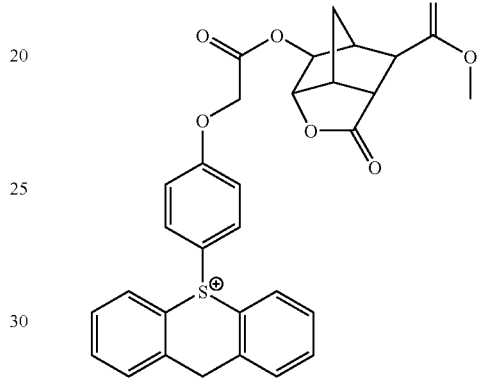
[Chemical Formula 55]
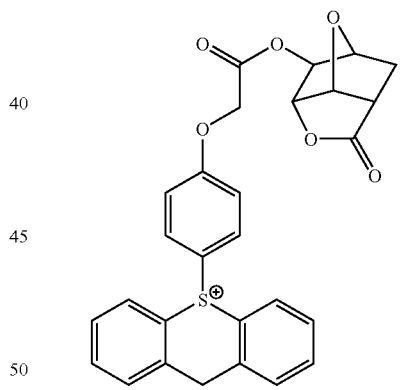
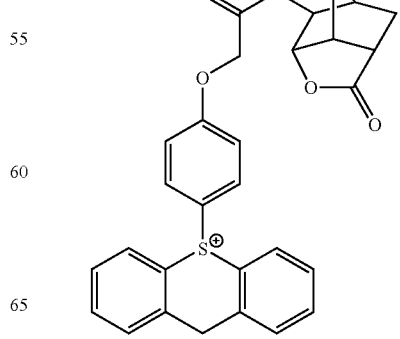

95
-continued
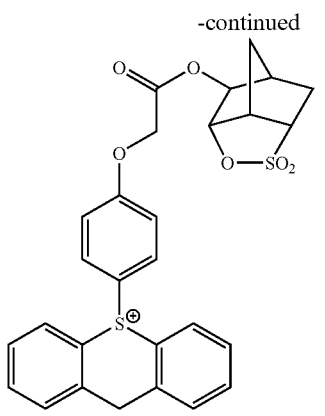
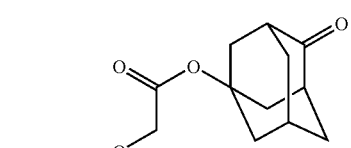
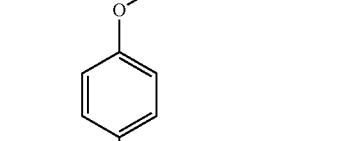
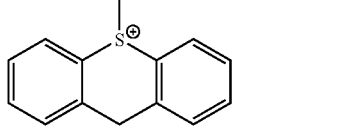
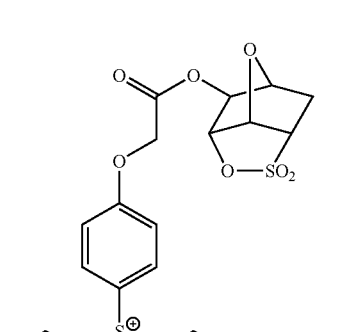
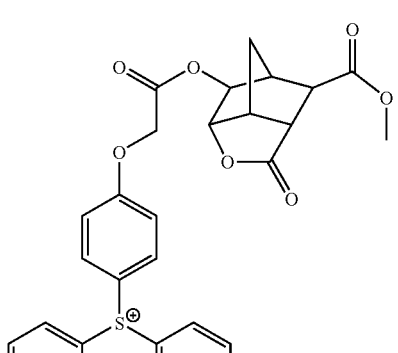
96
-continued
[Chemical Formula 56]
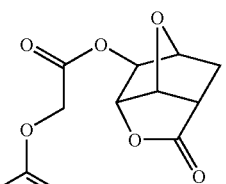
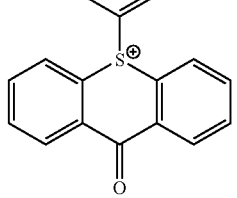
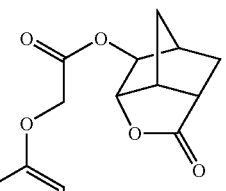
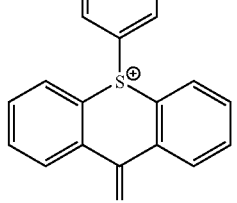
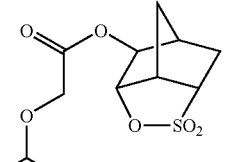
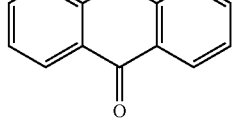

97
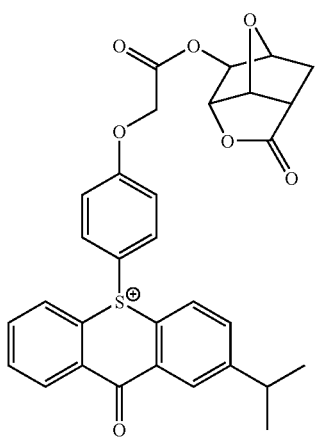
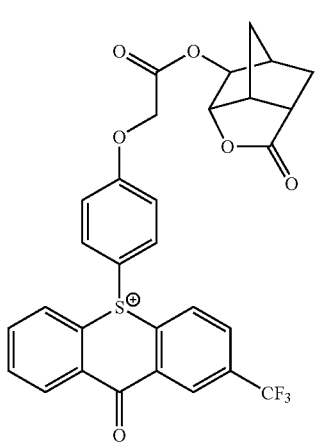
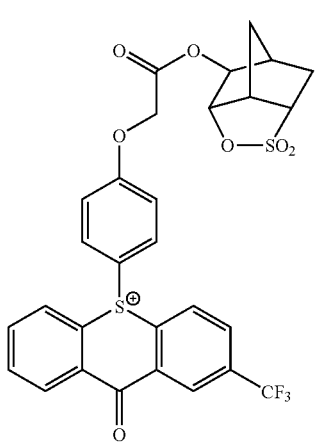
98
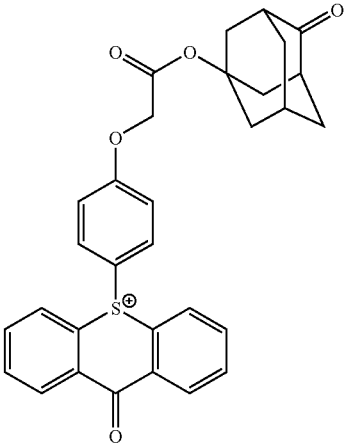
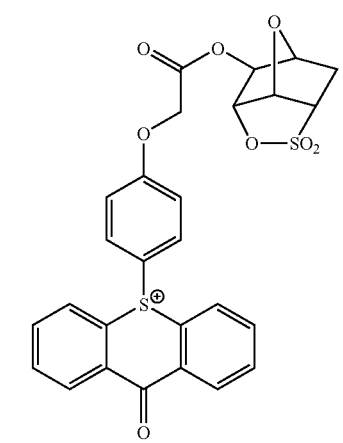
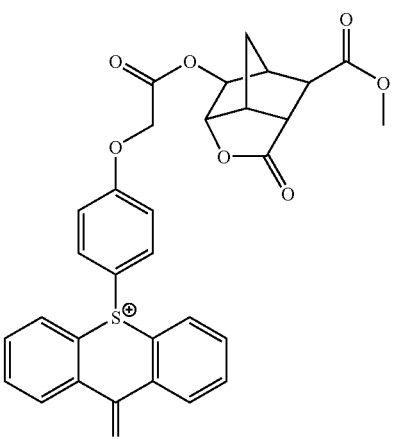

99
-continued
[Chemical Formula 57]
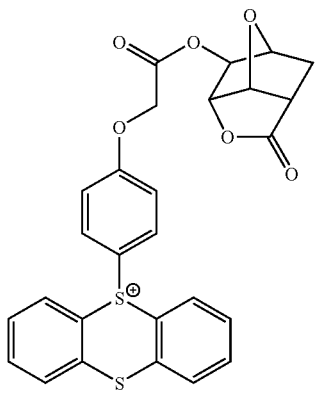
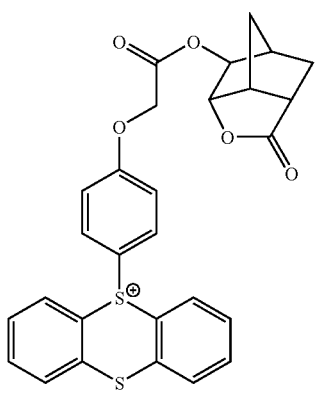
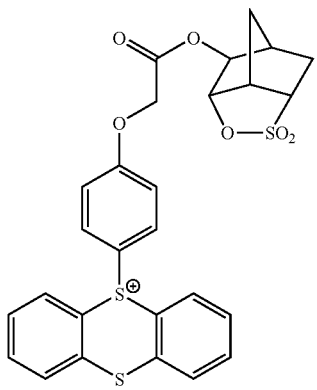
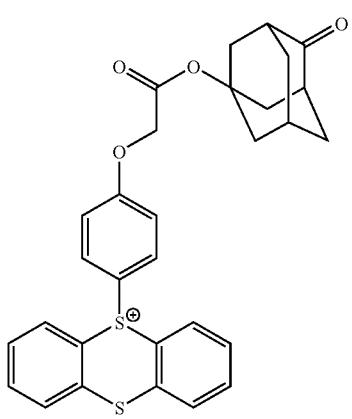
100
-continued
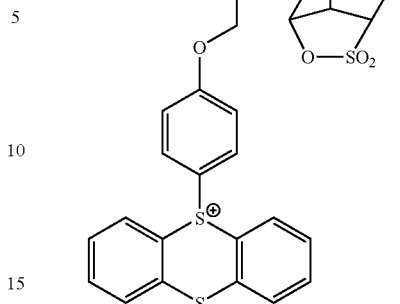
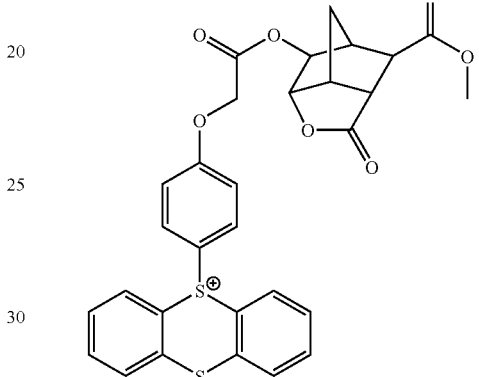
[Chemical Formula 58]
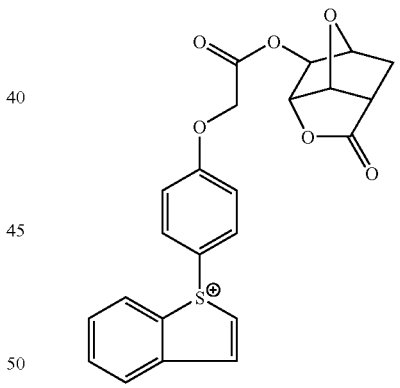
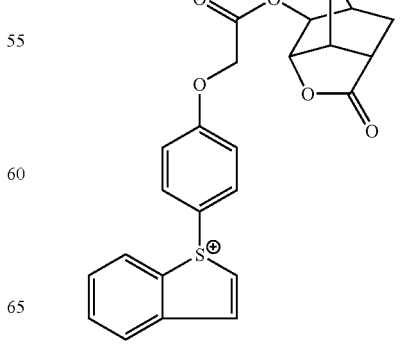

101
-continued
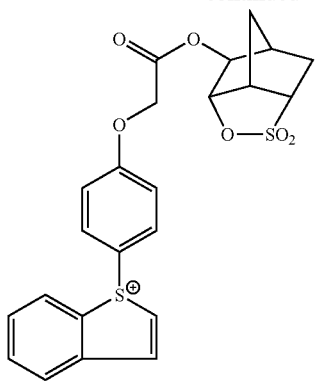
102
-continued
[Chemical Formula 59]
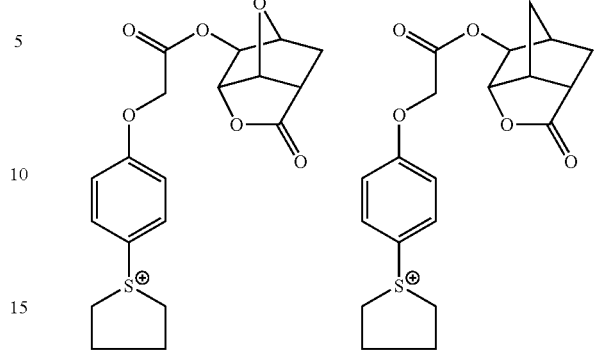
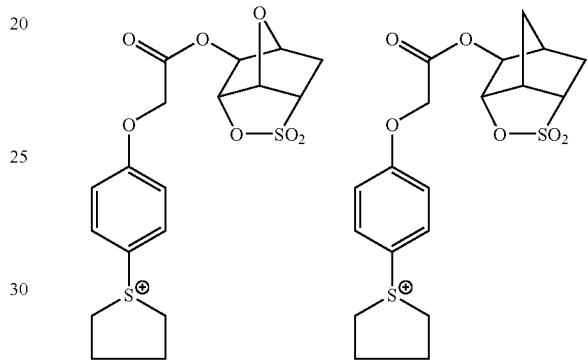
[Chemical Formula 60]
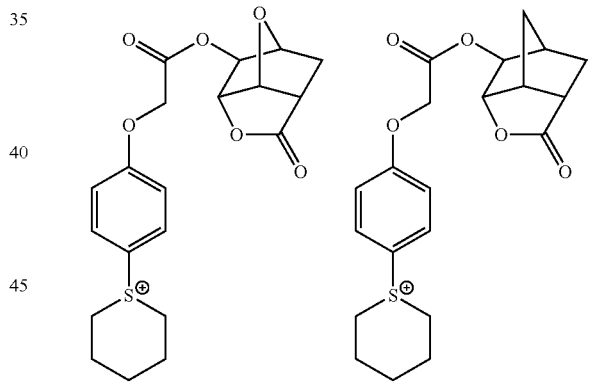
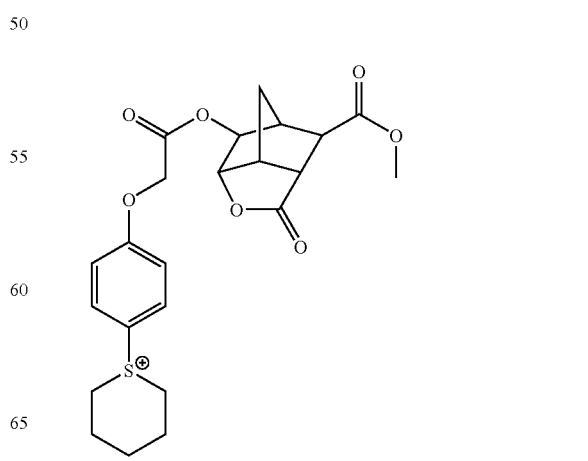

-continued
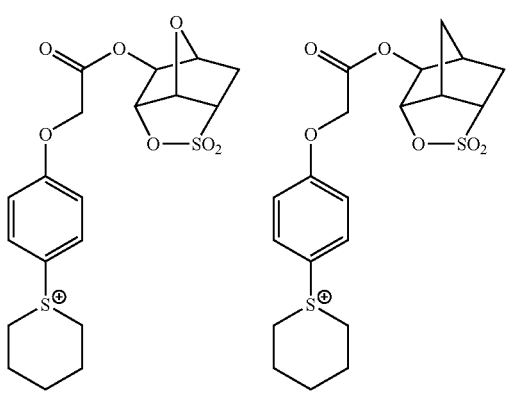
[Chemical Formula 61]
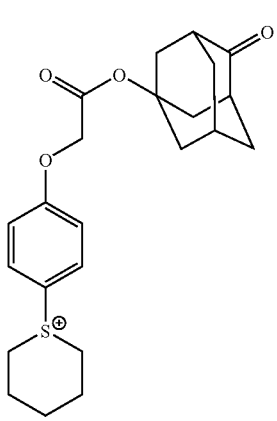
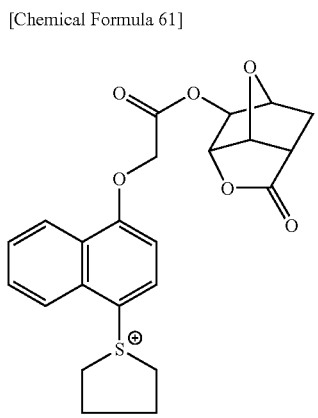
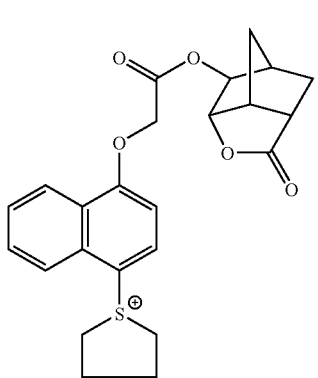
-continued
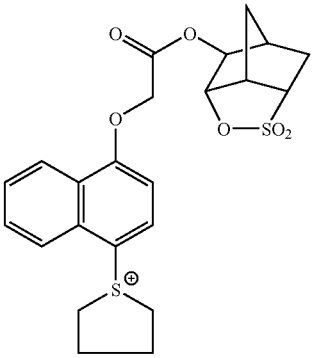
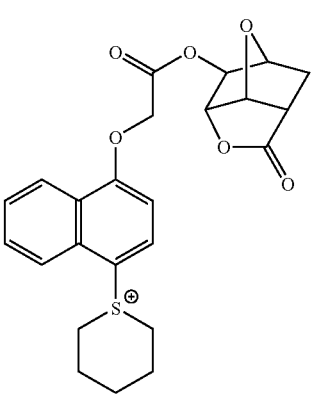
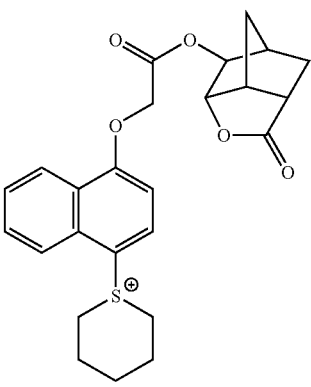
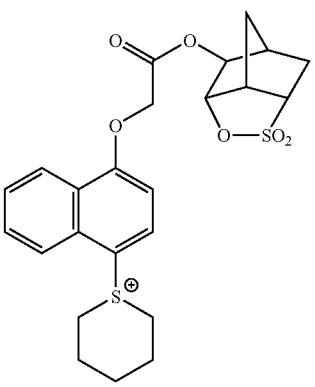

-continued

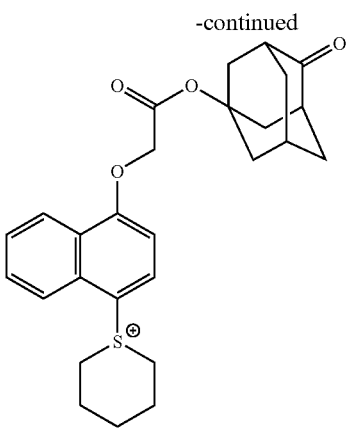

Anion Moiety of Component (B1)

In formula (b1-11), the anion for X⁻ is not particularly limited, and preferable examples thereof include a sulfonate anion, an imide anion, a methide anion and a halogen anion.

(Sulfonate Anion)

As a preferable example of a sulfonate anion, an anion represented by general formula (x-1) shown below can be given.

[Chemical Formula 62]

In the formula, $R^{4'''}$ represents an alkyl group, a halogenated alkyl group, an aryl group or an alkenyl group, which may have a substituent.

The alkyl group for $R^{4'''}$ may be any of linear, branched or cyclic.

The linear or branched alkyl group preferably has 1 to 10 carbon atoms, more preferably 1 to 8 carbon atoms, and most preferably 1 to 4 carbon atoms.

The cyclic alkyl group preferably has 4 to 15 carbon atoms, more preferably 4 to 10 carbon atoms, and most preferably 6 to 10 carbon atoms. The cyclic group may be either a monocyclic group or a polycyclic group, and specific examples thereof include a cyclopentyl group, a cyclohexyl group, an adamantyl group, a norbornyl group, an isobornyl group, a tricyclodecanyl group and a tetracyclododecanyl group.

When $R^{4'''}$ represents an alkyl group, although the acid strength becomes weak, it can be preferably used for a negative resist composition.

As an example of the halogenated alkyl group for $R^{4'''}$, a group in which part of or all of the hydrogen atoms of the aforementioned linear, branched or cyclic alkyl group have been substituted with halogen atoms can be given. Examples of the aforementioned halogen atom include a fluorine atom, a chlorine atom, a bromine atom and an iodine atom, and a fluorine atom is preferable.

In the halogenated alkyl group, the percentage of the number of halogen atoms based on the total number of halogen atoms and hydrogen atoms (halogenation ratio (%)) is preferably 10 to 100%, more preferably 50 to 100%, and most preferably 100%. Higher halogenation ratio is preferable because the acid strength increases.

The aryl group for $R^{4'''}$ is preferably an aryl group of 6 to 20 carbon atoms.

The alkenyl group for $R^{4'''}$ is preferably an alkenyl group of 2 to 10 carbon atoms.

With respect to $R^{4'''}$, the expression "may have a substituent" means that part of or all of the hydrogen atoms within the aforementioned alkyl group, halogenated alkyl group, aryl group or alkenyl group may be substituted with substituents (atoms other than hydrogen atoms, or groups).

$R^{4'''}$ may have one substituent, or two or more substituents.

Examples of the substituent include a halogen atom, a hetero atom, an alkyl group, and a group represented by the formula $Z\text{-}Q^1\text{-}$ (in the formula, $Q^1$ represents a divalent linking group containing an oxygen atom; and Z represents a hydrocarbon group of 3 to 30 carbon atoms which may have a substituent).

Examples of the halogen atom as a substituent for $R^{4'''}$ include the same halogen atoms as those described above with respect to the halogenated alkyl group for $R^{4'''}$.

Examples of the alkyl group as a substituent for $R^{4'''}$ include the same alkyl groups as those described above with respect to the alkyl group for $R^{4'''}$.

Examples of the hetero atom include an oxygen atom (=O, —O—), a nitrogen atom, and a sulfur atom.

In the group represented by formula $Z\text{-}Q^1\text{-}$, $Q^1$ represents a divalent linking group containing an oxygen atom.

$Q^1$ may contain an atom other than an oxygen atom. Examples of atoms other than an oxygen atom include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond; —O—), an ester bond (—C(=O)—O—), an amido bond (—C(=O)—NH—), a carbonyl group (—C(=O)—) and a carbonate group (—O—C(=O)—O—); and combinations of the aforementioned non-hydrocarbon, hetero atom-containing linking groups with an alkylene group.

Specific examples of the combinations of the aforementioned non-hydrocarbon, hetero atom-containing linking groups and an alkylene group include —$R^{96}$—O—, —$R^{97}$—O—C(=O)—, —O—$R^{97}$—O—C(=O)—, —C(=O)—O—$R^{98}$—O—C(=O)—, and —C(=O)—O—$R^{98}$— (in the formulas, each of $R^{96}$ to $R^{98}$ independently represents an alkylene group).

The alkylene group for $R^{96}$ to $R^{98}$ is preferably a linear or branched alkylene group, and preferably has 1 to 12 carbon atoms, more preferably 1 to 5, and most preferably 1 to 3.

Specific examples of alkylene groups include a methylene group [—CH₂—]; alkylmethylene groups such as —CH(CH₃)—, —CH(CH₂CH₃)—, —C(CH₃)₂—, —C(CH₃)(CH₂CH₃)—, —C(CH₃)(CH₂CH₂CH₃)— and —C(CH₂CH₃)₂—; an ethylene group [—CH₂CH₂—]; alkylethylene groups such as —CH(CH₃)CH₂—, —CH(CH₃)CH (CH₃)—, —C(CH₃)₂CH₂— and —CH(CH₂CH₃)CH₂—; a trimethylene group (n-propylene group) [—CH₂CH₂CH₂—]; alkyltrimethylene groups such as —CH (CH₃)CH₂CH₂— and —CH₂CH(CH₃)CH₂—; a tetramethylene group [—CH₂CH₂CH₂CH₂—]; alkyltetramethylene groups such as —CH(CH₃)CH₂CH₂CH₂— and —CH₂CH (CH₃)CH₂CH₂—; and a pentamethylene group [—CH₂CH₂CH₂CH₂CH₂—].

$Q^1$ is preferably a divalent linking group containing an ester bond or an ether bond, more preferably —O—, —$R^{96}$—O—, —O—C(=O)—, —O—$R^{97}$—O—C(=O)—, —$R^{97}$—O—C(=O)—, —C(=O)—O—$R^{98}$—O—C (=O)— or —C(=O)—O—$R^{98}$—, and most preferably —O—C(=O)—, —C(=O)—O—$R^{98}$—O—C(=O)— or —C(=O)—O—$R^{98}$—.

In the group represented by the formula $Z\text{-}Q^1\text{-}$, the hydrocarbon group for Z may be either an aromatic hydrocarbon group or an aliphatic hydrocarbon group.

The aromatic hydrocarbon group is a hydrocarbon group having an aromatic ring. The aromatic hydrocarbon ring preferably has 3 to 30 carbon atoms, more preferably 5 to 30, still more preferably 5 to 20, still more preferably 6 to 15, and most preferably 6 to 12. Here, the number of carbon atoms within a substituent(s) is not included in the number of carbon atoms of the aromatic hydrocarbon group.

Specific examples of aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an alkylaryl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 or 2, and most preferably 1.

The aromatic hydrocarbon group may have a substituent. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the aromatic hydrocarbon ring within the aforementioned arylalkyl group has been substituted with the aforementioned heteroatom can be used.

In the latter example, as the substituent for the aromatic hydrocarbon group, an alkyl group, an alkoxy group, a halogen atom, a halogenated alkyl group, a hydroxyl group, an oxygen atom (=O) or the like can be used.

The alkyl group as the substituent for the aromatic hydrocarbon group is preferably an alkyl group of 1 to 5 carbon atoms, and a methyl group, an ethyl group, a propyl group, an n-butyl group or a tert-butyl group is particularly desirable.

The alkoxy group as the substituent for the aromatic hydrocarbon group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Example of the halogenated alkyl group as the substituent for the aromatic hydrocarbon group includes a group in which part or all of the hydrogen atoms within the aforementioned alkyl group have been substituted with the aforementioned halogen atoms.

The aliphatic hydrocarbon group for Z may be either a saturated aliphatic hydrocarbon group, or an unsaturated aliphatic hydrocarbon group. Further, the aliphatic hydrocarbon group may be linear, branched or cyclic.

In the aliphatic hydrocarbon group for Z, a part of the carbon atoms constituting the aliphatic hydrocarbon group may be substituted with a substituent group containing a hetero atom, or a part or all of the hydrogen atoms constituting the aliphatic hydrocarbon group may be substituted with a substituent group containing a hetero atom.

As the "hetero atom" for Z, there is no particular limitation as long as it is an atom other than a carbon atom and a hydrogen atom. Examples of hetero atoms include a halogen atom, an oxygen atom, a sulfur atom and a nitrogen atom. Examples of halogen atoms include a fluorine atom, a chlorine atom, an iodine atom and a bromine atom.

The substituent group containing a hetero atom may consist of a hetero atom, or may be a group containing a group or atom other than a hetero atom.

Specific examples of the substituent group for substituting part of the carbon atoms include —O—, —C(=O)—O—, —C(=O)—, —C(=O)—NH—, —NH— (the H may be replaced with a substituent such as an alkyl group or an acyl group), —S(=O)$_2$— and —S(=O)$_2$—O—. When the aliphatic hydrocarbon group is cyclic, the aliphatic hydrocarbon group may contain any of these substituent groups in the ring structure.

Examples of the substituent group for substituting part or all of the hydrogen atoms include an alkoxy group, a halogen atom, a halogenated alkyl group, a hydroxyl group, an oxygen atom (=O) and a cyano group.

The aforementioned alkoxy group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the aforementioned halogen atom include a fluorine atom, a chlorine atom, a bromine atom and an iodine atom, and a fluorine atom is preferable. Example of the aforementioned halogenated alkyl group includes a group in which part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable.

The linear saturated hydrocarbon group (alkyl group) preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 10 carbon atoms, more preferably 2 to 5, still more preferably 2 to 4, and most preferably 3. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30, still more preferably 5 to 20, still more preferably 6 to 15, and most preferably 6 to 12.

As the aliphatic cyclic group, a group in which one or more hydrogen atoms have been removed from a monocycloalkane or a polycycloalkane such as a bicycloalkane, tricycloalkane or tetracycloalkane can be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)$_2$— or —S(=O)$_2$—O—. Specific examples of such aliphatic cyclic groups include groups represented by formulas (L1) to (L5) and (S1) to (S4) shown below.

[Chemical Formula 63]

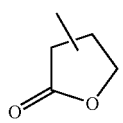
(L1)

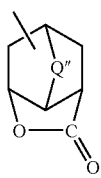
(L2)

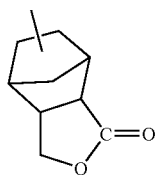
(L3)

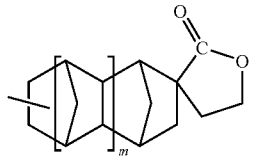
(L4)

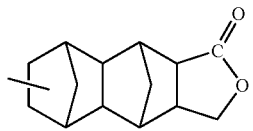
(L5)

-continued

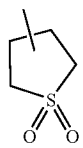
(S1)

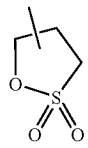
(S2)

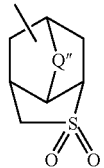
(S3)

(S4)

In the formula, Q″ represents an alkylene group of 1 to 5 carbon atoms, —O—, —S—, —O—R$^{94}$— or —S—R$^{95}$— (wherein each of R$^{94}$ and R$^{95}$ independently represents an alkylene group of 1 to 5 carbon atoms); and m represents 0 or 1.

As the alkylene group for Q″, R$^{94}$ and R$^{95}$, the same alkylene groups as those described above for R$^{96}$ to R$^{98}$ can be used.

In these aliphatic cyclic groups, part of the hydrogen atoms bonded to the carbon atoms constituting the ring structure may be substituted with a substituent. Examples of substituents include an alkyl group, an alkoxy group, a halogen atom, a halogenated alkyl group, a hydroxyl group and an oxygen atom (=O).

As the alkyl group, an alkyl group of 1 to 5 carbon atoms is preferable, and a methyl group, an ethyl group, a propyl group, an n-butyl group or a tert-butyl group is particularly desirable.

As the alkoxy group and the halogen atom, the same groups as the substituent groups for substituting part or all of the hydrogen atoms can be used.

In the present invention, as Z, a cyclic group which may have a substituent is preferable. The cyclic group may be either an aromatic hydrocarbon group which may have a substituent, or an aliphatic cyclic group which may have a substituent, and an aliphatic cyclic group which may have a substituent is preferable.

As the aromatic hydrocarbon group, a naphthyl group which may have a substituent, or a phenyl group which may have a substituent is preferable.

As the aliphatic cyclic group which may have a substituent, an aliphatic polycyclic group which may have a substituent is preferable. As the aliphatic polycyclic group, the aforementioned group in which one or more hydrogen atoms have been removed from a polycycloalkane, and groups represented by formulas (L2) to (L5), (S3) and (S4) are preferable.

In the present invention, when $R^{4'''}$ has $Z-Q^1-$ as a substituent, $R^{4'''}$ is preferably a group represented by the formula $Z-Q^1-Y^1-$ (in the formula, $Q^1$ and $Z$ are the same as defined above; and $Y^1$ represents an alkylene group of 1 to 4 carbon atoms which may have a substituent or a fluorinated alkylene group of 1 to 4 carbon atoms which may have a substituent.

That is, when $X^-$ represents a sulfonate anion, it is preferably an anion represented by general formula (x-11) shown below.

[Chemical Formula 64]

$$Z-Q^1-Y^1-SO_3^- \quad (x\text{-}11)$$

In the formula, $Q^1$ represents a divalent linking group containing an oxygen atom; $Z$ represents a hydrocarbon group of 3 to 30 carbon atoms which may have a substituent; and $Y^1$ represents an alkylene group of 1 to 4 carbon atoms which may have a substituent or a fluorinated alkylene group of 1 to 4 carbon atoms which may have a substituent.

In formula (x-11), $Z$ and $Q^1$ are the same as defined above.

As the alkylene group for $Y^1$, the same alkylene groups as those described above for $Q^1$ which have 1 to 4 carbon atoms can be mentioned.

As the fluorinated alkylene group, the aforementioned alkylene group in which part or all of the hydrogen atoms has been substituted with fluorine atoms can be used.

Specific examples of $Y^1$ include $-CF_2-$, $-CF_2CF_2-$, $-CF_2CF_2CF_2-$, $-CF(CF_3)CF_2-$, $-CF(CF_2CF_3)-$, $-C(CF_3)_2-$, $-CF_2CF_2CF_2CF_2-$, $-CF(CF_3)CF_2CF_2-$, $-CF_2CF(CF_3)CF_2-$, $-CF(CF_3)CF(CF_3)-$, $-C(CF_3)_2CF_2-$, $-CF(CF_2CF_3)CF_2-$, $-CF(CF_2CF_2CF_3)-$, $-C(CF_3)(CF_2CF_3)-$; $-CHF-$, $-CH_2CF_2-$, $-CH_2CH_2CF_2-$, $-CH_2CF_2CF_2-$, $-CH(CF_3)CH_2-$, $-CH(CF_2CF_3)-$, $-C(CH_3)(CF_3)-$, $-CH_2CH_2CH_2CF_2-$, $-CH_2CH_2CF_2CF_2-$, $-CH(CF_3)CH_2CH_2-$, $-CH_2CH(CF_3)CH_2-$, $-CH(CF_3)CH(CF_3)-$, $-C(CF_3)_2CH_2-$; $-CH_2-$, $-CH_2CH_2-$, $-CH_2CH_2CH_2-$, $-CH(CH_3)CH_2-$, $-CH(CH_2CH_3)-$, $-C(CH_3)_2-$, $-CH_2CH_2CH_2CH_2-$, $-CH(CH_3)CH_2CH_2-$, $-CH_2CH(CH_3)CH_2-$, $-CH(CH_3)CH(CH_3)-$, $-C(CH_3)_2CH_2-$, $-CH(CH_2CH_3)CH_2-$, $-CH(CH_2CH_2CH_3)-$, and $-C(CH_3)(CH_2CH_3)-$.

$Y^1$ is preferably a fluorinated alkylene group, and particularly preferably a fluorinated alkylene group in which the carbon atom bonded to the adjacent sulfur atom is fluorinated. Examples of such fluorinated alkylene groups include $-CF_2-$, $-CF_2CF_2-$, $-CF_2CF_2CF_2-$, $-CF(CF_3)CF_2-$, $-CF_2CF_2CF_2CF_2-$, $-CF(CF_3)CF_2CF_2-$, $-CF_2CF(CF_3)CF_2-$, $-CF(CF_3)CF(CF_3)-$, $-C(CF_3)_2CF_2-$, $-CF(CF_2CF_3)CF_2-$; $-CH_2CF_2-$, $-CH_2CH_2CF_2-$, $-CH_2CF_2CF_2-$; $-CH_2CH_2CH_2CF_2-$, $-CH_2CH_2CF_2CF_2-$, and $-CH_2CF_2CF_2CF_2-$.

Of these, $-CF_2-$, $-CF_2CF_2-$, $-CF_2CF_2CF_2-$ or $CH_2CF_2CF_2-$ is preferable, $-CF_2-$, $-CF_2CF_2-$ or $-CF_2CF_2CF_2-$ is more preferable, and $-CF_2-$ is particularly desirable.

The alkylene group or fluorinated alkylene group may have a substituent. The alkylene group or fluorinated alkylene group "has a substituent" means that part or all of the hydrogen atoms or fluorine atoms in the alkylene group or fluorinated alkylene group has been substituted with groups other than hydrogen atoms and fluorine atoms.

Examples of substituents which the alkylene group or fluorinated alkylene group may have include an alkyl group of 1 to 4 carbon atoms, an alkoxy group of 1 to 4 carbon atoms, and a hydroxyl group.

Preferable examples of the anion represented by formula (x-11) include anions represented by formulas (b1) to (b8) shown below.

[Chemical Formula 65]

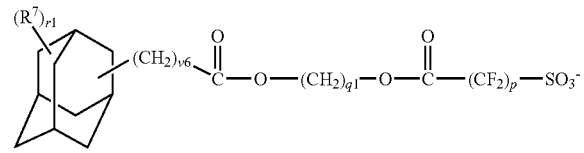
(b1)

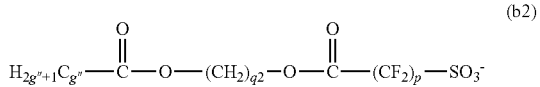
(b2)

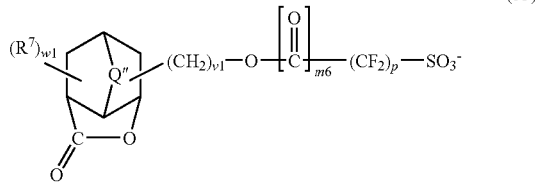
(b3)

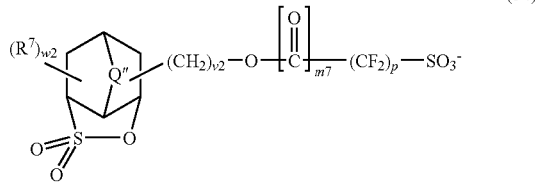
(b4)

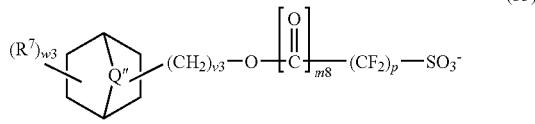
(b5)

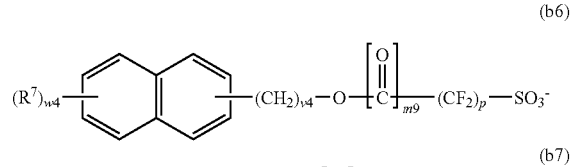
(b6)

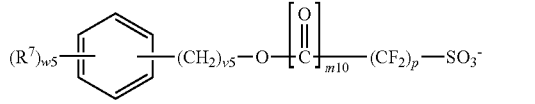
(b7)

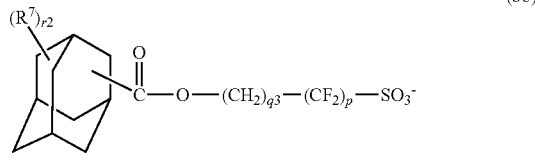
(b8)

In the formulas, p represents an integer of 1 to 3; each of q1 to q3 independently represents an integer of 1 to 5; each of r1 and r2 independently represents an integer of 0 to 3; g''' represents an integer of 1 to 20; $R^7$ represents a substituent; each of $m_6$ to $m_{10}$) independently represents 0 or 1; each of v1 to v6 independently represents an integer of 0 to 3; each of w1 to w5 independently represents an integer of 0 to 3; and Q'' is the same as defined above.

As the substituent for $R^7$, the same groups as those which the aforementioned aliphatic hydrocarbon group or aromatic hydrocarbon group for Z may have as a substituent can be used If there are two or more of the $R^7$ group, as indicated by the values r1, r2, and w1 to w5, then the two or more of the $R^7$ groups may be the same or different from each other.

(Imide Anion)

When $X^-$ represents an imide anion, it is preferably an anion represented by general formula (b-3) or (b-4) shown below.

[Chemical Formula 66]

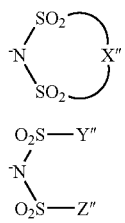

(b-3)

(b-4)

In the formulas, X" represents an alkylene group of 2 to 6 carbon atoms in which at least one hydrogen atom has been substituted with a fluorine atom; and each of Y" and Z" independently represents an alkyl group which may have a substituent or a halogenated alkyl group which may have a substituent.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

The smaller the number of carbon atoms of the alkylene group for X" within the above-mentioned range of the number of carbon atoms, the more the solubility in a resist solvent is improved.

Further, in the alkylene group for X", it is preferable that the number of hydrogen atoms substituted with fluorine atoms is as large as possible because the acid strength increases and the transparency to high energy radiation of 200 nm or less or electron beam is improved. The fluorination ratio of the alkylene group or alkyl group is preferably from 70 to 100%, more preferably from 90 to 100%, and it is particularly desirable that the alkylene group or alkyl group be a perfluoroalkylene group or perfluoroalkyl group in which all hydrogen atoms are substituted with fluorine atoms.

Each of Y" and Z" independently represents an alkyl group which may have a substituent or a halogenated alkyl group which may have a substituent.

The alkyl group for Y" and Z" may be linear, branched or cyclic, and examples thereof include the same alkyl groups as those described above for $R^{4''}$.

As the halogenated alkyl group for Y" and Z", a group in which part of or all of the hydrogen atoms of the aforementioned linear, branched or cyclic alkyl group have been substituted with halogen atoms can be mentioned, and examples thereof include the same alkyl groups as those described above for $R^{4''}$. In the halogenated alkyl group, the percentage of the number of halogen atoms based on the total number of halogen atoms and hydrogen atoms (halogenation ratio (%)) is preferably 10 to 100%, more preferably 50 to 100%, and most preferably 100%. Higher halogenation ratio is preferable because the acid strength increases.

With respect to Y" and Z", the expression "may have a substituent" means that part of or all of the hydrogen atoms within the aforementioned alkyl group or halogenated alkyl group may be substituted with substituents (atoms other than hydrogen atoms, or groups). Y" and Z" may have one substituent, or two or more substituents.

Examples of the substituent include a halogen atom, a hetero atom, an alkyl group, and a group represented by the formula $Z-Q^1-$ (in the formula, $Q^1$ represents a divalent linking group containing an oxygen atom; and Z represents a hydrocarbon group of 3 to 30 carbon atoms which may have a substituent).

Examples of the halogen atom as a substituent for $R^{4''}$ include the same halogen atoms as those described above with respect to the halogenated alkyl group for $R^{4''}$.

Examples of the alkyl group as a substituent for $R^{4''}$ include the same alkyl groups as those described above with respect to the alkyl group for $R^{4''}$.

Examples of the hetero atom include the same hetero atoms as those described above as a substituent for the alkyl group represented by $R^{4''}$.

In the group represented by formula $Z-Q^1-$, $Q^1$ represents a divalent linking group containing an oxygen atom.

Examples of divalent linking groups containing an oxygen atom include non-hydrocarbon, oxygen atom-containing linking groups such as an oxygen atom (an ether bond; —O—), an ester bond (—C(=O)—O—), a carbonyl group (—C(=O)—) and a carbonate group (—O—C(=O)—O—); and combinations of the aforementioned non-hydrocarbon, hetero atom-containing linking groups with an alkylene group.

Examples of such a combination include —$R^{96}$—O— and —$R^{97}$—O—C(=O)— (in the formulas, each of $R^{96}$ and $R^{97}$ independently represents an alkylene group).

The alkylene group for $R^{96}$ and $R^{97}$ is preferably a linear or branched alkylene group, and preferably has 1 to 12 carbon atoms, more preferably 1 to 5, and most preferably 1 to 3. Specific examples include the same alkylene groups as those for $R^{96}$ and $R^{97}$ in $R^{4''}$.

$Q^1$ is preferably a divalent linking group containing an ester bond or an ether bond.

In the group represented by the formula $Z-Q^1-$, the hydrocarbon group for Z is the same as defined for the hydrocarbon group for Z in $R^{4''}$. An aliphatic hydrocarbon group is preferable, and a linear or cyclic aliphatic hydrocarbon, group is more preferable.

Preferable examples of an anion represented by formula (b-4) which has $Z-Q^1-$ as a substituent include anions represented by formulas (b-4-1) to (b-4-11) shown below.

[Chemical Formula 67]

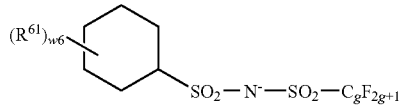

(b-4-1)

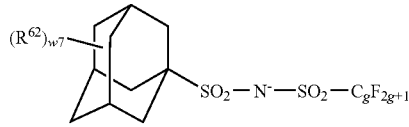

(b-4-2)

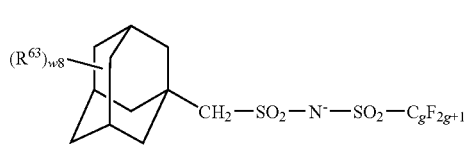

(b-4-3)

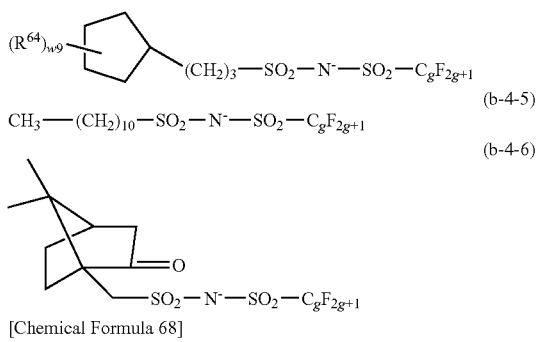

(b-4-4)

(b-4-5)

(b-4-6)

[Chemical Formula 68]

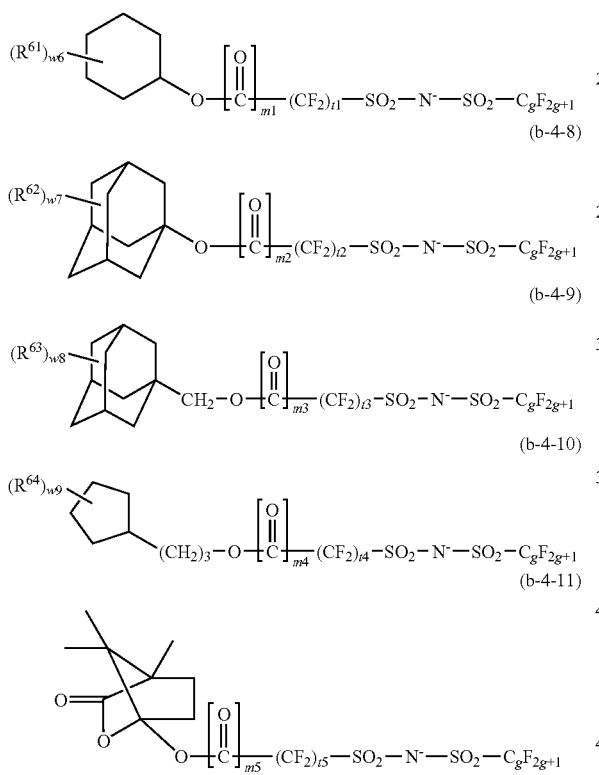

(b-4-7)

(b-4-8)

(b-4-9)

(b-4-10)

(b-4-11)

In the formulas, each g independently represents an integer of 1 to 4; each of t1 to t5 independently represents an integer of 1 to 4; each of $m_1$ to $m_5$ represents 0 or 1; each of w6 to w9 independently represents an integer of 0 to 3; and each of $R^{61}$ to $R^{64}$ independently represents a substituent.

Each g independently represents an integer of 1 to 4, preferably 1 or 2, and most preferably 1.

Each of t1 to t5 independently represents an integer of 1 to 4, preferably 1 or 2, and most preferably 2.

Each of $m_1$ to $m_5$ independently represents 0 or 1, and preferably 0.

Each of w6 to w9 independently represents an integer of 0 to 3, preferably 0 or 1, and most preferably 0.

As the substituent for $R^{61}$ to $R^{64}$, the same substituents as those which an aliphatic hydrocarbon group for Z may have can be mentioned.

If there are two or more of an individual $R^{61}$ to $R^{64}$ group, as indicated by the corresponding value of w6 to w9, then two or more of the individual $R^{61}$ to $R^{64}$ group may be the same or different from each other.

When one of Y" and Z" represents an alkyl group, and the other represents a fluorinated alkyl group, the sulfonyl group bonded to the alkyl group may be substituted with —C(=O)—.

As such an alkyl group, the same alkyl groups as those described above for $R^{4'''}$ can be mentioned, and specific examples of preferable alkyl groups include those which contain a cyclic alkyl group, such as a methyladamantyl group and an adamantyl group.

(Methide Anion)

When X⁻ represents a methide anion, it is preferably an anion represented by general formula (b-c1) shown below.

[Chemical Formula 69]

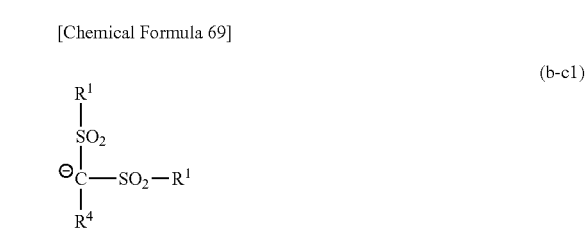

(b-c1)

In the formula, $R^1$ represents an alkyl group of 1 to 10 carbon atoms in which at least one hydrogen atom has been substituted with a fluorine atom; and $R^4$ represents —$SO_2$—$R^1$ a or hydrocarbon group which may have a substituent.

In general formula (b-c1), $R^1$ represents an alkyl group of 1 to 10 carbon atoms in which at least one hydrogen atom has been substituted with a fluorine atom. The alkyl group may be any of linear, branched or cyclic. In the present invention, as $R^1$, a linear or branched alkyl group is preferable, and a linear alkyl group is more preferable.

In general formula (b-c1), when $R^4$ represents a hydrocarbon group which may have a substituent (herein, "a hydrocarbon group which may have a substituent" means that part or all of the hydrogen atoms constituting the hydrocarbon group may be substituted with a substituent), the hydrocarbon group for $R^4$ may be either an aliphatic hydrocarbon group or an aromatic hydrocarbon group. Specifically, the same groups as those described above for Z in the aforementioned formula: Z-$Q^1$- can be mentioned.

As $R^4$, a halogenated aryl group is preferable. For example, an aryl group of 6 to 10 carbon atoms (e.g., a phenyl group, a naphthyl group, or the like) in which part or all of the hydrogen atoms have been substituted with a halogen atom (preferably a fluorine atom) can be mentioned.

(Halogen Anion)

When X⁻ represents a halogen anion, X⁻ preferably represents a fluorine anion, a chlorine anion, a bromine anion or an iodine anion.

In the present invention, among the aforementioned examples, X⁻ is preferably a group represented by general formula (x-1) in which $R^{4'''}$ represents a fluorinated alkyl group which may have a substituent, i.e., a fluorinated alkylsulfonate ion which may have a substituent.

Examples of the fluorinated alkyl group which may have a substituent include alkyl groups for $R^{4'''}$ in which part or all of the hydrogen atoms have been substituted with fluorine atoms. However, in consideration of the fact that an alkyl group or fluorinated alkyl group of 1 to 6 carbon atoms is hardly decomposable, an alkyl group or fluorinated alkyl group of no more than 4 carbon atoms (e.g., nonafluorobutanesulfonate ion) is particularly desirable from the viewpoint of safety in handling in terms of bioaccumulation.

As the component (B1), one type of acid generator may be used alone, or two or more types may be used in combination.

In the component (B), the amount of the component (B1), based on the total weight of the component (B) is preferably 1 to 100% by weight, more preferably 20 to 100% by weight, and still more preferably 50 to 100% by weight.

Further, in the resist composition of the present invention, the total amount of the component (B), relative to 100 parts by weight of the component (A) is preferably 1 to 50 parts by weight, more preferably 3 to 40 parts by weight, and most preferably 3 to 30 parts by weight. When the amount of the component (B) is at least as large as the lower limit of the above-mentioned range, defects can be reduced, and a resist pattern having excellent lithography properties and pattern shape can be formed. On the other hand, when the amount is no more than the upper limit of the above-mentioned range, a uniform solution can be obtained and the storage stability becomes satisfactory.

[Component (B2)]

The resist composition of the present invention may also contain, as the component (B), an acid-generator component other than the aforementioned component (B1) (hereafter, referred to as "component (B2)").

As the component (B2), there is no particular limitation, and any of the known acid generators used in conventional chemically amplified resist compositions can be used. Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators.

As an onium salt acid generator, a compound represented by general formula (b-1) or (b-2) shown below can be used.

[Chemical Formula 70]

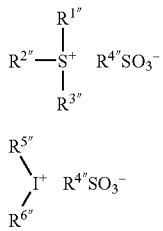

In the formulas, each of $R^{1\prime\prime}$ to $R^{3\prime\prime}$, $R^{5\prime\prime}$ and $R^{6\prime\prime}$ independently represents an aryl group or an alkyl group; in formula (b-1), two of $R^{1\prime\prime}$ to $R^{3\prime\prime}$ may be bonded to each other to form a ring with the sulfur atom; at least one of $R^{1\prime\prime}$ to $R^{3\prime\prime}$ represents an aryl group, and at least one of $R^{5\prime\prime}$ and $R^{6\prime\prime}$ represents an aryl group; and $R^{4\prime\prime}$ is the same as defined above.

In formula (b-1), $R^{1\prime\prime}$ to $R^{3\prime\prime}$ each independently represents an aryl group or an alkyl group. In formula (b-1), two of $R^{1\prime\prime}$ to $R^{3\prime\prime}$ may be bonded to each other to form a ring with the sulfur atom.

Further, among $R^{1\prime\prime}$ to $R^{3\prime\prime}$, at least one group represents an aryl group. Among $R^{1\prime\prime}$ to $R^{3\prime\prime}$, two or more groups are preferably aryl groups, and it is particularly desirable that all of $R^{1\prime\prime}$ to $R^{3\prime\prime}$ are aryl groups.

The aryl group for $R^{1\prime\prime}$ to $R^{3\prime\prime}$ is not particularly limited. For example, an aryl group of 6 to 20 carbon atoms can be used in which part or all of the hydrogen atoms of the aryl group may or may not be substituted with an alkyl group, an alkoxy group, an ether group, a halogen atom, a halogenated alkyl group, a hydroxy group, an alkoxyalkyloxy group, an alkoxycarbonylalkyloxy group, or —$(R^{4\prime})$—C(=O)—$R^{5\prime}$. $R^{4\prime}$ represents an alkylene group of 1 to 5 carbon atoms. $R^{5\prime}$ represents an aryl group. As the aryl group for $R^{5\prime}$, the same aryl groups as those described above for $R^{1\prime\prime}$ to $R^{3\prime\prime}$ can be used. The aryl group is preferably an aryl group having 6 to 10 carbon atoms because it can be synthesized at a low cost. Specific examples thereof include a phenyl group and a naphthyl group.

As the alkyl group, the ether group, the halogen atom and the halogenated alkyl group that may substitute the hydrogen atom(s) within the aforementioned aryl group, the same alkyl group, ether group, halogen atom and halogenated alkyl group as those described above as substituents for the aforementioned aryl group for $R^{7\prime\prime}$ to $R^{9\prime\prime}$ can be mentioned.

Examples of the alkoxyalkyloxy group which may substitute the hydrogen atom(s) within the aforementioned aryl group include groups represented by a general formula shown below:

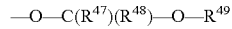

In the formula, $R^{47}$ and $R^{48}$ each independently represents a hydrogen atom or a linear or branched alkyl group; and $R^{49}$ represents an alkyl group.

The alkyl group for $R^{47}$ and $R^{48}$ preferably has 1 to 5 carbon atoms, and may be either linear or branched. As the alkyl group, an ethyl group or a methyl group is preferable, and a methyl group is most preferable.

It is preferable that at least one of $R^{47}$ and $R^{48}$ be a hydrogen atom. It is particularly desirable that at least one of $R^{47}$ and $R^{48}$ be a hydrogen atom, and the other be a hydrogen atom or a methyl group.

The alkyl group for $R^{49}$ preferably has 1 to 15 carbon atoms, and may be linear, branched or cyclic.

The linear or branched alkyl group for $R^{49}$ preferably has 1 to 5 carbon atoms. Examples thereof include a methyl group, an ethyl group, a propyl group, an n-butyl group and a tert-butyl group.

The cyclic alkyl group for $R^{49}$ preferably has 4 to 15 carbon atoms, more preferably 4 to 12, and most preferably 5 to 10.

Specific examples thereof include groups in which one or more hydrogen atoms have been removed from a monocycloalkane or a polycycloalkane such as a bicycloalkane, tricycloalkane or tetracycloalkane, and which may or may not be substituted with an alkyl group of 1 to 5 carbon atoms, a fluorine atom or a fluorinated alkyl group. Examples of the monocycloalkane include cyclopentane and cyclohexane. Examples of polycycloalkanes include adamantane, norbornane, isobornane, tricyclodecane and tetracyclododecane. Among these, a group in which one or more hydrogen atoms have been removed from adamantane is preferable.

Examples of the alkoxycarbonylalkyloxy group which may substitute the hydrogen atom(s) within the aforementioned aryl group include groups represented by a general formula shown below:

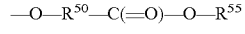

In the formula, $R^{50}$ represents a linear or branched alkylene group, and $R^{55}$ represents a tertiary alkyl group.

The linear or branched alkylene group for $R^{50}$ preferably has 1 to 5 carbon atoms, and examples thereof include a methylene group, an ethylene group, a trimethylene group, a tetramethylene group and a 1,1-dimethylethylene group.

Examples of the tertiary alkyl group for $R^{55}$ include a 2-methyl-2-adamantyl group, a 2-ethyl-2-adamantyl group, a 1-methyl-1-cyclopentyl group, a 1-ethyl-1-cyclopentyl group, a 1-methyl-1-cyclohexyl group, a 1-ethyl-1-cyclohexyl group, a 1-(1-adamantyl)-1-methylethyl group, a 1-(1-adamantyl)-1-methylpropyl group, a 1-(1-adamantyl)-1-methylbutyl group, a 1-(1-adamantyl)-1-methylpentyl group, a 1-(1-cyclopentyl)-1-methylethyl group, a 1-(1-cyclopentyl)-1-methylpropyl group, a 1-(1-cyclopentyl)-1-methylbutyl group, a 1-(1-cyclopentyl)-1-methylpentyl group, a 1-(1-cyclohexyl)-1-methylethyl group, a 1-(1-cyclohexyl)-1-methylpropyl group, a 1-(1-cyclohexyl)-1-methylbutyl group, a 1-(1-cyclohexyl)-1-methylpentyl group, a tert-butyl group, a tert-pentyl group and a tert-hexyl group.

The alkyl group for $R^{1\prime\prime}$ to $R^{3\prime\prime}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

It is particularly desirable that each of $R^{1\prime\prime}$ to $R^{3\prime\prime}$ independently represent a phenyl group or a naphthyl group.

When two of $R^{1\prime\prime}$ to $R^{3\prime\prime}$ in formula (b-1) are bonded to each other to form a ring with the sulfur atom, it is preferable that the two of $R^{1\prime\prime}$ to $R^{3\prime\prime}$ form a 3 to 10-membered ring including the sulfur atom, and it is particularly desirable that the two of $R^{1\prime\prime}$ to $R^{3\prime\prime}$ form a 5 to 7-membered ring including the sulfur atom.

When two of $R^{1\prime\prime}$ to $R^{3\prime\prime}$ in formula (b-1) are bonded to each other to form a ring with the sulfur atom, the remaining one of $R^{1\prime\prime}$ to $R^{3\prime\prime}$ is preferably an aryl group. As examples of the aryl group, the same as the above-mentioned aryl groups for $R^{1\prime\prime}$ to $R^{3\prime\prime}$ can be given.

As preferable examples of the cation moiety for the compound represented by general formula (b-1), those represented by formulas (b-1-1) to (b-1-8) shown below which have a triphenylmethane skeleton may be given.

[Chemical Formula 71]

(b-1-1)

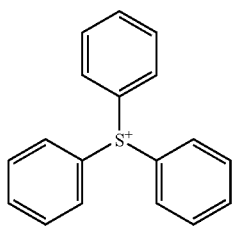

(b-1-2)

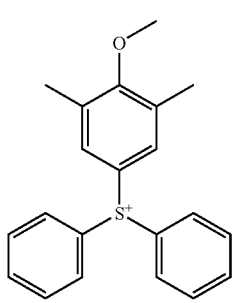

(b-1-3)

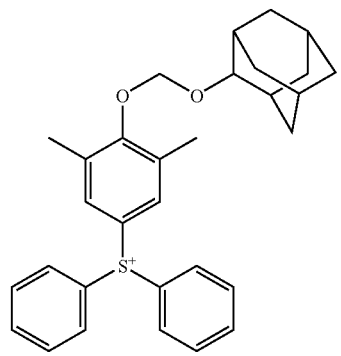

(b-1-4)

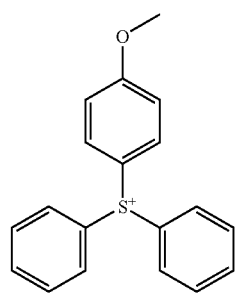

(b-1-5)

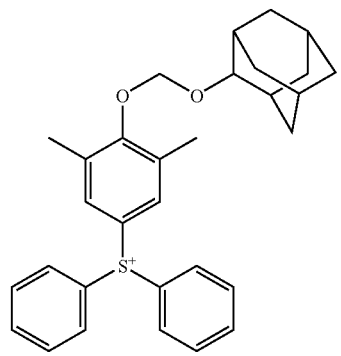

(b-1-6)

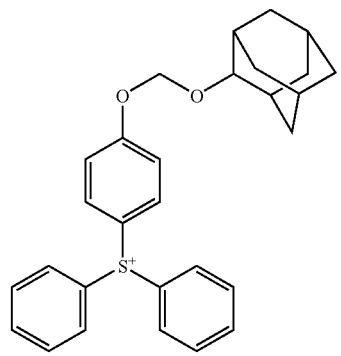

-continued (b-1-7)

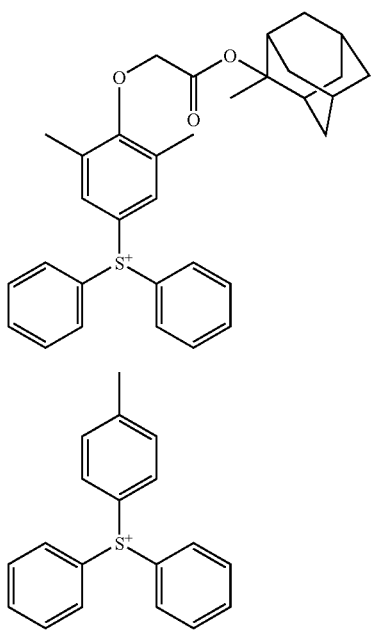

(b-1-8)

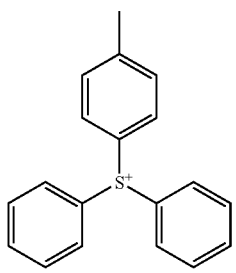

Further, as a cation moiety for an onium salt-based acid generator, any of the cations represented by formulas (b-1-9) and (b-1-10) shown below are also preferable.

In formulas (b-1-9) and (b-1-10) shown below, each of $R^{27}$ and $R^{39}$ independently represents a phenyl group or naphthyl group which may have a substituent, an alkyl group of 1 to 5 carbon atoms, an alkoxy group or a hydroxyl group.

v' is an integer of 1 to 3, and most preferably 1 or 2.

[Chemical Formula 72]

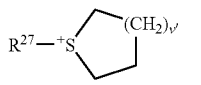
(b-1-9)

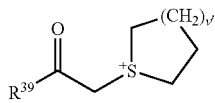
(b-1-10)

In general formula (b-1), $R^{4'''}$ is the same as defined for $R^{4'''}$ in formula (x-1).

In formula (b-2), $R^{5'''}$ and $R^{6'''}$ each independently represent an aryl group or alkyl group. At least one of $R^{5'''}$ and $R^{6'''}$ represents an aryl group. It is preferable that both of $R^{5'''}$ and $R^{6'''}$ represent an aryl group.

As the aryl group for $R^{5'''}$ and $R^{6'''}$, the same as the aryl groups for $R^{1'''}$ to $R^{3'''}$ can be used.

As the alkyl group for $R^{5'''}$ and $R^{6'''}$, the same as the alkyl groups for $R^{1'''}$ to $R^{3'''}$ can be used.

It is particularly desirable that both of $R^{5'''}$ and $R^{6'''}$ represents a phenyl group.

As $R^{4'''}$ in formula (b-2), the same groups as those mentioned above for $R^{4'''}$ in formula (b-1) can be used.

Specific examples of suitable onium salt acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts is replaced by an alkyl sulfonate such as methanesulfonate, n-propanesulfonate, n-butanesulfonate, n-octanesulfonate, 1-adamantanesulfonate, or 2-norbornanesulfonate; or a sulfonate such as d-camphor-10-sulfonate, benzenesulfonate, perfluorobenzenesulfonate, or p-toluenesulfonate.

Further, onium salt-based acid generators in which the anion moiety in general formula (b-1) or (b-2) is replaced by an anion moiety represented by general formula (b-3) or (b-4) (the cation moiety is the same as (b-1) or (b-2)) may also be used.

Further, an onium salt-based acid generator in which the anion moiety ($R^{4'''}SO_3^-$) in general formula (b-1) or (b-2) has been replaced with $R^{10'''}$—$COO^-$ (in the formula, $R^{10'''}$ represents an alkyl group or a fluorinated alkyl group) can also be used (the cation moiety is the same as that in general formula (b-1) or (b-2)).

As $R^{10'''}$, the same groups as those described above for $R^{4'''}$ can be used.

Specific examples of the group represented by the formula "R$^{10"}$—COO$^-$" include a trifluoroacetate ion, an acetate ion, and a 1-adamantanecarboxylic acid ion.

Furthermore, as an onium salt-based acid generator, a sulfonium salt having a cation moiety represented by general formula (b-5) or (b-6) shown below may be used.

[Chemical Formula 73]

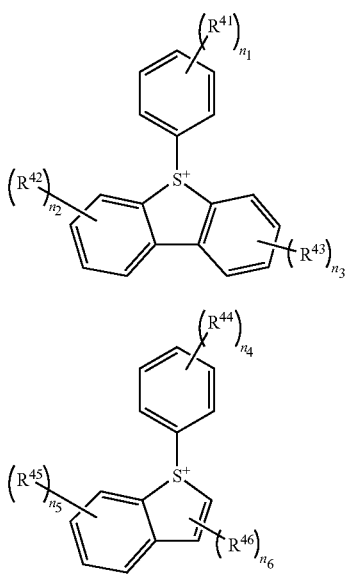

(b-5)

(b-6)

In formulas (b-5) and (b-6) above, each of R$^{41}$ to R$^{46}$ independently represents an alkyl group, an acetyl group, an alkoxy group, a carboxy group, a hydroxyl group or a hydroxyalkyl group; each of $n_1$ to $n_5$ independently represents an integer of 0 to 3; and $n_6$ represents an integer of 0 to 2.

With respect to R$^{41}$ to R$^{46}$, the alkyl group is preferably an alkyl group of 1 to 5 carbon atoms, more preferably a linear or branched alkyl group, and most preferably a methyl group, ethyl group, propyl group, isopropyl group, n-butyl group or tert butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably the aforementioned alkyl group in which one or more hydrogen atoms have been substituted with hydroxy groups, and examples thereof include a hydroxymethyl group, a hydroxyethyl group and a hydroxypropyl group.

If there are two or more of an individual R$^{41}$ to R$^{46}$ group, as indicated by the corresponding value of $n_1$ to $n_6$, then the two or more of the individual R$^{41}$ to R$^{46}$ group may be the same or different from each other.

$n_1$ is preferably 0 to 2, more preferably 0 or 1, and still more preferably 0.

It is preferable that $n_2$ and $n_3$ each independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1, and more preferably 1.

The anion moiety of the sulfonium salt having a cation moiety represented by general formula (b-5) or (b-6) is not particularly limited, and the same anion moieties for onium salt-based acid generators which have been proposed may be used. Examples of such anion moieties include fluorinated alkylsulfonic acid ions such as anion moieties (R$^{4"}$SO$_3^-$) for onium salt-based acid generators represented by general formula (b-1) or (b-2) shown above; and anion moieties represented by general formula (b-3) or (b-4) shown above. Among these, a fluorinated alkylsulfonate ion is preferable, a fluorinated alkylsulfonate ion of 1 to 4 carbon atoms is more preferable, and a linear perfluoroalkylsulfonate ion of 1 to 4 carbon atoms is particularly desirable. Specific examples thereof include a trifluoromethylsulfonate ion, a heptafluoro-n-propanesulfonate ion and a nonafluoro-n-butanesulfonate ion.

In the present description, an oximesulfonate-based acid generator is a compound having at least one group represented by general formula (B-1) shown below, and has a feature of generating acid by irradiation. Such oximesulfonate acid generators are widely used for a chemically amplified resist composition, and can be appropriately selected.

[Chemical Formula 74]

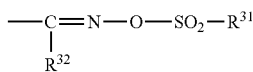

(B-1)

In the formula, each of R$^{31}$ and R$^{32}$ independently represents an organic group.

The organic group for R$^{31}$ and R$^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for R$^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The alkyl group or the aryl group "has a substituent" means that part or all of the hydrogen atoms of the alkyl group or the aryl group is substituted with a substituent.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which part of the hydrogen atoms are substituted with halogen atoms and the "completely halogenated alkyl group" refers to an alkyl group in which all of the hydrogen atoms are substituted with halogen atoms. Examples of halogen atoms include fluorine atoms, chlorine atoms, bromine atoms and iodine atoms, and fluorine atoms are particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. Examples of the alkyl group and the aryl group for $R^{32}$ include the same alkyl groups and aryl groups as those described above for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate acid generator include compounds represented by general formula (B-2) or (B-3) shown below.

[Chemical Formula 75]

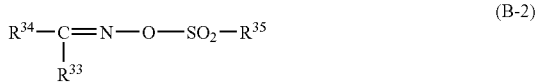

(B-2)

In the formula, $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 76]

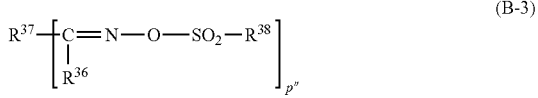

(B-3)

In the formula, $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. Further, the halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), as the alkyl group having no substituent and the halogenated alkyl group for $R^{36}$, the same alkyl group having no substituent and the halogenated alkyl group described above for $R^{33}$ can be used.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate acid generators disclosed in Japanese Unexamined Patent Application, First Publication No. Hei 9-208554 (Chemical Formulas 18 and 19 shown in paragraphs [0012] to [0014]) and oxime sulfonate acid generators disclosed in WO 2004/074242A2 (Examples 1 to 40 described at pages 65 to 85) may be preferably used.

Furthermore, as preferable examples, the following can be used.

[Chemical Formula 77]

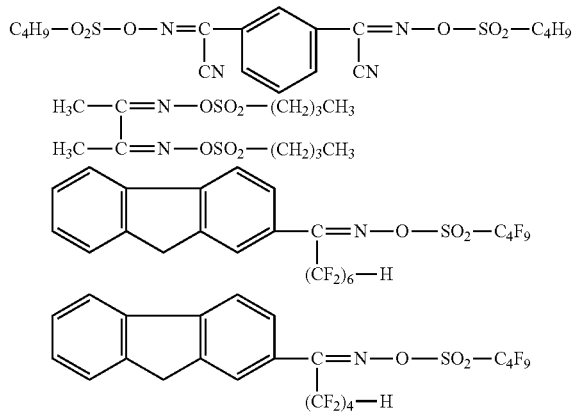

Of the aforementioned diazomethane acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as examples of poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be given.

As the component (B2), one type of acid generator may be used, or two or more types of acid generators may be used in combination.

The amount of the component (B) within the resist composition according to the present invention is preferably from 0.5 to 50 parts by weight, and more preferably from 1 to 40 parts by weight, relative to 100 parts by weight of the component (A). When the amount of the component (B) is within the above-mentioned range, formation of a resist pattern can be satisfactorily performed. Further, by virtue of the above-mentioned range, a uniform solution can be obtained and the storage stability becomes satisfactory.

<Optional Components>

[Component (D)]

It is preferable that the resist composition of the present invention further includes a nitrogen-containing organic compound (D) (hereafter referred to as the component (D)) as an optional component.

As the component (D), there is no particular limitation as long as it functions as an acid diffusion control agent, i.e., a quencher which traps the acid generated from the component (B) upon exposure. A multitude of these components (D) have already been proposed, and any of these known compounds may be used, although an aliphatic amine, and particularly a secondary aliphatic amine or tertiary aliphatic amine is preferable. The term "aliphatic cyclic group" refers to a monocyclic group or polycyclic group that has no aromaticity. An aliphatic amine is an amine having one or more aliphatic groups, and the aliphatic groups preferably have 1 to 20 carbon atoms.

Examples of these aliphatic amines include amines in which at least one hydrogen atom of ammonia ($NH_3$) has been substituted with an alkyl group or hydroxyalkyl group of no more than 20 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, tri-n-octanolamine, stearyldiethanolamine and laurildiethanolamine. Among these, trialkylamines and/or alkylalcoholamines are preferable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of aromatic amines include aniline, pyridine, 4-dimethylaminopyridine, pyrrole, indole, pyrazole, imidazole and derivatives thereof, as well as diphenylamine, triphenylamine and tribenzylamine.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris {2-(1-ethoxyethoxy)ethyl}amine, tris{2-(1-ethoxypropoxy)ethyl}amine and tris[2-{2-(2-hydroxyethoxy)ethoxy}ethyl]amine.

These compounds can be used either alone, or in combinations of two or more different compounds.

In the present invention, of the various possibilities, a trialkylamine can be preferably used as the component (D).

The component (D) is typically used in an amount within a range from 0.01 to 5.0 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

[Component (E)]

Furthermore, in the resist composition for immersion exposure according to the present invention, for preventing any deterioration in sensitivity, and improving the resist pattern shape and the post exposure stability of the latent image formed by the pattern-wise exposure of the resist layer, at least one compound (E) (hereafter referred to as "component (E)") selected from the group consisting of organic carboxylic acids, and phosphorus oxo acids and derivatives thereof can be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

As the component (E), an organic carboxylic acid is preferred, and salicylic acid is particularly desirable.

The component (E) is typically used in an amount within a range from 0.01 to 5.0 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

[Component (S)]

The resist composition of the present invention can be prepared by dissolving the materials for the resist composition in an organic solvent (hereafter, referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

These solvents can be used individually, or in combination as a mixed solvent.

Among these, propylene glycol monomethyl ether acetate (PGMEA), propylene glycol monomethyl ether (PGME) and ethyl lactate (EL) and γ-butyrolactone are preferable.

Further, among the mixed solvents, a mixed solvent obtained by mixing PGMEA or PGME with a polar solvent is preferable. The mixing ratio (weight ratio) of the mixed solvent can be appropriately determined, taking into consideration the compatibility of the PGMEA or PGME with the polar solvent, but is preferably in a range from 1:9 to 9:1, and more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

Furthermore, a mixed solvent of PGME and dimethylsulfoxide is also preferable. In this case, the mixing ratio (former:latter) of such a mixed solvent is preferably from 9:1 to 1:9, more preferably from 8:2 to 2:8, and most preferably from 7:3 to 5:5.

The amount of the component (S) is not particularly limited, and is adjusted appropriately to a concentration that enables application of a coating solution to a substrate in accordance with the thickness of the coating film. In general, the component (S) is used in an amount that yields a solid content for the resist composition that is within a range from 0.5 to 20% by weight, and preferably from 1 to 15% by weight.

Dissolving of the materials for a resist composition in the component (S) can be conducted by simply mixing and stirring each of the above components together using conventional methods, and where required, the composition may also be mixed and dispersed using a dispersion device such as a dissolver, a homogenizer, or a triple roll mill. Furthermore, following mixing, the composition may also be filtered using a mesh, or a membrane filter or the like.

The resist composition of the present invention described above is a novel composition essentially unknown in the art.

According to the resist composition of the present invention, an excellent solubility in a developing solution, excellent lithography properties and an excellent resist pattern shape can be achieved. Especially, due to the high solubility of the component (B1) in an alkali developing solution after exposure, there is a low risk of the component (B1) precipitating, thereby enabling the formation of a resist pattern with reduced defects. The reason why these effects can be achieved has not been elucidated yet, but is presumed as follows.

In the resist composition of the present invention, an acid generator (B1) including a compound having a cation moiety comprising a group represented by general formula (I) is used. In the component (B1), by the action of an alkali developing solution (aqueous alkali solution), the single bond of C—O within "—C(=O)—O—" in the group represented by general formula (I) is broken (hydrolyzed), and "—O—$R^5$" is dissociated from the cation moiety of the component (B1). As a result, a carboxylic acid having a terminal "—O-Q-C (=O)—OH" and an alcohol "HO—$R^5$" are generated. Since the generated carboxylic acid and alcohol exhibit high solubility in an alkali developing solution, with respect to the component (B1) after development, possibility of risks such as precipitating, not dissolving completely, and adhering becomes low, as compared to a conventional acid generator. For this reason, it is presumed that the aforementioned effects can be achieved.

Further, the resist composition of the present invention is capable of forming a line and space pattern having a high rectangularity or a contact hole pattern exhibiting excellent circularity and in-plane uniformity (CDU). Therefore, a resist pattern having an excellent shape can be formed in both of the case of a line and space pattern and the case of a contact hole pattern. Furthermore, the resist composition of the present invention exhibits excellent properties with respect to line width roughness (LWR), exposure latitude (EL margin), mask error factor (MEF) and depth of focus (DOF). In addition, the resist composition of the present invention exhibits excellent properties with respect to both of the EL margin and the DOF, and hence, the process window is large. Therefore, by using the resist composition of the present invention, the process margin during the formation of a resist pattern is improved.

The reason why these effects can be achieved has not been elucidated yet, but is presumed as follows.

In the component (B1), the group represented by general formula (I) contains an organic group having a carbonyl group, an ester bond or a sulfonyl group. Since the component (B1) has a carbonyl group, an ester bond or a sulfonyl group, an interaction is likely to occur between the group and a highly polar portion within the component (A), thereby enhancing the affinity of the component (B1) for the base component (A). As a result, the compatibility of the component (B1) with the base component (A) is improved, and the component (B1) can be more uniformly distributed within the resist film. By virtue of the component (B1) being uniformly distributed within the resist film and the component (B1) exhibiting an excellent solubility in an alkali developing solution, it is presumed that the resist composition of the present invention enables formation of a resist pattern with excellent shape and excellent lithography properties.

"LWR" refers to the non-uniformity of the line widths of a line pattern, and improvement in this characteristic becomes more important as the pattern becomes finer.

The larger the value of the "EL margin", the smaller the change in the pattern size by the variation of the exposure dose, meaning that the process margin is high.

The MEF is a parameter that indicates how faithfully mask patterns of differing dimensions can be reproduced by using the same exposure dose with fixed pitch and changing the mask size (i.e., mask reproducibility).

DOF is the range of depth of focus in which a resist pattern having a predetermined size within the range corresponding to the target size can be formed when the exposure focus is moved upwardly or downwardly with the same exposure dose, i.e., the range in which a resist pattern faithful to the mask pattern can be obtained. Larger DOF is more preferable.

<<Method of Forming a Resist Pattern>>

The method of forming a resist pattern according to the present invention includes: applying a resist composition of the present invention to a substrate to form a resist film on the substrate; conducting exposure of the resist film; and alkali-developing the resist film to form a resist pattern.

More specifically, the method for forming a resist pattern according to the present invention can be performed, for example, as follows.

More specifically, the method for forming a resist pattern according to the present invention can be performed, for example, as follows. Firstly, a resist composition of the present invention is applied onto a substrate using a spinner or the like, and a prebake (post applied bake (PAB)) is conducted under temperature conditions of 80 to 150° C. for 40 to 120 seconds, preferably 60 to 90 seconds to form a resist film. Then, for example, using an ArF exposure apparatus or the like, the resist film is selectively exposed with an ArF exposure apparatus, an electron beam exposure apparatus, an EUV exposure apparatus or the like through a mask pattern or directly irradiated with electron beam without a mask pattern, followed by post exposure bake (PEB) under temperature conditions of 80 to 150° C. for 40 to 120 seconds, preferably 60 to 90 seconds. Subsequently, developing is conducted using an alkali developing solution such as a 0.1 to 10% by weight aqueous solution of tetramethylammonium hydroxide (TMAH), preferably followed by rinsing with pure water, and drying. If desired, bake treatment (post bake) can be conducted following the developing. In this manner, a resist pattern that is faithful to the mask pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) can be used.

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays. The positive resist composition of the present invention is effective to KrF excimer laser, ArF excimer laser, EB and EUV, and particularly effective to ArF excimer laser, EB or EUV.

The exposure of the resist film can be either a general exposure (dry exposure) conducted in air or an inert gas such as nitrogen, or immersion exposure (immersion lithography).

In immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

The method of forming a resist pattern according to the present invention is also applicable to a double exposure method or a double patterning method.

<<Compound>>

The compound according to a third aspect of the present invention is a compound represented by the aforementioned general formula (b1-11) (hereafter, this compound is referred to as "compound (b1-11)").

The compound (b1-11) is the same as the component (B1) for the resist composition according to the first aspect of the present invention.

The compound (b1-11) can be produced by a normal method.

Specifically, for example, when $R^{7''}$ represents an aryl group having one group represented by general formula (I), such a compound (hereafter, referred to as "compound (b1-11-a1)" or "compound (b1-11-a2)") can be produced as follows.

Firstly, for example, a compound represented by general formula (b1-01) shown below and a compound represented by general formula (b1-02) shown below are added to and reacted in a solution of an organic acid $H^+V^-$ ($V^-$ represents an anion moiety of an organic acid, such as a methanesulfonate ion, p-toluenesulfonate or benzenesulfonate). Then, pure water and an organic solvent (e.g., dichloromethane, tetrahydrofuran, or the like) are added thereto, and the organic phase is collected. From the organic phase, a compound represented by general formula (b1-03) is collected.

[Chemical Formula 78]

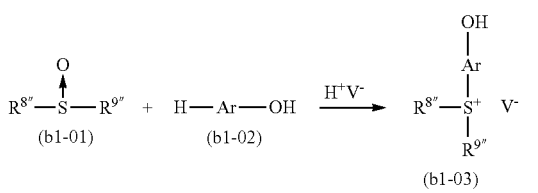

(b1-03)

Subsequently, the compound represented by general formula (b1-03) is added to an organic solvent (e.g., acetone, dichloromethane, tetrahydrofuran, or the like), followed by cooling. Then, a compound represented by general formula (b1-04) shown below is added thereto and reacted, followed by liquid separation and washing with water. From the resulting organic phase, a compound represented by general formula (b1-05) shown below is obtained.

Thereafter, an acid (hydrochloric acid, sulfuric acid, p-toluenesulfonic acid or the like) is added to the compound represented by general formula (b1-05) to cause dissociation of $—R^x$ (deprotection), thereby obtaining a compound represented by general formula (b1-06) shown below.

[Chemical Formula 79]

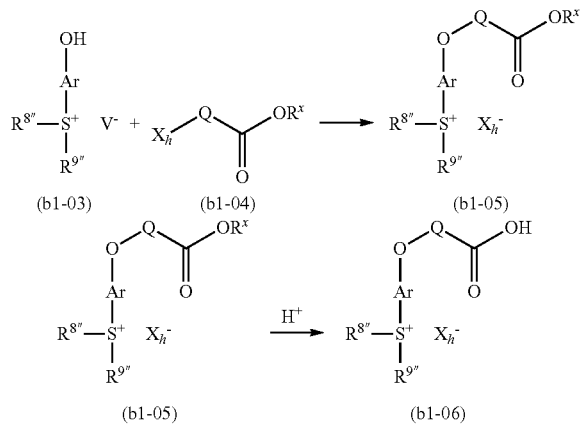

Next, the compound represented by general formula (b1-06) is dissolved in an organic solvent (dichloromethane, tetrahydrofuran, or the like), and $R^5$—OH is added thereto to effect a reaction in the presence of a base, optionally using a condensing agent. The resultant is subjected to liquid separation and washing with water, and a compound (b1-11-a1) is collected from the organic phase.

Further, in the case of performing salt exchanging, the compound (b1-11-a1) is dissolved in a mixed solvent containing an organic solvent (e.g., dichloromethane, tetrahydrofuran, or the like) and water, and a salt $L^+X^-$ containing a desired anion $X^-$ ($L^+$ represents an alkali metal cation such as a lithium ion, a sodium ion or a potassium ion, or an organic ammonium ion such as a tetraethylammonium ion) is added thereto to effect a reaction. The resultant is subjected to liquid separation and washing with water, and a compound (b1-11-a2) is collected from the organic phase.

[Chemical Formula 80]

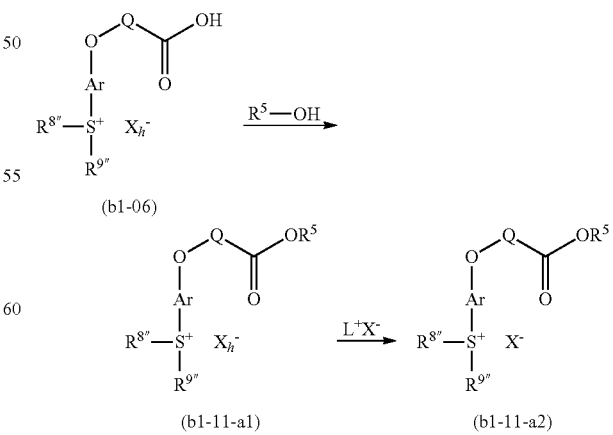

In the formulas above, $R^{8''}$, $R^{9''}$, $R^5$, Q and $X^-$ are the same as defined above, Ar represents an arylene group, $V^-$ represents an anion moiety of an organic acid, L⁺ represents an alkali metal cation or an organic ammonium ion, $X_h$ represents a halogen atom, and $R^x$ represents a protection group.

As the arylene group for Ar, a group in which one hydrogen atom has been removed from an aryl group for $R^{7''}$ to $R^{9''}$ which may have a substituent can be mentioned.

The halogen atom for $X_h$ is preferably a bromine atom or a chlorine atom.

The protection group for $R^x$ is not particularly limited, as long as it is an organic group which can be subjected to deprotection by hydrolysis. For example, when hydrolysis is performed under acidic conditions, the aforementioned acid dissociable, dissolution inhibiting group for the structural unit (a1) can be used.

The structure of the thus obtained compound can be confirmed by a general organic analysis method such as ¹H-nuclear magnetic resonance (NMR) spectrometry, ¹³C-NMR spectrometry, ¹⁹F-NMR spectrometry, infrared absorption (IR) spectrometry, mass spectrometry (MS), elementary analysis and X-ray diffraction analysis.

The compound (b1-11) described above is a novel compound essentially unknown in the art.

Further, the compound (b1-11) is a novel compound useful as an acid generator for a resist composition, and can be blended in a resist composition as an acid generator.

<<Acid Generator>>

The acid generator according to a fourth aspect of the present invention is an acid generator including the compound (b1-11).

The acid generator is useful for a chemically amplified resist composition, for example, the acid-generator component (B) of the resist composition according to the first aspect of the present invention.

EXAMPLES

As follows is a description of examples of the present invention, although the scope of the present invention is by no way limited by these examples.

In the following examples, a compound represented by a chemical formula (1) is designated as "compound (1)", and the same applies for compounds represented by other formulas.

<Synthesis of Acid-Generator Component (B)>

Examples 1 to 96

The compounds used as the acid-generator component (B) in the present examples were synthesized in accordance with the following synthesis examples.

Example 1

Synthesis of Compound (B1-1)

(i) Synthesis Example of Compound (2)

16.0 g of a compound (1) and 131.7 g of pure water were added to a three-necked flask, and 5.20 g of hydrochloric acid was dropwise added. Then, reflux was conducted while heating for 12 hours. The water phase was washed with 131.7 g of t-butylmethylether (TBME), thereby obtaining 10.0 g of a compound (2).

The obtained compound (2) was analyzed by NMR.

¹H-NMR (DMSO-d-6,400 MHz): δ(ppm)=2.30 (d, 6H, Ha), 4.53 (s, 2H, Hb), 7.59 (s, 2 H, Ar), 7.71-7.89 (m, 10H, Ar)

From the results shown above, it was confirmed that the compound (2) had a structure shown below.

[Chemical Formula 81]

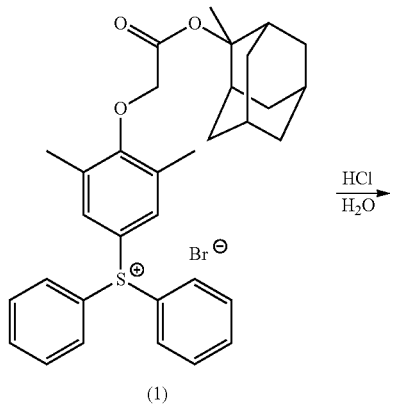

(1)

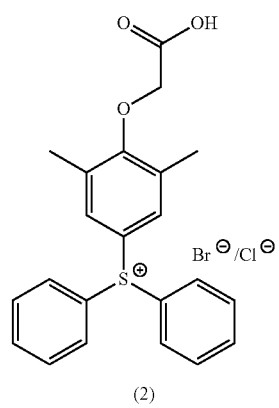

(2)

(ii) Synthesis Example of Compound (B1-1)

10 g of the compound (2) and 100 g of dichloromethane were added to a three-necked flask in a nitrogen atmosphere, and cooled to 5° C. or lower. Then, 0.56 g of N,N-dimethylaminopyridine (DMAP) was added thereto, followed by stirring at 5° C. or lower for 5 minutes. Next, 4.8 g of ethyl-N,N-dimethylaminopropylcarbodiimide was added thereto. Thereafter, stirring was conducted for 10 minutes, and 3.5 g of a compound (3) was added thereto. Then, the temperature of the resultant was elevated to room temperature, and stirring was conducted at room temperature for 15 hours, followed by washing with a diluted hydrochloric acid and pure water. The resulting organic phase was dropwise added to 1,100 g of n-hexane and precipitated, thereby obtaining 10.9 g of a compound (B1-1).

The obtained compound (B1-1) was analyzed by NMR.

¹H-NMR (DMSO-d6,400 MHz): δ(ppm)=7.72-7.83 (m, 10H, ArH), 7.59 (s, 2H, ArH), 4.90 (m, 1H, sultone), 4.62-4.68 (m, 3H, CH₂+sultone), 3.83-3.89 (m, 1H, sultone), 3.43 (m, 1H, sultone), 1.75-2.49 (m, 11H, CH₃+sultone)

From the results shown above, it was confirmed that the compound (B1-1) had a structure shown below.

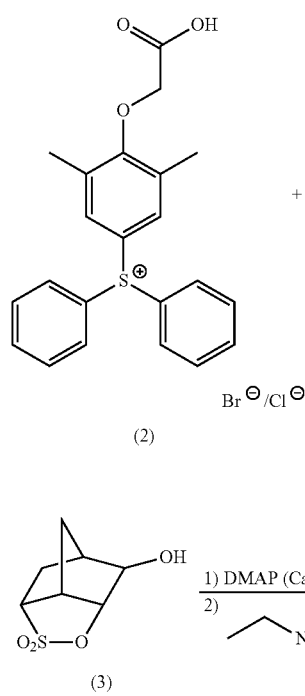

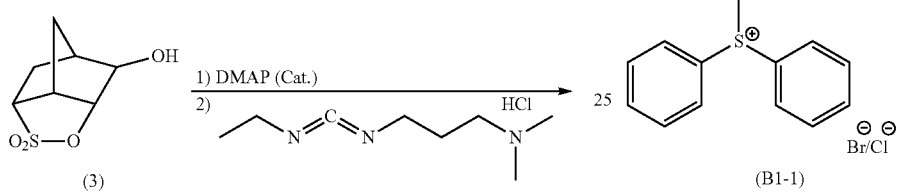

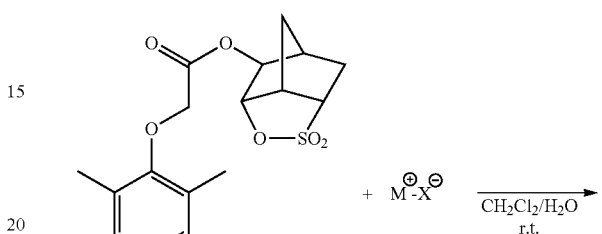

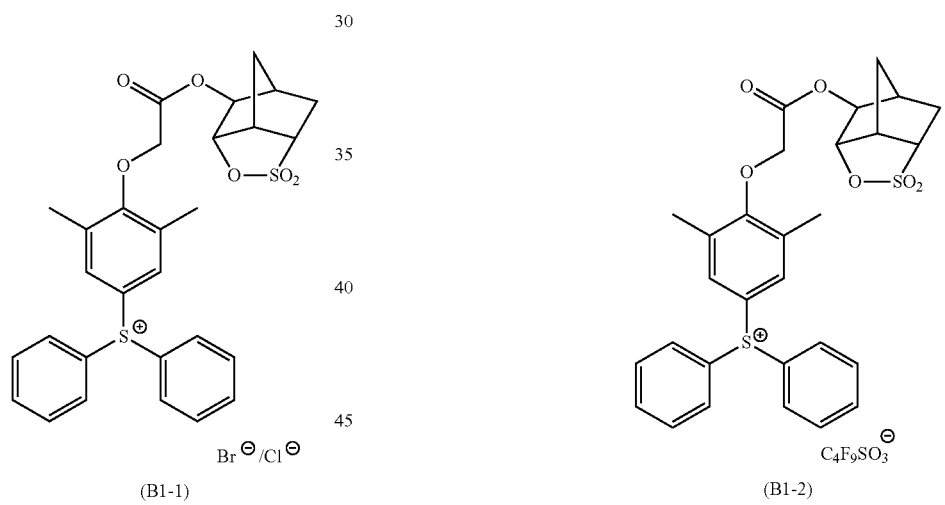

4.68 (m, 3H, CH$_2$+sultone), 3.83-3.89 (m, 1H, sultone), 3.43 (m, 1H, sultone), 1.75-2.49 (m, 11H, CH$_3$+sultone)

$^{19}$F-NMR (DMSO-d6,376 MHz): δ(ppm)=−77.3, −111.5, −118.1, −122.4

From the results shown above, it was confirmed that the compound (B1-2) had a structure shown below.

Example 2

Synthesis of Compound (B1-2)

2.2 g of a compound (B1-1), 13.8 g of dichloromethane and 5.2 g of pure water were mixed together, and 1.7 g of potassium perfluorobutanesulfonate was added thereto, followed by stirring at room temperature for one night. Then, the organic phase was separated and washed with 5.2 g of pure water four times. Thereafter, dichloromethane was distilled off under reduced pressure, and the resultant was dried under reduced pressure, thereby obtaining 2.4 g of a compound (B1-2).

The obtained compound (B1-2) was analyzed by NMR.

$^1$H-NMR (DMSO-d6,400 MHz): δ(ppm)=7.72-7.83 (m, 10H, ArH), 7.59 (s, 2H, ArH), 4.90 (m, 1H, sultone), 4.62-

Examples 3 to 24

The same procedure as in Example 2 was performed, except that the compound (M$^+$-X$^-$) was changed to a compound shown in Tables 1 to 6 (equimolar amount). In this manner, products having an anion and a cation as shown in Tables 1 to 6 (compounds (B1-3) to (B1-24)) were obtained.

Each of the obtained compounds were analyzed by NMR. The results are shown in Tables 1 to 6. In Tables 1 to 6, "↑" indicates that the cation of the product is the same as that of the compound (B1-3).

TABLE 1

| Compound | NMR | Compound $M^+$-$X^-$ |
|---|---|---|
| B1-3 | $^1$H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 3.83-3.89(m, 1H, sultone), 3.43(m, 1H, sultone), 1.75-2.49(m, 11H, CH3 + sultone) $^{19}$F-NMR(DMSO-d6, 376 MHz): δ(ppm) = −75.0 | $CF_3SO_3^{\ominus}$ $K^{\oplus}$ |
| B1-4 | $^1$H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 3.83-3.89(m, 1H, sultone), 3.43(m, 1H, sultone), 1.75-2.49(m, 11H, CH3 + sultone) $^{19}$F-NMR(DMSO-d6, 376 MHz): δ(ppm) = −77.3, −112.5, −121.7 | $C_3F_7SO_3^{\ominus}$ $K^{\oplus}$ |
| B1-5 | $^1$H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 3.83-3.89(m, 1H, sultone), 3.43(m, 1H, sultone), 1.75-2.49(m, 11H, CH3 + sultone) $^{19}$F-NMR(DMSO-d6, 376 MHz): δ(ppm) = −116.9, −123.0 | 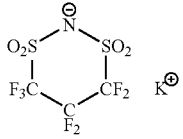 $K^{\oplus}$ |
| B1-6 | $^1$H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 3.83-3.89(m, 1H, sultone), 3.43(m, 1H, sultone), 1.75-2.49(m, 11H, CH3 + sultone) $^{19}$F-NMR(DMSO-d6, 376 MHz): δ(ppm) = −75.9, −76.0, −114.7 | 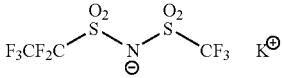 $K^{\oplus}$ |

| | Product | |
|---|---|---|
| Compound | Cation | Anion |
| B1-3 | 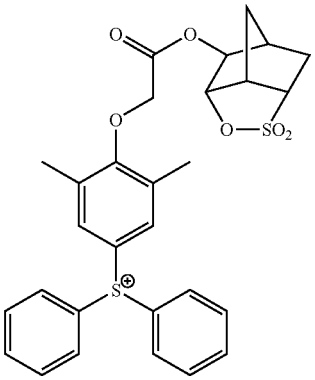 | $CF_3SO_3^{\ominus}$ |
| B1-4 | ↑ | $C_3F_7SO_3^{\ominus}$ |
| B1-5 | ↑ | 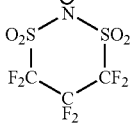 |
| B1-6 | ↑ | 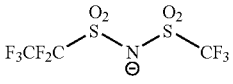 |

TABLE 2

| Compound | NMR | Compound M⁺-X⁻ |
|---|---|---|
| B1-7 | ¹H-NMR(DMSO-d6, 400 MHz): δ(ppm) = 7.72-7.83(m, 10H, ArH), 7.59(s, 2H, ArH), 5.83-5.92(m, 1H, anion CH), 5.41(dd, 1H, anion CH), 5.21(dd, 1H, anion CH), 4.90(m, 1H, sultone), 4.62-4.68(m, 3H, CH2 + sultone), 4.45(s, 2H, anion CH2), 3.83-3.89(m, 1H, sultone), 3.43(m, 1H, sultone), 1.75-2.49(m, 11H, CH3 + sultone)<br>¹⁹F-NMR(DMSO-d6, 376 MHz): δ(ppm) = −80.0, −113.0 | allyl-O-CF₂-CF₂-SO₃⁻  Li⁺ |
| B1-8 | ¹H-NMR(DMSO-d6, 400 MHz): δ(ppm) = 7.51-7.96(m, 19H, Naph + ArH), 5.20(s, 2H, CH2), 4.90(m, 1H, sultone), 4.62-4.68(m, 3H, CH2 + sultone), 3.83-3.89(m, 1H, sultone), 3.43(m, 1H, sultone), 1.75-2.49(m, 11H, CH3 + sultone)<br>¹⁹F-NMR(DMSO-d6, 376 MHz): δ(ppm) = −80.5, −113.7 | naphthyl-CH₂-O-CF₂-CF₂-SO₃⁻  Li⁺ |
| B1-9 | ¹H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 3.83-3.89(m, 1H, sultone), 3.43(m, 1H, sultone), 1.75-2.49(m, 26H, CH3 + sultone + adamantane)<br>¹⁹F-NMR(DMSO-d6, 376 MHz): δ(ppm) = −70.1, −113.4 | adamantyl-O-CF₂-CF₂-SO₃⁻  Li⁺ |

| | Product | |
|---|---|---|
| Compound | Cation | Anion |
| B1-7 | ↑ | allyl-O-CF₂-CF₂-SO₃⁻ |
| B1-8 | ↑ | naphthyl-CH₂-O-CF₂-CF₂-SO₃⁻ |
| B1-9 | ↑ | adamantyl-O-CF₂-CF₂-SO₃⁻ |

TABLE 3

| Compound | NMR | Compound M⁺-X⁻ |
|---|---|---|
| B1-10 | ¹H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 3.83-3.89(m, 1H, sultone), 3.43(m, 1H, sultone), 1.75-2.49(m, 11H, CH3 + sultone)<br>¹⁹F-NMR(DMSO-d6, 376 MHz): δ(ppm) = −73.7 | (F₃CO₂S)(CF₃O₂S)C⁻(SO₂CF₃)  H⁺ |
| B1-11 | ¹H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 3.83-3.89(m, 1H, sultone), 3.43(m, 1H, sultone), 1.75-2.49(m, 11H, CH3 + sultone)<br>¹⁹F-NMR(DMSO-d6, 376 MHz): δ(ppm) = −161.1, −149.7, −131.6, −76.2 | pentafluorophenyl-C⁻(SO₂CF₃)(SO₂CF₃)  H⁺ |
| B1-12 | ¹H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 3.83-3.89(m, 1H, sultone), 3.43(m, 1H, sultone), 1.75-2.49(m, 26H, CH3 + sultone + adamantane)<br>¹⁹F-NMR(DMSO-d6, 376 MHz): δ(ppm) = −74.5 | adamantyl-C(=O)-N⁻-SO₂CF₃  Na⁺ |

TABLE 3-continued

| Compound | Product Cation | Anion |
|---|---|---|
| B1-10 | ↑ | C(SO₂CF₃)₃ anion (tris(trifluoromethylsulfonyl)methide) |
| B1-11 | ↑ | pentafluorophenyl-C(SO₂CF₃)₂ anion |
| B1-12 | ↑ | adamantane-C(O)-N⁻-SO₂CF₃ |

TABLE 4

| Compound | NMR | Compound M⁺-X⁻ |
|---|---|---|
| B1-13 | ¹H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 4.19(s, 2H, CH2), 3.83-3.89(m, 1H, sultone), 3.43(m, 1H, sultone), 1.55-2.49(m, 26H, CH3 + sultone + adamantane)<br>¹⁹F-NMR(DMSO-d6, 376 MHz): δ(ppm) = −77.7 | adamantyl-CH₂-C(O)-N⁻-SO₂CF₃ Na⁺ |
| B1-14 | ¹H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 3.83-3.89(m, 1H, sultone), 3.43(m, 1H, sultone), 2.77-2.81(m, 1H, cyclohexyl), 1.73-2.49(m, 15H, CH3 + sultone + cyclohexyl), 1.56-1.59(m, 1H, cyclohexyl), 1.07-1.33(m, 5H, cyclohexyl)<br>¹⁹F-NMR(DMSO-d6, 376 MHz): δ(ppm) = −74.7 | cyclohexyl-SO₂-N⁻-SO₂CF₃ Na⁺ |
| B1-15 | ¹H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 3.83-3.89(m, 1H, sultone), 3.43(m, 1H, sultone), 1.59-2.49(m, 26H, CH3 + sultone + adamantane)<br>¹⁹F-NMR(DMSO-d6, 376 MHz): δ(ppm) = −69.2, −76.0, −112.9 | adamantyl-O-CF₂-CF₂-SO₂-N⁻-SO₂CF₃ Na⁺ |
| B1-16 | ¹H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 3.83-3.89(m, 1H, sultone), 3.43(m, 1H, sultone), 2.88(d, 1H, CH), 2.68-2.74(m, 1H, CH), 1.75-2.49(m, 16H, CH3 + sultone + anion CH), 1.22-1.29(m, 2H, anion CH2), 1.03(s, 3H, anion CH3), 0.71(s, 3H, CH3) | camphorsulfonate anion Na⁺ H⁺ |

| Compound | Product Cation | Anion |
|---|---|---|
| B1-13 | ↑ | adamantyl-CH₂-C(O)-N⁻-SO₂CF₃ |

TABLE 4-continued

| | | |
|---|---|---|
| B1-14 | ↑ | 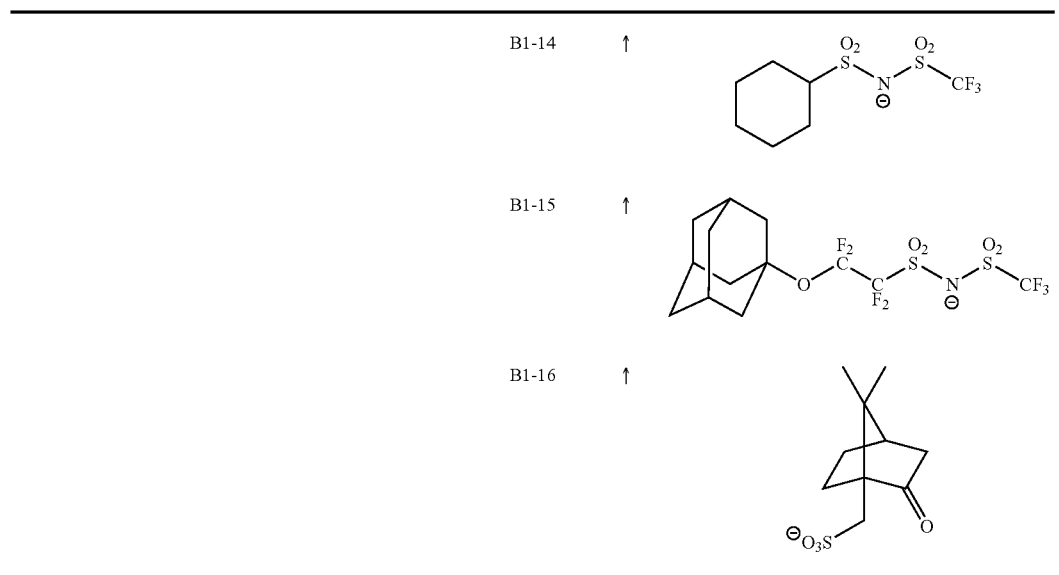 |
| B1-15 | ↑ | |
| B1-16 | ↑ | |

TABLE 5

| Compound | NMR | Compound M⁺-X⁻ |
|---|---|---|
| B1-17 | $^1$H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 4.40-4.50(m, 4H, CH2), 3.83-3.89(m, 1H, sultone), 3.43(m, 1H, sultone), 1.75-2.49(m, 11H, CH3 + sultone)<br>$^{19}$F-NMR(DMSO-d6, 376 MHz): δ(ppm) = −106.7, −154.0, −160.0-161.5 | |
| B1-18 | $^1$H-NMR(DMSO-d6, 400 MHz): δ(ppm) = 8.74-8.82(m, 2H, Py-H), 7.72-7.84(m, 12H, ArH + Py-H), 7.59(s, 2H, ArH), 4.90(m, 1H, sultone), 4.54-4.68(m, 7H, CH2 + sultone + anion, CH2CH2), 3.83-3.89(m, 1H, sultone), 3.43(m, 1H, sultone), 1.75-2.49(m, 11H, CH3 + sultone)<br>$^{19}$F-NMR(DMSO-d6, 376 MHz): δ(ppm) = −106.5 | |
| B1-19 | $^1$H-NMR(DMSO-d6, 400 MHz): δ(ppm) = 7.72-7.83(m, 10H, ArH), 7.59(s, 2H, ArH), 5.46(t, 1H, oxo-norbornane), 4.97(s, 1H, oxo-norborname), 4.90(m, 1H, sultone), 4.71(d, 1H, oxo-norbornane), 4.62-4.68(m, 3H, CH2 + sultone), 4.51(d, 1H, oxo-norbornane), 3.83-3.89(m, 1H, sultone), 3.43(m, 1H, sultone), 2.69-2.73(m, 1H, oxo-norbornane), 1.75-2.49(m, 13H, CH3 + sultone + oxo-norbornane)<br>$^{19}$F-NMR(DMSO-d6, 376 MHz): δ(ppm) = −107.1 | |
| B1-20 | $^1$H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 4.41(t, 2H, CH2), 4.23(t, 2H, CH2), 3.83-3.89(m, 1H, sultone), 3.43(m, 1H, sultone), 0.79-2.89(m, 32H, CH3 + sultone + undecanoyl)<br>$^{19}$F-NMR(DMSO-d6, 376 MHz): δ(ppm) = −106.8 | |

TABLE 5-continued

| Compound | Product Cation | Product Anion |
|---|---|---|
| B1-17 | ↑ | Pentafluorophenyl-O-CH2CH2-O-C(=O)-CF2-SO3⁻ |
| B1-18 | ↑ | Isonicotinoyl-O-CH2CH2-O-C(=O)-CF2-SO3⁻ |
| B1-19 | ↑ | Norbornane lactone-O-C(=O)-CF2-SO3⁻ |
| B1-20 | ↑ | CH3(CH2)9-C(=O)-O-CH2CH2-O-C(=O)-CF2-SO3⁻ |

TABLE 6

| Compound | NMR | Compound M⁺-X⁻ |
|---|---|---|
| B1-21 | ¹H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 4.40(t, 2H, CH2), 4.21(t, 2H, CH2), 3.83-3.89(m, 1H, sultone), 3.43(m, 1H, sultone), 1.61-2.49(m, 26H, CH3 + sultone + adamantane)<br>¹⁹F-NMR(DMSO-d6, 376 MHz): δ(ppm) = −106.6 | Adamantyl-C(=O)-O-CH2CH2-O-C(=O)-CF2-SO3⁻ Na⁺ |
| B1-22 | ¹H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 4.40(t, 2H, CH2), 4.20(t, 2H, CH2), 3.83-3.89(m, 1H, sultone), 3.43(m, 1H, sultone), 1.53-2.49(m, 38H, CH3 + sultone + anion CH2 + adamantane)<br>¹⁹F-NMR(DMSO-d6, 376 MHz): δ(ppm) = −111.2 | Adamantyl-CH2-C(=O)-O-CH2CH2-O-C(=O)-CF2-SO3⁻ Na⁺ |
| B1-23 | ¹H-NMR(DMSO-d6, 400 MHz): δ(ppm) = 7.72-7.83(m, 10H, ArH), 7.59(s, 2H, ArH), 4.90(m, 1H, sultone), 4.62-4.68(m, 3H, CH2 + sultone), 4.55(t, 2H, CF2CH2), 3.83-3.89(m, 1H, sultone), 3.43(m, 1H, sultone), 1.64-2.49(m, 26H, CH3 + sultone + adamantane)<br>¹⁹F-NMR(DMSO-d6, 376 MHz): δ(ppm) = −111.2 | Adamantyl-C(=O)-O-CH2-CF2-SO3⁻ Na⁺ |
| B1-24 | ¹H-NMR(DMSO-d6, 400 MHz): δ(ppm) = 7.72-7.83(m, 10H, ArH), 7.59(s, 2H, ArH), 4.90(m, 1H, sultone), 4.78(m, 1H), anion sultone), 4.62-4.68(m, 4H, CH2 + sultone + anion sultone), 3.83-3.89(m, 2H, sultone + anion sultone), 3.43(m, 1H, sultone), 3.34(m, 1H, anion sultone), 1.73-2.49(m, 16H, CH3 + sultone + anion sultone)<br>¹⁹F-NMR(DMSO-d6, 376 MHz): δ(ppm) = −107.7 | Norbornane sultone-O-C(=O)-CF2-SO3⁻ Na⁺ |

TABLE 6-continued

| Compound | Product Cation | Product Anion |
|---|---|---|
| B1-21 | ↑ | 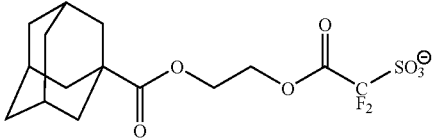 |
| B1-22 | ↑ | 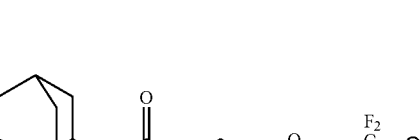 |
| B1-23 | ↑ | 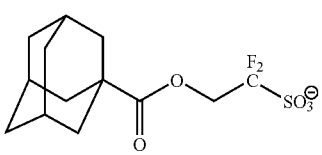 |
| B1-24 | ↑ | 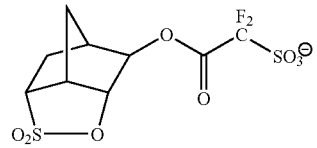 |

Example 25

Synthesis of Compound (B2-1)

15 g of the compound (2) and 150 g of dichloromethane were added to a three-necked flask in a nitrogen atmosphere, and cooled to 5° C. or lower. Then, 0.84 g of N,N-dimethylaminopyridine (DMAP) was added thereto, followed by stirring at 5° C. or lower for 5 minutes. Next, 7.2 g of ethyl-N,N-dimethylaminopropylcarbodiimide was added thereto. Thereafter, stirring was conducted for 10 minutes, and 4.3 g of a compound (4) was added thereto. Then, the temperature of the resultant was elevated to room temperature, and stirring was conducted at room temperature for 15 hours, followed by washing with a diluted hydrochloric acid and pure water. The resulting organic phase was dropwise added to 1,100 g of n-hexane and precipitated, thereby obtaining 10.1 g of a compound (B2-1).

The obtained compound (B2-1) was analyzed by NMR.

$^1$H-NMR (DMSO-d6, 400 MHz): δ(ppm)=7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH$_2$+oxo-norbornane), 2.69-2.73 (m, 1H, oxo-norbornane), 2.20-2.41 (m, 6H, CH$_3$), 2.06-2.16 (m, 2H, oxo-norbornane)

From the results shown above, it was confirmed that the compound (B2-1) had a structure shown below.

[Chemical Formula 84]

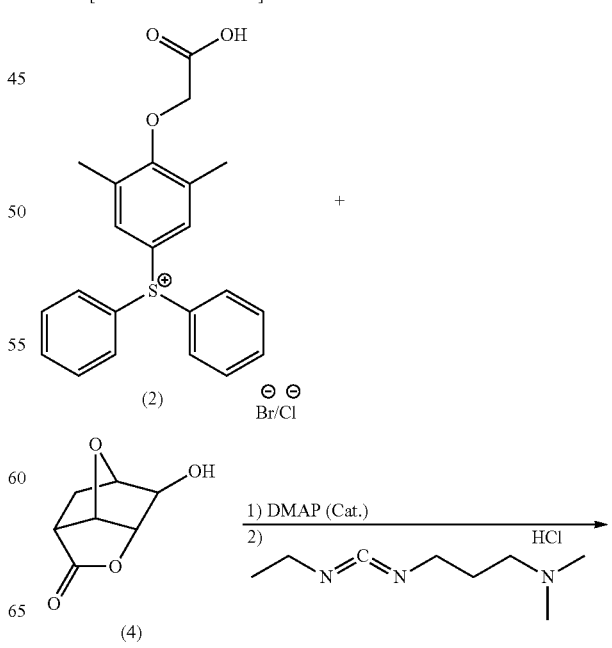

-continued

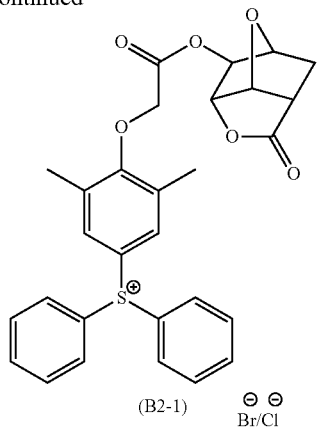

(B2-1)  ⊖⊖
        Br/Cl

Example 26

Synthesis of Compound (B2-2)

2.2 g of a compound (B2-1), 13.8 g of dichloromethane and 5.2 g of pure water were mixed together, and 1.7 g of potassium perfluorobutanesulfonate was added thereto, followed by stirring at room temperature for one night. Then, the organic phase was separated and washed with 5.2 g of pure water four times. Thereafter, dichloromethane was distilled off under reduced pressure, and the resultant was dried under reduced pressure, thereby obtaining 2.4 g of a compound (B2-2).

The obtained compound (B2-2) was analyzed by NMR.

$^{1}$H-NMR (DMSO-d6, 400 MHz): δ(ppm)=7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2+oxo-norbornane), 2.69-2.73 (m, 1H, oxo-norbornane), 2.20-2.41 (m, 6H, CH$_3$), 2.06-2.16 (m, 2H, oxo-norbornane)

$^{19}$F-NMR (DMSO-d6, 376 MHz): δ(ppm)=−77.8, −111.9, −118.5, −122.9

From the results shown above, it was confirmed that the compound (B2-2) had a structure shown below.

[Chemical Formula 85]

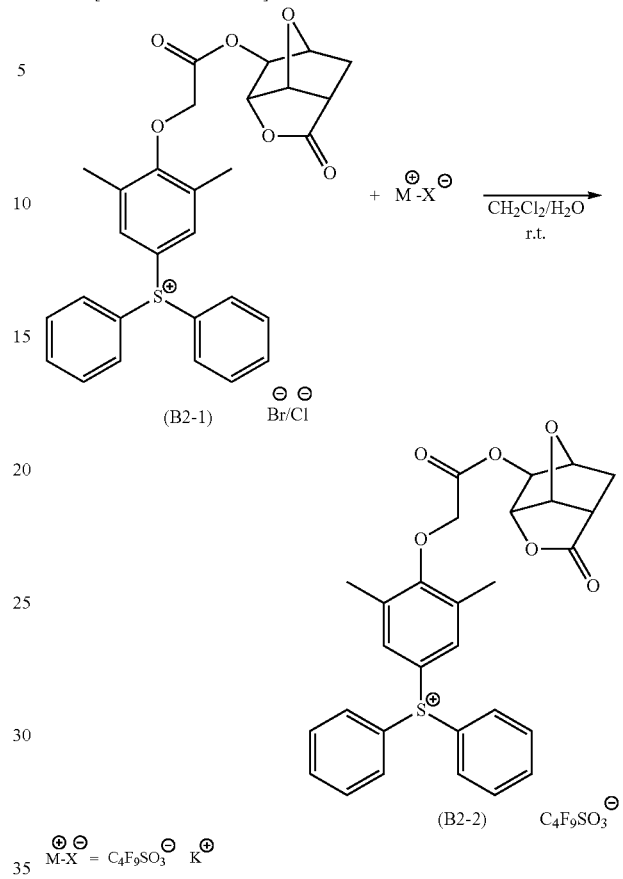

M-X = C$_4$F$_9$SO$_3$⊖ K⊕

Examples 27 to 48

The same procedure as in Example 26 was performed, except that the compound (M$^+$-X$^-$) was changed to a compound shown in Tables 7 to 14 (equimolar amount). In this manner, products having an anion and a cation as shown in Tables 7 to 14 (compounds (B2-3) to (B2-24)) were obtained.

Each of the obtained compounds was analyzed by NMR. The results are shown in Tables 7 to 14. In Tables 7 to 14, "↑" indicates that the cation of the product is the same as that of the compound (B2-3).

TABLE 7

| Compound | NMR | Compound M$^+$-X$^-$ | Product Cation | Product Anion |
|---|---|---|---|---|
| B2-3 | $^{1}$H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbonane), 2.69-2.73 (m, 1H, oxo-norbornane), 2.20-2.41 (m, 6H, CH3), 2.06-2.16 (m, 2H, oxo-norbornane) $^{19}$F-NMR DMSO-d6, 376 MHz): δ (ppm) = −75.0 | CF$_3$SO$_3$⊖ K⊕ | (structure shown) | CF$_3$SO$_3$⊖ |

TABLE 7-continued

| Compound | NMR | Compound M+-X− | Product Cation | Product Anion |
|---|---|---|---|---|
| B2-4 | $^1$H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbornane), 2.69-2.73 (m, 1H, oxo-norbornane), 2.20-2.41 (m, 6H, CH3), 2.06-2.16 (m, 2H, oxo-norbornane) $^{19}$F-NMR (DMSO-d6, 376 MHz): δ (ppm) = −77.3, −112.5, −121.7 | $C_3F_7SO_3^{\ominus}\;K^{\oplus}$ | ↑ | $C_3F_7SO_3^{\ominus}$ |

TABLE 8

| Compound | NMR | Compound M+-X− | Product Cation | Product Anion |
|---|---|---|---|---|
| B2-5 | $^1$H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbornane), 2.69-2.73 (m, 1H, oxo-norbornane), 2.20-2.41 (m, 6H, CH3), 2.06-2.16 (m, 2H, oxo-norbornane) $^{19}$F-NMR (DMSO-d6, 376 MHz): δ (ppm) = −116.9, −123.0 | 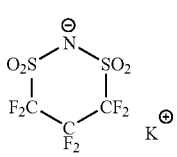 | ↑ | 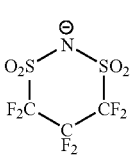 |
| B2-6 | $^1$H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbornane), 2.69-2.73 (m, 1H, oxo-norbornane), 2.20-2.41 (m, 6H, CH3), 2.06-2.16 (m, 2H, oxo-norbornane) $^{19}$F-NMR (DMSO-d6, 376 MHz): δ (ppm) = −75.9, −76.0, −114.7 | 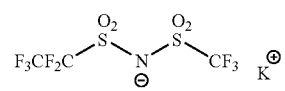 | ↑ | 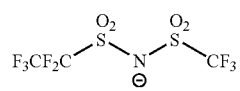 |

TABLE 9

| Compound | NMR | Compound M+-X− | Product Cation | Product Anion |
|---|---|---|---|---|
| B2-7 | $^1$H-NMR (DMSO-d6, 400 MHZ): δ (ppm) = 7.74-7.84 (m, 10H, ArH), 7.61 (s, 2H, ArH), 5.83-5.92 (m, 1H, anion CH), 5.42 (m, 2H, oxo-norbornane + anion CH), 5.21 (dd, 1H, anion, CH), 4.97 (s, 1H, oxo-norbornane), 4.67-4.71 (m, 4H, CH2 + oxo-norbornane), 4.45 (s, 2H, anion CH2), 2.69-2.73 (m, 1H, oxo-norbornane), 2.20-2.41 (m, 6H, CH3), 2.06-2.16 (m, 2H, oxo-norbornane) $^{19}$F-NMR (DMSO-d6, 376 MHz): δ (ppm) = −80.0, −113.0 | 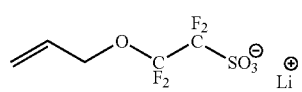 | ↑ | 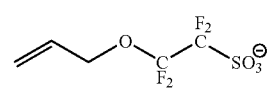 |

TABLE 9-continued

| | | Compound | Product | |
|---|---|---|---|---|
| Compound | NMR | M⁺-X⁻ | Cation | Anion |
| B2-8 | ¹H-NMR (DMSO-d6, 400 MHZ): δ (ppm) = 7.51-7.96 (m, 17H, ArH + Naph), 7.61 (s, 2H, ArH), 5.42 (t, 1H, oxo-norbornane), 5.20 (s, 2H, CH2), 4.97 (s, 1H, oxo-norbornane), 4.67-4.71 (m, 4H, CH2 + oxo-norbornane), 2.69-2.73 (m, 1H, oxo-norbornane), 2.20-2.41 (m, 6H, CH3), 2.06-2.16 (m, 2H, oxo-norbornane) ¹⁹F-NMR (DMSO-d6, 376 MHz): δ (ppm) = −80.5, −113.7 | naphthyl-CH2-O-CF2-CF2-SO3⁻ Li⁺ | ↑ | naphthyl-CH2-O-CF2-CF2-SO3⁻ |
| B2-9 | ¹H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbornane), 2.69-2.73 (m, 1H, oxo-norbornane), 2.20-2.41 (m, 6H, CH3), 2.06-2.16 (m, 5H, oxo-norbornane + adamantane), 1.96 (s, 6H, adamantane), 1.56 (s, 6H, adamantane) ¹⁹F-NMR (DMSO-d6, 376 MHz): δ (ppm) = −70.1, −113.4 | adamantyl-O-CF2-CF2-SO3⁻ Li⁺ | ↑ | adamantyl-O-CF2-CF2-SO3⁻ |

TABLE 10

| | | Compound | Product | |
|---|---|---|---|---|
| Compound | NMR | M⁺-X⁻ | Cation | Anion |
| B2-10 | ¹H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbornane), 2.69-2.73 (m, 1H, oxo-norbornane), 2.20-2.41 (m, 6H, CH3), 2.06-2.16 (m, 2H, oxo-norbornane) ¹⁹F-NMR (DMSO-d6, 376 MHz): δ (ppm) = −73.7 | C(SO2CF3)3⁻ H⁺ | ↑ | C(SO2CF3)3⁻ |
| B2-11 | ¹H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbornane), 2.69-2.73 (m, 1H, oxo-norbornane), 2.20-2.41 (m, 6H, CH3), 2.06-2.16 (m, 2H, oxo-norbornane) ¹⁹F-NMR (DMSO-d6, 376 MHz): δ (ppm) = −161.1, −149.7, −131.6, −76.2 | C6F5-C(SO2CF3)2⁻ H⁺ | ↑ | C6F5-C(SO2CF3)2⁻ |

TABLE 10-continued

| Compound | NMR | Compound M+-X− | Product Cation | Product Anion |
|---|---|---|---|---|
| B2-12 | $^1$H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbornane), 2.69-2.73 (m, 1H, oxo-norbornane), 2.20-2.41 (m, 6H, CH3), 2.06-2.16 (m, 2H, oxo-norbornano), 1.55-1.88 (m, 15H, adamantane) $^{19}$F-NMR (DMSO-d6, 376 MHz): δ (ppm) = −74.5 | 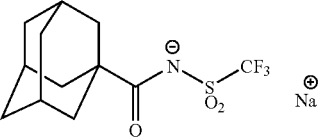 | ↑ | 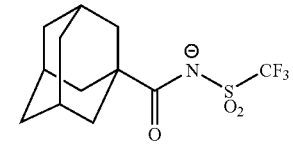 |

TABLE 11

| Compound | NMR | Compound M+-X− | Product Cation | Product Anion |
|---|---|---|---|---|
| B2-13 | $^1$H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbornane), 4.19 (s, 2H, CH2), 2.69-2.73 (m, 1H, oxo-norbornane), 2.20-2.41 (m, 6H, CH3), 2.06-2.16 (m, 2H, oxo-norbornane), 1.55-1.87 (m, 15H, adamantane) $^{19}$F-NMR (DMSO-d6, 376 MHz): δ (ppm) = −77.7 | 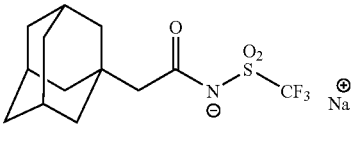 | ↑ | 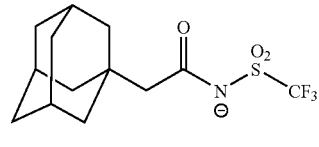 |
| B2-14 | $^1$H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbornane), 2.69-2.81 (m, 2H, oxo-norbornane + cyclohexyl), 2.20-2.41 (m, 6H, CH3), 2.04-2.16 (m, 4H, oxo-norbornane + cyclohexyl), 1.73-1.75 (m, 2H, cyclohexyl), 1.56-1.59 (m, 1H, cyclohexyl), 1.07-1.33 (m, 5H, cyclohexyl) $^{19}$F-NMR (DMSO-d6, 376 MHz): δ (ppm) = −74.7 | 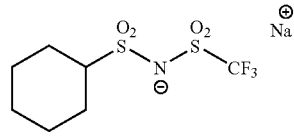 | ↑ | 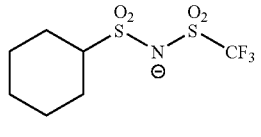 |

TABLE 11-continued

| Compound | | Compound | Product | |
|---|---|---|---|---|
| | NMR | M⁺-X⁻ | Cation | Anion |
| B2-15 | ¹H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbornane), 2.69-2.73 (m, 1H, oxo-norbornane), 2.20-2.41 (m, 6H, CH3), 2.06-2.16 (m, 5H, oxo-norbornane + adamantane), 1.99 (m, 6H, adamantane), 1.59 (s, 6H, adamantane) ¹⁹F-NMR (DMSO-d6, 376 MHz): δ (ppm) = −69.2, −76.0, −112.9 | 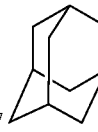 | ↑ | 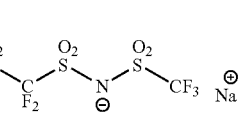 |

TABLE 12

| Compound | | Compound | Product | |
|---|---|---|---|---|
| | NMR | M⁺-X⁻ | Cation | Anion |
| B2-16 | ¹H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbornane), 2.88 (d, 1H, anion CH), 2.66-2.73 (m, 2H, oxo-norbornane + anion CH), 2.37 (d, 1H, CH), 2.17-2.41 (m, 9H, CH3 + oxo-norbornane + anion CH), 1.90 (t, 1H, anion CH), 1.74-1.89 (m, 2H, anion CH2), 1.22-1.29 (m, 2H, anion CH2), 1.03 (s, 3H, anion CH3), 0.71 (s, 3H, anion CH3) | 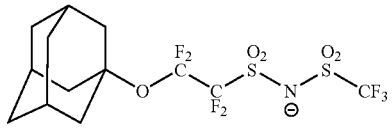 | ↑ | 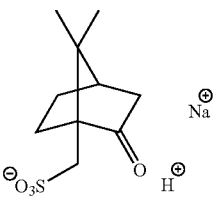 |

TABLE 12-continued

| Compound | NMR | Compound M+-X− | Product Cation | Product Anion |
|---|---|---|---|---|
| B2-17 | ¹H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbornane), 4.40-4.50 (m, 4H, anion CH2), 2.69-2.73 (m, 1H, oxo-norbornane), 2.20-2.41 (m, 6H, CH3), 2.06-2.16 (m, 2H, oxo-norbornane) ¹⁹F-NMR (DMSO-d6, 376 MHz): δ (ppm) = −106.7, −154.0, −160.0, −161.5 | 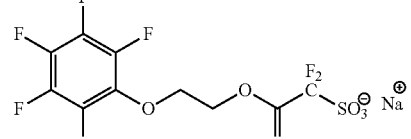 | ↑ | 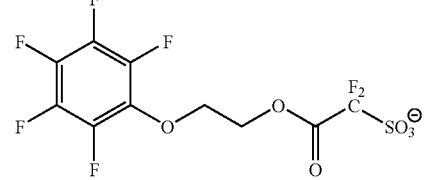 |
| B2-18 | ¹H-NMR (DMSO-d6, 400 MHZ): δ (ppm) = 8.74-8.82 (m, 2H, Py-H), 7.74-7.84 (m, 12H, ArH + Py-H), 7.61 (s, 2H, ArH), 5.42 (t, 1H, oxo-norbornane), 4.97 (s, 1H, oxo-norbornane), 4.54-4.71 (m, 8H, CH2 + oxo-norbornane + anion CH2CH2), 2.69-2.73 (m, 1H, oxo-norbornane), 2.20-2.41 (m, 6H, CH3), 2.06-2.16 (m, 2H, oxo-norbornane) ¹⁹F-NMR (DMSO-d6, 376 MHz): δ (ppm) = −106.5 | 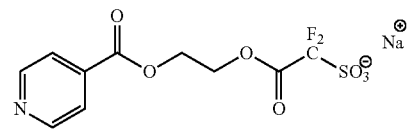 | ↑ | 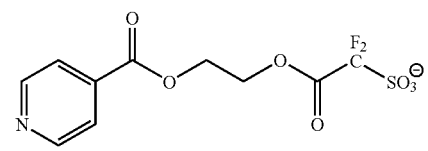 |

TABLE 13

| Compound | | Product | |
|---|---|---|---|
| Compound | NMR | M⁺-X⁻ (Cation / Anion) | |
| B2-19 | ¹H-NMR (DMSO-d6, 400 MHZ): δ (ppm) = 7.74-7.84 (m, 10H, ArH), 7.61 (s, 2H, ArH), 5.45 (m, 2H, oxo-norbornane + anion oxo-norbornane), 4.97 (m, 2H, oxo-norbornane + anion oxo-norbornane), 4.67-4.71 (m, 2H, CH2 + oxo-norbornane + anion oxo-norbornane), 4.57 (d, 1H, anion oxo-norbornane), 2.69-2.73 (m, 2H, oxo-norbornane + anion oxo-norbornane), 2.20-2.41 (m, 6H, CH3), 2.06-2.16 (m, 4H, oxo-norbornane + anion oxo-norbornane) ¹⁹F-NMR (DMSO-d6, 376 MHz): δ (ppm) = −107.1 | [structure: oxo-norbornane-OC(O)CF₂SO₃⁻ Na⁺] | [structure: oxo-norbornane-OC(O)CF₂SO₃⁻] |
| B2-20 | ¹H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbornane), 4.41 (t, 2H, anion CH2), 4.23 (t, 2H, anion CH2), 0.79-2.89 (m, 30H, oxo-norbornane + CH3 + undeoanoyl) ¹⁹F-NMR (DMSO-d6, 376 MHz): δ (ppm) = −106.8 | [structure: long alkyl chain-C(O)O-CH₂CH₂-OC(O)CF₂SO₃⁻ Na⁺] | [structure: long alkyl chain-C(O)O-CH₂CH₂-OC(O)CF₂SO₃⁻] |

TABLE 13-continued

| Compound | | Product | |
|---|---|---|---|
| Compound | NMR | M⁺-X⁻ | Cation | Anion |
| B2-21 | ¹H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbornane), 4.40 (t, 2H, CH2), 4.21 (t, 2H, CH2), 2.69-2.73 (m, 1H, oxo-norbornane), 2.20-2.41 (m, 6H, CH3), 2.06-2.16 (m, 2H, oxo-norbornane), 1.61-1.98 (m, 15H, adamantane) ¹⁹F-NMR (DMSO-d6, 376 MHz): δ (ppm) = −106.6 | [adamantane-C(O)O-CH₂CH₂-O-C(O)-CF₂-SO₃⁻ Na⁺] | ↑ | [adamantane-C(O)O-CH₂CH₂-O-C(O)-CF₂-SO₃⁻] |

TABLE 14

| Compound NMR | Compound M+-X- | Product Cation | Product Anion |
|---|---|---|---|
| B2-22 ¹H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbornane), 4.40 (t, 2H, CH2), 4.20 (t, 2H, CH2), 2.69-2.73 (m, 1H, oxo-norbornane), 2.20-2.41 (m, 6H, CH3), 2.06-2.16 (m, 4H, oxo-norbornane + anion CH2), 1.53-1.95 (m, 15H, adamantane) ¹⁹F-NMR (DMSO-d6, 376 MHz): δ (ppm) = -111.2 | 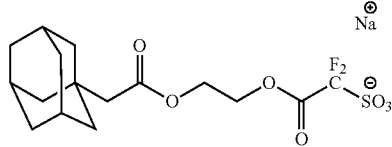 | ↑ | 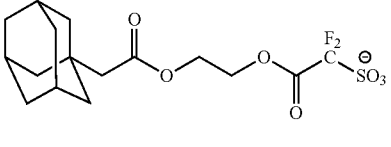 |
| B2-23 ¹H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.67-4.71 (m, 4H, CH2 + oxo-norbornane), 4.55 (t, 2H, CF2CH2), 2.69-2.73 (m, 1H, oxo-norbornane), 2.20-2.41 (m, 6H, CH3), 2.06-2.16 (m, 2H, oxo-norbornane), 1.94 (m, 3H, adamantane), 1.82 (m, 6H, adamantane), 1.64 (m, 6H, adamantane) ¹⁹F-NMR (DMSO-d6, 376 MHz): δ (ppm) = -111.2 | 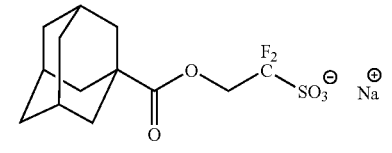 | ↑ | 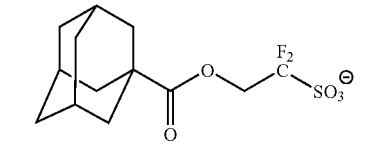 |
| B2-24 ¹H-NMR (DMSO-d6, 400 MHZ): δ (ppm) = 7.74-7.84 (m, 10H, ArH), 7.61 (s, 2H, ArH), 5.42 (t, 1H, oxo-norbornane), 4.97 (s, 1H, oxo-norbornane), 4.78 (m, 1H, sultone), 4.67-4.71 (m, 5H, CH2 + oxo-norbornane + sultone), 3.88 (t, 1H, sultone), 3.34 (m, 1H, sultone), 2.69-2.73 (m, 1H, oxo-norbornane), 2.47-2.49 (m, 1H, sultone), 1.73-2.20 (m, 12H, CH3 + oxo-norbornane + sultone) ¹⁹F-NMR (DMSO-d6, 376 MHz): δ (ppm) = -107.7 | 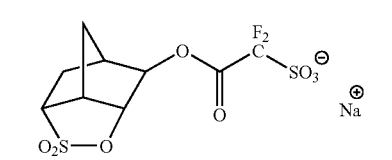 | ↑ | 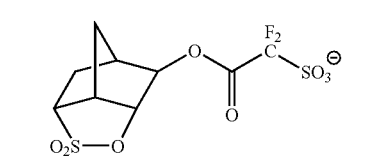 |

Example 49

Synthesis of Compound (B3-1)

13.2 g of the compound (2) and 132 g of dichloromethane were added to a three-necked flask in a nitrogen atmosphere, and cooled to 5° C. or lower. Then, 0.73 g of N,N-dimethylaminopyridine (DMAP) was added thereto, followed by stirring at 5° C. or lower for 5 minutes. Next, 14.4 g of ethyl-N, N-dimethylaminopropylcarbodiimide was added thereto. Thereafter, stirring was conducted for 10 minutes, and 30 g of a dichloromethane solution containing 15 g of 5-hydroxy-2- adamantanone was gradually added thereto in a dropwise manner. Then, the temperature of the resultant was elevated to room temperature, and stirring was conducted at room temperature for 31 hours, followed by washing with a diluted hydrochloric acid and pure water. The resulting organic phase was dropwise added to 1,000 g of n-hexane and precipitated, thereby obtaining 12.3 g of a compound (B3-1).

The obtained compound (B3-1) was analyzed by NMR.
$^1$H-NMR (DMSO-d6,400 MHz): δ(ppm)=7.72-7.84 (m, 10H, ArH), 7.59 (s, 2H, ArH), 4.56 (s, 2H, CH$_2$), 2.49 (m, 2H, Ad), 2.27-2.34 (m, 13H, CH$_3$+Ad), 1.94-1.97 (m, 2H, Ad), 1.72-1.79 (m, 2H, Ad).

From the results shown above, it was confirmed that the compound (B3-1) had a structure shown below.

organic phase was separated and washed with 56.9 g of pure water four times. Thereafter, dichloromethane was distilled off under reduced pressure, and the resultant was dried under reduced pressure, thereby obtaining 2.4 g of a compound (B3-2).

The obtained compound (B3-2) was analyzed by NMR.
$^1$H-NMR (DMSO-d6,400 MHz): δ(ppm)=7.72-7.84 (m, 10H, ArH), 7.59 (s, 2H, ArH), 4.56 (s, 2H, CH$_2$), 2.49 (m, 2H, Ad), 2.27-2.34 (m, 13H, CH$_3$+Ad), 1.94-1.97 (m, 2H, Ad), 1.72-1.79 (m, 2H, Ad).
$^{19}$F-NMR (DMSO-d6,376 MHz): δ(ppm)=−77.3, −111.5, −118.1, −122.4.

From the results shown above, it was confirmed that the compound (B3-2) had a structure shown below.

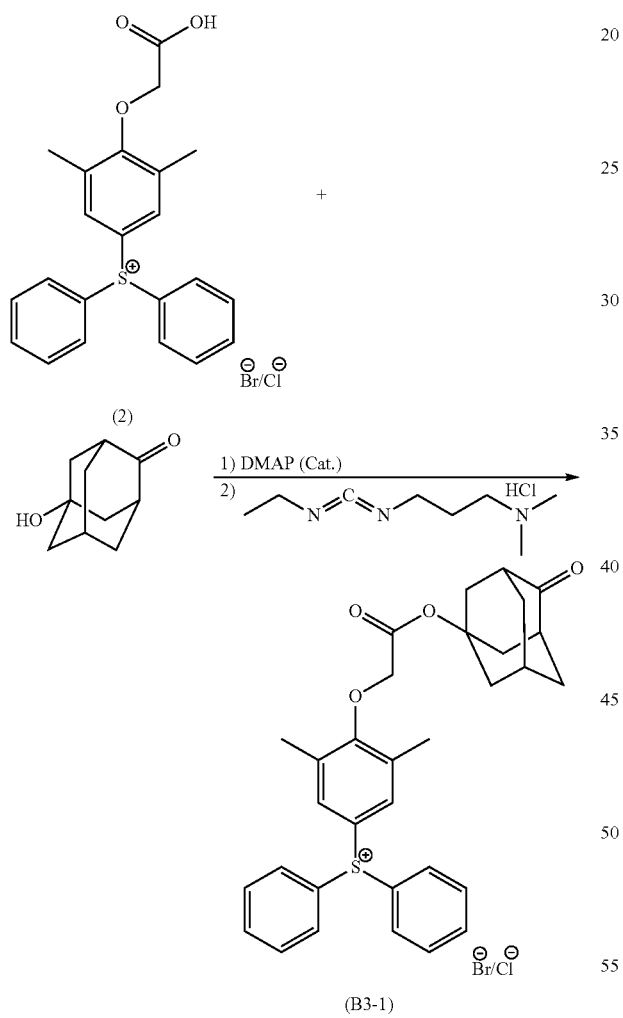

[Chemical Formula 86]

[Chemical Formula 87]

Example 50

Synthesis of Compound (B3-2)

4.1 g of a compound (B3-1), 57 g of dichloromethane and 56.9 g of pure water were mixed together, and 2.8 g of potassium perfluorobutanesulfonate was added thereto, followed by stirring at room temperature for one night. Then, the

Examples 51 to 72

The same procedure as in Example 50 was performed, except that the compound (M$^+$-X$^−$) was changed to a compound shown in Tables 15 to 20 (equimolar amount). In this manner, products having an anion and a cation as shown in Tables 15 to 20 (compounds (B3-3) to (B3-24)) were obtained.

Each of the obtained compounds were analyzed by NMR. The results are shown in Tables 15 to 20. In Tables 15 to 20, "↑" indicates that the cation of the product is the same as that of the compound (B3-3).

TABLE 15

| Compound | NMR | Compound M⁺-X⁻ | Product Cation | Product Anion |
|---|---|---|---|---|
| B3-3 | ¹H-NMR (DMSO-d6, 400 MHZ): δ (ppm) = 7.72-7.84 (m, 10H, ArH), 7.59 (s, 2H, ArH), 4.56 (s, 2H, CH2), 2.49 (m, 2H, Ad), 2.27-2.34 (m, 13H, CH3 + Ad), 1.94-1.97 (m, 2H, Ad), 1.72-1.79 (m, 2H, Ad). ¹⁹F-NMR (DMSO-d6, 376 MHz): δ (ppm) = −75.0 | $CF_3SO_3^{\ominus} \; K^{\oplus}$ | 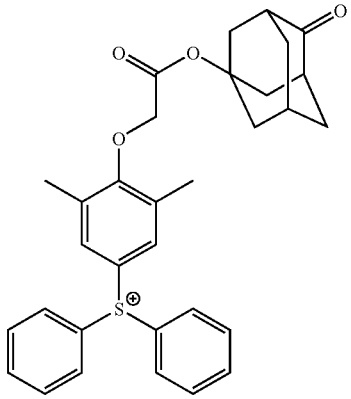 | $CF_3SO_3^{\ominus}$ |
| B3-4 | ¹H-NMR (DMSO-d6, 400 MHZ): δ (ppm) = 7.72-7.84 (m, 10H, ArH), 7.59 (s, 2H, ArH), 4.56 (s, 2H, CH2), 2.49 (m, 2H, Ad), 2.27-2.34 (m, 13H, CH3 + Ad), 1.94-1.97 (m, 2H, Ad), 1.72-1.79 (m, 2H, Ad). ¹⁹F-NMR (DMSO-d6, 376 MHz): δ (ppm) = −77.3, −112.5, −121.7 | $C_3F_7SO_3^{\ominus} \; K^{\oplus}$ | ↑ | $C_3F_7SO_3^{\ominus}$ |
| B3-5 | ¹H-NMR (DMSO-d6, 400 MHZ): δ (ppm) = 7.72-7.84 (m, 10H, ArH), 7.59 (s, 2H, ArH), 4.56 (s, 2H, CH2), 2.49 (m, 2H, Ad), 2.27-2.34 (m, 13H, CH3 + Ad), 1.94-1.97 (m, 2H, Ad), 1.72-1.79 (m, 2H, Ad). ¹⁹F-NMR (DMSO-d6, 376 MHz): δ (ppm) = −116.9, −123.0 | 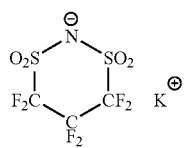 | ↑ | 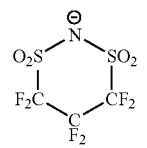 |
| B3-6 | ¹H-NMR (DMSO-d6, 400 MHZ): δ (ppm) = 7.72-7.84 (m, 10H, ArH), 7.59 (s, 2H, ArH), 4.56 (s, 2H, CH2), 2.49 (m, 2H, Ad), 2.27-2.34 (m, 13H, CH3 + Ad), 1.94-1.97 (m, 2H, Ad), 1.72-1.79 (m, 2H, Ad). ¹⁹F-NMR (DMSO-d6, 376 MHz): δ (ppm) = −75.9, −76.0, −114.7 | 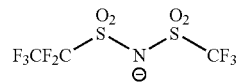 | ↑ | $F_3CF_2C-\underset{O_2}{S}-\underset{\ominus}{N}-\underset{O_2}{S}-CF_3$ |

TABLE 16

| Compound | NMR | Compound M+-X− | Product Cation | Product Anion |
|---|---|---|---|---|
| B3-7 | ¹H-NMR (DMSO-d6, 400 MHZ): δ (ppm) = 7.72-7.84 (m, 10H, ArH), 7.59 (s, 2H, ArH), 5.83-5.92 (m, 1H, anion CH), 5.41 (dd, 1H, anion CH), 5.21 (dd, 1H, anion CH), 4.56 (s, 2H, CH2), 4.45 (s, 2H, anion CH2), 2.49 (m, 2H, Ad), 2.27-2.34 (m, 13H, CH3 + Ad), 1.94-1.97 (m, 2H, Ad), 1.72-1.79 (m, 2H, Ad). ¹⁹F-NMR (DMSO-d6, 376 MHz): δ (ppm) = −80.0, −113.0 | allyl-O-CF2-C(F2)-SO3⁻ Li⁺ | ↑ | allyl-O-CF2-C(F2)-SO3⁻ |
| B3-8 | ¹H-NMR (DMSO-d6, 400 MHZ): δ (ppm) = 7.51-7.96 (m, 17H, ArH + Naph), 7.59 (s, 2H, ArH), 5.20 (s, 2H, CH2), 4.56 (s, 2H, CH2), 2.49 (m, 2H, Ad), 2.27-2.34 (m, 13H, CH3 + Ad), 1.94-1.97 (m, 2H, Ad), 1.72-1.79 (m, 2H, Ad). ¹⁹F-NMR (DMSO-d6, 376 MHz): δ (ppm) = −80.5, −113.7 | naphthyl-CH2-O-CF2-CF2-SO3⁻ Li⁺ | ↑ | naphthyl-CH2-O-CF2-CF2-SO3⁻ |
| B3-9 | ¹H-NMR (DMSO-d6, 400 MHZ): δ (ppm) = 7.72-7.84 (m, 10H, ArH), 7.59 (s, 2H, ArH), 4.56 (s, 2H, CH2), 2.49 (m, 2H, Ad), 2.27-2.34 (m, 13H, CH3 + Ad), 2.09 (s, 3H, adamantane), 1.94-1.97 (m, 8H, Ad), 1.72-1.79 (m, 2H, Ad), 1.56 (s, 6H, adamantane). ¹⁹F-NMR (DMSO-d6, 376 MHz): δ (ppm) = −70.1, −113.4 | adamantyl-O-CF2-CF2-SO3⁻ Li⁺ | ↑ | adamantyl-O-CF2-CF2-SO3⁻ |

TABLE 17

| Compound | NMR | Compound M+-X− |
|---|---|---|
| B3-10 | ¹H-NMR(DMSO-d6, 400 MHz): δ (ppm) = 7.72-7.84 (m, 10H, ArH), 7.59 (s, 2H, ArH), 4.56 (s, 2H, CH2), 2.49 (m, 2H, Ad), 2.27-2.34 (m, 13H, CH3 + Ad), 1.94-1.97 (m, 2H, Ad), 1.72-1.79 (m, 2H, Ad). ¹⁹F-NMR(DMSO-d6, 376 MHz): δ (ppm) = −73.7 | C(SO2CF3)3⁻ H⁺ |
| B3-11 | ¹H-NMR(DMSO-d6, 400 MHz): δ (ppm) = 7.72-7.84 (m, 10H, ArH), 7.59 (s, 2H, ArH), 4.56 (s, 2H, CH2), 2.49 (m, 2H, Ad), 2.27-2.34 (m, 13H, CH3 + Ad), 1.94-1.97 (m, 2H, Ad), 1.72-1.79 (m, 2H, Ad). ¹⁹F-NMR(DMSO-d6, 376 MHz): δ (ppm) = −161.1, −149.7, −131.6, −76.2 | pentafluorophenyl-C(SO2CF3)2⁻ H⁺ |

TABLE 17-continued

| | | |
|---|---|---|
| B3-12 | ¹H-NMR(DMSO-d6, 400 MHz): δ (ppm) = 7.72-7.84 (m, 10H, ArH), 7.59 (s, 2H, ArH), 4.56 (s, 2H, CH2), 2.49 (m, 2H, Ad), 2.27-2.34 (m, 13H, CH3 + Ad), 1.94-1.97 (m, 2H, Ad), 1.72-1.79 (m, 2H, Ad), 1.55-1.88 (m, 15H, Ad).<br>¹⁹F-NMR(DMSO-d6, 376 MHz): δ (ppm) = −74.5 | 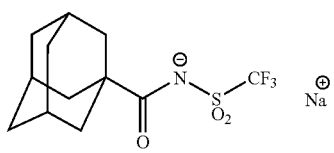 |

| | | Product | |
|---|---|---|---|
| Compound | Cation | | Anion |
| B3-10 | ↑ | | F₃CO₂S⁻C⁻(SO₂CF₃)(SO₂CF₃) |
| B3-11 | ↑ | | pentafluorophenyl-C⁻(SO₂CF₃)(SO₂CF₃) (F₃CO₂S, SO₂CF₃ substituents) |
| B3-12 | ↑ | | Adamantyl-C(O)-N⁻-SO₂CF₃ |

TABLE 18

| Compound | NMR | Compound M⁺-X⁻ |
|---|---|---|
| B3-13 | ¹H-NMR(DMSO-d6, 400 MHz): δ (ppm) = 7.72-7.84 (m, 10H, ArH), 7.59 (s, 2H, ArH), 4.56 (s, 2H, CH2), 4.19 (s, 2H, CH2), 2.49 (m, 2H, Ad), 2.27-2.34 (m, 13H, CH3 + Ad), 1.94-1.97 (m, 2H, Ad), 1.55-1.87 (m, 17H, Ad).<br>¹⁹F-NMR(DMSO-d6, 376 MHz): δ (ppm) = −77.7 | Adamantyl-CH₂-C(O)-N⁻-SO₂CF₃  Na⁺ |
| B3-14 | ¹H-NMR(DMSO-d6, 400 MHz): δ (ppm) = 7.72-7.84 (m, 10H, ArH), 7.59 (s, 2H, ArH), 4.56 (s, 2H, CH2), 2.77-2.81 (m, 1H, Cyclohexyl), 2.49 (m, 2H, Ad), 2.27-2.34 (m, 13H, CH3 + Ad), 2.04-2.08 (m, 2H, Cyclohexyl), 1.94-1.97 (m, 2H, Ad), 1.72-1.79 (m, 2H, Ad + Cyclohexyl), 1.56-1.59 (m, 1H, Cyclohexyl), 1.07-1.33 (m, 5H, Cyclohexyl).<br>¹⁹F-NMR(DMSO-d6, 376 MHz): δ (ppm) = −74.7 | Cyclohexyl-SO₂-N⁻-SO₂CF₃  Na⁺ |
| B3-15 | ¹H-NMR(DMSO-d6, 400 MHz): δ (ppm) = 7.72-7.84 (m, 10H, ArH), 7.59 (s, 2H, ArH), 4.56 (s, 2H, CH2), 2.49 (m, 2H, Ad), 2.27-2.34 (m, 13H, CH3 + Ad), 2.13 (m, 3H, adamantane), 1.94-1.99 (m, 8H, Ad), 1.72-1.79 (m, 2H, Ad), 1.59 (s, 6H, adamantane).<br>¹⁹F-NMR(DMSO-d6, 376 MHz): δ (ppm) = −69.2, −76.0, −112.9. | Adamantyl-O-CF₂-CF₂-SO₂-N⁻-SO₂CF₃  Na⁺ |
| B3-16 | ¹H-NMR(DMSO-d6, 400 MHz): δ (ppm) = 7.72-7.84 (m, 10H, ArH), 7.59 (s, 2H, ArH), 4.56 (s, 2H, CH2), 2.88 (d, 1H, CH), 2.66-2.74 (m, 1H, CH), 2.49 (m, 2H, Ad), 2.27-2.37 (m, 14H, CH3 + Ad + CH), 2.17-2.24 (m, 1H, CH), 1.94-1.97 (m, 2H, Ad), 1.90 (t, 1H, CH), 1.72-1.89 (m, 4H, Ad + CH2), 1.22-1.29 (m, 2H, CH2), 1.03 (s, 3H, CH3), 0.71 (s, 3H, CH3). | camphorsulfonate (⁻O₃S-CH₂-camphor)  Na⁺ H⁺ |

TABLE 18-continued

| Compound | Product Cation | Anion |
|---|---|---|
| B3-13 | ↑ | adamantyl-CH2-C(=O)-N(−)-S(O2)-CF3 |
| B3-14 | ↑ | cyclohexyl-S(O2)-N(−)-S(O2)-CF3 |
| B3-15 | ↑ | adamantyl-O-CF2-CF2-S(O2)-N(−)-S(O2)-CF3 |
| B3-16 | ↑ | camphorsulfonate (−O3S-CH2-[camphor]) |

TABLE 19

| Compound | NMR | Compound M+-X− |
|---|---|---|
| B3-17 | ¹H-NMR(DMSO-d6, 400 MHz): δ (ppm) = 7.72-7.84 (m, 10H, ArH), 7.59 (s, 2H, ArH), 4.56 (s, 2H, CH2), 4.40-4.50 (m, 4H, CH2), 2.49 (m, 2H, Ad), 2.27-2.34 (m, 13H, CH3 + Ad), 1.94-1.97 (m, 2H, Ad), 1.72-1.79 (m, 2H, Ad). ¹⁹F-NMR(DMSO-d6, 376 MHz): δ (ppm) = −106.7, −154.0, −160.0, −161.5 | pentafluorophenyl-O-CH2CH2-O-C(=O)-CF2-SO3− Na+ |
| B3-18 | ¹H-NMR(DMSO-d6, 400 MHz): δ (ppm) = 8.74-8.82 (m, 2H, Py-H), 7.72-7.84 (m, 12H, ArH + Py-H), 7.59 (s, 2H, ArH), 4.54-4.61 (m, 6H, CH2), 2.49 (m, 2H, Ad), 2.27-2.34 (m, 13H, CH3 + Ad), 1.94-1.97 (m, 2H, Ad), 1.72-1.79 (m, 2H, Ad). ¹⁹F-NMR(DMSO-d6, 376 MHz): δ (ppm) = −106.5 | isonicotinoyl-O-CH2CH2-O-C(=O)-CF2-SO3− Na+ |
| B3-19 | ¹H-NMR(DMSO-d6, 400 MHz): δ (ppm) = 7.72-7.84 (m, 10H, ArH), 7.59 (s, 2H, ArH), 5.46 (t, 1H, oxo-norbornane), 4.97 (s, 1H, oxo-norbornane), 4.71 (d, 1H, oxo-norbornane), 4.57 (d, 1H, oxo-norbornane), 4.56 (s, 2H, CH2), 2.69-2.73 (m, 1H, oxo-norbornane), 2.49 (m, 2H, Ad), 2.27-2.34 (m, 13H, CH3 + Ad), 2.06-2.16 (m, 2H, oxo-norbornane), 1.94-1.97 (m, 2H, Ad), 1.72-1.79 (m, 2H, Ad). ¹⁹F-NMR(DMSO-d6, 376 MHz): δ (ppm) = −107.1 | oxo-norbornanyl-O-C(=O)-CF2-SO3− Na+ |
| B3-20 | ¹H-NMR(DMSO-d6, 400 MHz): δ (ppm) = 7.72-7.84 (m, 10H, ArH), 7.59 (s, 2H, ArH), 4.56 (s, 2H, CH2), 4.41 (t, 2H, CH2), 4.23 (t, 2H, CH2), 2.49 (m, 2H, Ad), 2.27-2.34 (m, 13H, CH3 + Ad), 1.94-1.97 (m, 2H, Ad), 1.72-1.79 (m, 2H, Ad), 0.79-2.89 (m, 21H, Undecanoyl). ¹⁹F-NMR(DMSO-d6, 376 MHz): δ (ppm) = −106.8 | undecanoyl-O-CH2CH2-O-C(=O)-CF2-SO3− Na+ |

TABLE 19-continued

| Compound | Product Cation | Anion |
|---|---|---|
| B3-17 | ↑ | pentafluorophenyl-O-CH₂CH₂-O-C(=O)-CF₂-SO₃⁻ |
| B3-18 | ↑ | isonicotinoyl-O-CH₂CH₂-O-C(=O)-CF₂-SO₃⁻ |
| B3-19 | ↑ | norbornane lactone-O-C(=O)-CF₂-SO₃⁻ |
| B3-20 | ↑ | CH₃(CH₂)₉C(=O)-O-CH₂CH₂-O-C(=O)-CF₂-SO₃⁻ |

TABLE 20

| Compound | NMR | Compound M⁺-X⁻ |
|---|---|---|
| B3-21 | ¹H-NMR(DMSO-d6, 400 MHz): δ (ppm) = 7.72-7.84 (m, 10H, ArH), 7.59 (s, 2H, ArH), 4.56 (s, 2H, CH2), 4.40 (t, 2H, CH2), 4.21 (t, 2H, CH2), 2.49 (m, 2H, Ad), 2.27-2.34 (m, 13H, CH3 + Ad), 1.94-1.97 (m, 2H, Ad), 1.61-198 (m, 17H, Ad).<br>¹⁹F-NMR(DMSO-d6, 376 MHz): δ (ppm) = −106.6 | 1-adamantyl-C(=O)-O-CH₂CH₂-O-C(=O)-CF₂-SO₃⁻ Na⁺ |
| B3-22 | ¹H-NMR(DMSO-d6, 400 MHz): δ (ppm) = 7.72-7.84 (m, 10H, ArH), 7.59 (s, 2H, ArH), 4.56 (s, 2H, CH2), 4.40 (t, 2H, CH2), 4.20 (t, 2H, CH2), 2.49 (m, 2H, Ad), 2.27-2.34 (m, 13H, CH3 + Ad), 2.05 (s, 2H, CH2), 1.94-1.97 (m, 2H, Ad), 1.53-1.92 (m, 17H, Ad).<br>¹⁹F-NMR(DMSO-d6, 376 MHz): δ (ppm) = −111.2 | 1-adamantyl-CH₂-C(=O)-O-CH₂CH₂-O-C(=O)-CF₂-SO₃⁻ Na⁺ |
| B3-23 | ¹H-NMR(DMSO-d6, 400 MHz): δ (ppm) = 7.72-7.84 (m, 10H, ArH), 7.59 (s, 2H, ArH), 4.56 (m, 4H, CH2 + CF2CH2), 2.49 (m, 2H, Ad), 2.27-2.34 (m, 13H, CH3 + Ad), 1.94-1.97 (m, 5H, Ad), 1.82 (m, 6H, Ad), 1.72-1.79 (m, 2H, Ad), 1.64 (m, 6H, Ad).<br>¹⁹F-NMR(DMSO-d6, 376 MHz): δ (ppm) = −111.2 | 1-adamantyl-C(=O)-O-CH₂-CF₂-SO₃⁻ Na⁺ |
| B3-24 | ¹H-NMR(DMSO-d6, 400 MHz): δ (ppm) = 7.72-7.84 (m, 10H, ArH), 7.59 (s, 2H, ArH), 4.78 (m, 1H, CH), 4.66 (t, 1H, CH), 4.56 (s, 2H, CH2), 3.88 (t, 1H, CH), 3.34 (m, 1H, CH), 1.72-2.49 (m, 24H, Ad + sultone + CH3).<br>¹⁹F-NMR(DMSO-d6, 376 MHz): δ (ppm) = −107.7 | norbornane sultone-O-C(=O)-CF₂-SO₃⁻ Na⁺ |

TABLE 20-continued

| Compound | Product Cation | Anion |
|---|---|---|
| B3-21 | ↑ | (adamantane-C(O)O-CH₂CH₂-O-C(O)-CF₂-SO₃⁻) |
| B3-22 | ↑ | (adamantane-CH₂-C(O)O-CH₂CH₂-O-C(O)-CF₂-SO₃⁻) |
| B3-23 | ↑ | (adamantane-C(O)O-CH₂-CF₂-SO₃⁻) |
| B3-24 | ↑ | (norbornane sultone-O-C(O)-CF₂-SO₃⁻) |

Example 73

Synthesis of Compound (B4-1)

10 g of the compound (2) and 100 g of dichloromethane were added to a three-necked flask in a nitrogen atmosphere, and cooled to 5° C. or lower. Then, 0.56 g of N,N-dimethylaminopyridine (DMAP) was added thereto, followed by stirring at 5° C. or lower for 5 minutes. Next, 4.8 g of ethyl-N,N-dimethylaminopropylcarbodiimide was added thereto. Thereafter, stirring was conducted for 10 minutes, and 2.81 g of a compound (5) was added thereto. Then, the temperature of the resultant was elevated to room temperature, and stirring was conducted at room temperature for 15 hours, followed by washing with a diluted hydrochloric acid and pure water. The resulting organic phase was dropwise added to 1,000 g of n-hexane and precipitated, thereby obtaining 10.5 g of a compound (B4-1).

The obtained compound (B4-1) was analyzed by NMR.

$^1$H-NMR (DMSO-d6, 400 MHz): δ(ppm)=7.74-7.84 (m, 10H, ArH), 7.61 (s, 2H, ArH), 4.49-4.62 (m, 2H, norbornane), 3.24 (m, 1H, norbornane), 2.44-2.54 (m, 2H, norbornane), 1.91-2.06 (m, 2H, norbornane), 1.57-1.67 (m, 2H, norbornane)

From the results shown above, it was confirmed that the compound (B4-1) had a structure shown below.

[Chemical Formula 88]

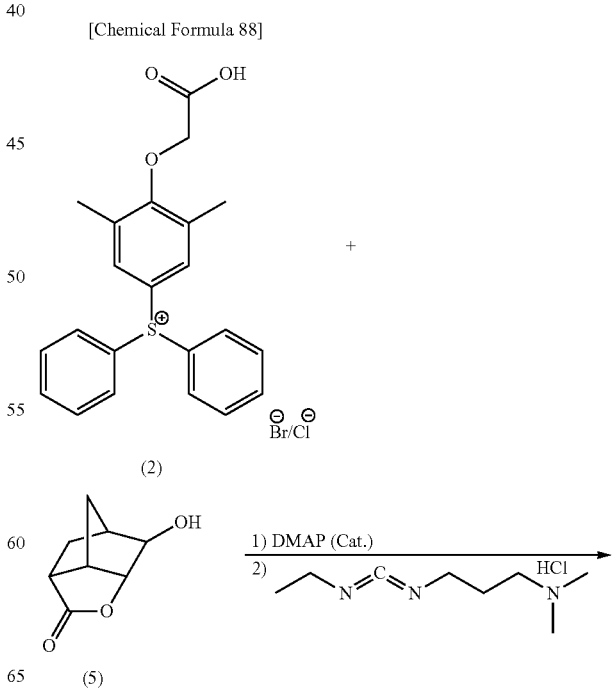

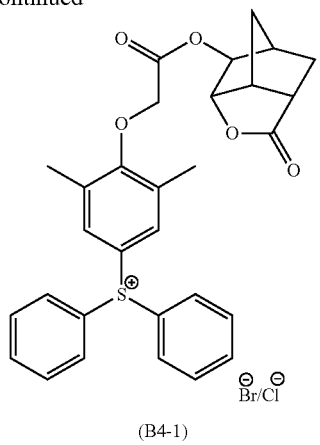

(B4-1)

Example 74

Synthesis of Compound (B4-2)

1.8 g of a compound (B4-1), 13.8 g of dichloromethane and 5.2 g of pure water were mixed together, and 1.7 g of potassium perfluorobutanesulfonate was added thereto, followed by stirring at room temperature for one night. Then, the organic phase was separated and washed with 5.2 g of pure water four times. Thereafter, dichloromethane was distilled off under reduced pressure, and the resultant was dried under reduced pressure, thereby obtaining 1.95 g of a compound (B4-2).

The obtained compound (B4-2) was analyzed by NMR.

$^1$H-NMR (DMSO-d6,400 MHz): δ(ppm)=7.74-7.84 (m, 10H, ArH), 7.61 (s, 21-1, ArH), 4.49-4.62 (m, 2H, norbornane), 3.24 (m, 1H, norbonane), 2.44-2.54 (m, 2H, norbonane), 1.91-2.06 (m, 2H, norbornane), 1.57-1.67 (m, 2H, norbornane)

$^{19}$F-NMR (DMSO-d6,376 MHz): δ(ppm)=−77.8, −111.9, −118.5, −122.9

From the results shown above, it was confirmed that the compound (B4-2) had a structure shown below.

[Chemical Formula 89]

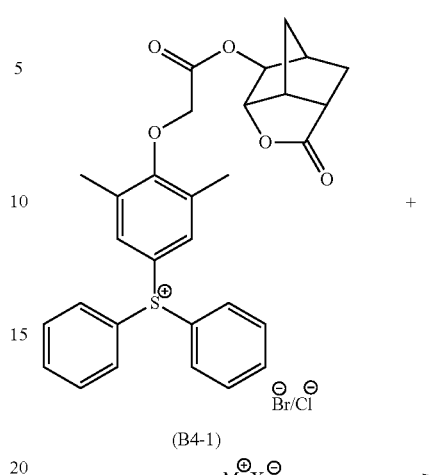

(B4-1)

$M^{\oplus}\text{-}X^{\ominus}$ $\xrightarrow[\text{r.t.}]{\text{CH}_2\text{Cl}_2/\text{H}_2\text{O}}$

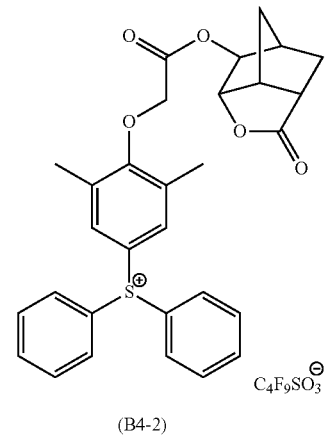

(B4-2)

$M^{\oplus}\text{-}X^{\ominus} = C_4F_9SO_3^{\ominus} K^{\oplus}$

Examples 75 to 96

The same procedure as in Example 74 was performed, except that the compound (M$^+$-X$^-$) was changed to a compound shown in Tables 21 to 28 (equimolar amount). In this manner, products having an anion and a cation as shown in Tables 21 to 28 (compounds (B4-3) to (B4-24)) were obtained.

Each of the obtained compounds was analyzed by NMR. The results are shown in Tables 21 to 28. In Tables 21 to 28, "↑" indicates that the cation of the product is the same as that of the compound (B4-3).

TABLE 21

| Compound | NMR | Compound M+-X− | Product Cation | Product Anion |
|---|---|---|---|---|
| B4-3 | ¹H-NMR(DMSO-d6, 400 MHz): δ (ppm) = 7.74-7.84 (m, 10H, ArH), 7.61 (s, 2H, ArH), 4.49-4.62 (m, 2H, norbornane), 3.24 (m, 1H, norbornane), 2.44-2.54 (m, 2H, norbornane), 1.91-2.06 (m, 2H, norbornane), 1.57-1.67 (m, 2H, norbornane) <br> ¹⁹F-NMR (DMSO-d6, 376 MHz): δ (ppm) = −75.0 | CF$_3$SO$_3^\ominus$ K$^\oplus$ | 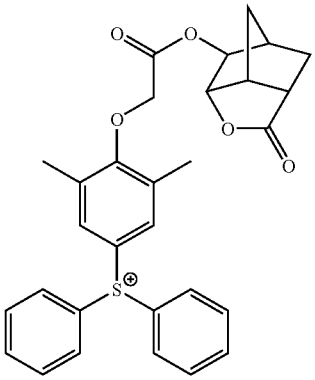 | CF$_3$SO$_3^\ominus$ |
| B4-4 | ¹H-NMR(DMSO-d6, 400 MHz): δ (ppm) = 7.74-7.84 (m, 10H, ArH), 7.61 (s, 2H, ArH), 4.49-4.62 (m, 2H, norbornane), 3.24 (m, 1H, norbornane), 2.44-2.54 (m, 2H, norbornane), 1.91-2.06 (m, 2H, norbornane), 1.57-1.67 (m, 2H, norbornane) <br> ¹⁹F-NMR (DMSO-d6, 376 MHz): δ (ppm) = −77.3, −112.5, −121.7 | C$_3$F$_7$SO$_3^\ominus$ K$^\oplus$ | ↑ | C$_3$F$_7$SO$_3^\ominus$ |

TABLE 22

| Compound | NMR | Compound M+-X− | Product Cation | Product Anion |
|---|---|---|---|---|
| B4-5 | ¹H-NMR(DMSO-d6, 400 MHz): δ (ppm) = 7.74-7.84 (m, 10H, ArH), 7.61 (s, 2H, ArH), 4.49-4.62 (m, 2H, norbornane), 3.24 (m, 1H, norbornane), 2.44-2.54 (m, 2H, norbornane), 1.91-2.06 (m, 2H, norbornane), 1.57-1.67 (m, 2H, norbornane) <br> ¹⁹F-NMR(DMSO-d6, 376 MHz): δ (ppm) = −116.9, −123.0 | cyclic (O$_2$S-N$^\ominus$-SO$_2$-CF$_2$-CF$_2$-CF$_2$) K$^\oplus$ | ↑ | cyclic (O$_2$S-N$^\ominus$-SO$_2$-CF$_2$-CF$_2$-CF$_2$) |
| B4-6 | ¹H-NMR(DMSO-d6, 400 MHz): δ (ppm) = 7.74-7.84 (m, 10H, ArH), 7.61 (s, 2H, ArH), 4.49-4.62 (m, 2H, norbornane), 3.24 (m, 1H, norbornane), 2.44-2.54 (m, 2H, norbornane), 1.91-2.06 (m, 2H, norbornane), 1.57-1.67 (m, 2H, norbornane) <br> ¹⁹F-NMR(DMSO-d6, 376 MHz): δ (ppm) = −75.9, −76.0, −114.7 | F$_3$CF$_2$C-S(O$_2$)-N$^\ominus$-S(O$_2$)-CF$_3$  K$^\oplus$ | ↑ | F$_3$CF$_2$C-S(O$_2$)-N$^\ominus$-S(O$_2$)-CF$_3$ |

TABLE 23

| Compound | NMR | Compound M+-X− |
|---|---|---|
| B4-7 | ¹H-NMR(DMSO-d6, 400 MHz): δ (ppm) = 7.74-7.84 (m, 10H, ArH), 7.61 (s, 2H, ArH), 5.83-5.92 (m, 1H, anion CH), 5.41 (dd, 1H, anion CH), 5.21 (dd, 1H, anion CH), 4.49-4.62 (m, 2H, norbornane), 4.45 (s, 2H, anion CH2), 3.24 (m, 1H, norbornane), 2.44-2.54 (m, 2H, norbornane), 1.91-2.06 (m, 2H, norbornane), 1.57-1.67 (m, 2H, norbornane) <br> ¹⁹F-NMR(DMSO-d6, 376 MHz): δ (ppm) = −80.0, −113.0 | CH$_2$=CHCH$_2$-O-CF$_2$-CF$_2$-SO$_3^\ominus$  Li$^\oplus$ |
| B4-8 | ¹H-NMR(DMSO-d6, 400 MHz): δ (ppm) = 7.51-7.96 (m, 19H, ArH + naph), 5.20 (s, 2H, anion CH2), 4.49-4.62 (m, 2H, norbornane), 3.24 (m, 1H, norbornane), 2.44-2.54 (m, 2H, norbornane), 1.91-2.06 (m, 2H, norbornane), 1.57-1.67 (m, 2H, norbornane) <br> ¹⁹F-NMR(DMSO-d6, 376 MHz): δ (ppm) = −80.5, −113.7 | naphthyl-CH$_2$-O-CF$_2$-CF$_2$-SO$_3^\ominus$  Li$^\oplus$ |

TABLE 23-continued

| | | |
|---|---|---|
| B4-9 | ¹H-NMR(DMSO-d6, 400 MHz): δ (ppm) = 7.74-7.84 (m, 10H, ArH), 7.61 (s, 2H, ArH), 4.49-4.62 (m, 2H, norbornane), 3.24 (m, 1H, norbornane), 2.44-2.54 (m, 2H, norbornane), 1.91-2.09 (m, 11H, norbornane + adamantane), 1.57-1.67 (m, 8H, norbornane + adamantane)<br>¹⁹F-NMR(DMSO-d6, 376 MHz): δ (ppm) = −70.1, −113.4 | 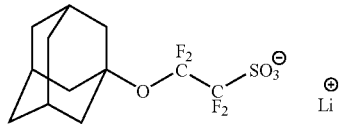 |

| | | Product | |
|---|---|---|---|
| Compound | Cation | Anion | |
| B4-7 | ↑ | 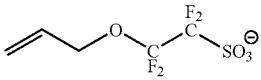 | |
| B4-8 | ↑ | 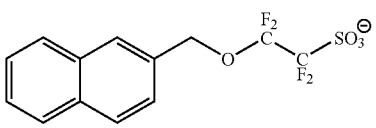 | |
| B4-9 | ↑ | 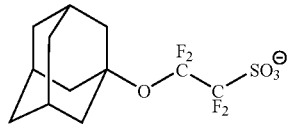 | |

TABLE 24

| Compound | NMR | Compound M⁺-X⁻ |
|---|---|---|
| B4-10 | ¹H-NMR(DMSO-d6, 400 MHz): δ (ppm) = 7.74-7.84 (m, 10H, ArH), 7.61 (s, 2H, ArH), 4.49-4.62 (m, 2H, norbornane), 3.24 (m, 1H, norbornane), 2.44-2.54 (m, 2H, norbornane), 1.91-2.06 (m, 2H, norbornane), 1.57-1.67 (m, 2H, norbornane)<br>¹⁹F-NMR(DMSO-d6, 376 MHz): δ (ppm) = −73.7 | 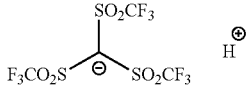 |
| B4-11 | ¹H-NMR(DMSO-d6, 400 MHz): δ (ppm) = 7.74-7.84 (m, 10H, ArH), 7.61 (s, 2H, ArH), 4.49-4.62 (m, 2H, norbornane), 3.24 (m, 1H, norbornane), 2.44-2.54 (m, 2H, norbornane), 1.91-2.06 (m, 2H, norbornane), 1.57-1.67 (m, 2H, norbornane)<br>¹⁹F-NMR(DMSO-d6, 376 MHz): δ (ppm) = −161.1, −149.7, −131.6, −76.2 | 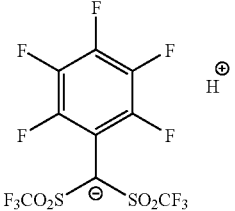 |
| B4-12 | ¹H-NMR(DMSO-d6, 400 MHz): δ (ppm) = 7.74-7.84 (m, 10H, ArH), 7.61 (s, 2H, ArH), 4.49-4.62 (m, 2H, norbornane), 3.24 (m, 1H, norbornane), 2.44-2.54 (m, 2H, norbornane), 1.91-2.06 (m, 2H, norbornane), 1.57-1.88 (m, 17H, norbornane + adamantane)<br>¹⁹F-NMR(DMSO-d6, 376 MHz): δ (ppm) = −74.5 | 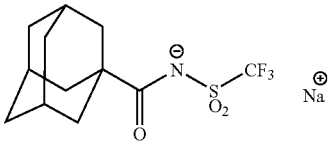 |

| | | Product | |
|---|---|---|---|
| Compound | Cation | Anion | |
| B4-10 | ↑ | 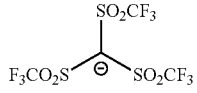 | |

TABLE 24-continued

| Compound | | Structure |
|---|---|---|
| B4-11 | ↑ | Pentafluorophenyl with CH(SO₂CF₃)(SO₂CF₃)⁻ |
| B4-12 | ↑ | Adamantane-C(O)-N⁻-SO₂CF₃ |

TABLE 25

| Compound | NMR | Compound M⁺-X⁻ |
|---|---|---|
| B4-13 | ¹H-NMR(DMSO-d6, 400 MHz): δ (ppm) = 7.74-7.84 (m, 10H, ArH), 7.61 (s, 2H, ArH), 4.49-4.62 (m, 2H, norbornane), 4.19 (s, 2H, anion CH2), 3.24 (m, 1H, norbornane), 2.44-2.54 (m, 2H, norbornane), 1.91-2.06 (m, 2H, norbornane), 1.55-1.87 (m, 17H, norbornane + adamantane) ¹⁹F-NMR(DMSO-d6, 376 MHz): δ (ppm) = −77.7 | Adamantyl-CH₂-C(O)-N⁻(SO₂CF₃), Na⁺ |
| B4-14 | ¹H-NMR(DMSO-d6, 400 MHz): δ (ppm) = 7.74-7.84 (m, 10H, ArH), 7.61 (s, 2H, ArH), 4.49-4.62 (m, 2H, norbornane), 3.24 (m, 1H, norbornane), 2.77-2.81 (m, 1H, cyclohexyl), 2.44-2.54 (m, 2H, norbornane), 1.91-2.08 (m, 4H, norbornane + cyclohexyl), 1.73-1.75 (m, 2H, cyclohexyl), 1.57-1.67 (m, 3H, norbornane + cyclohexyl), 1.07-1.33 (m, 5H, cyclohexyl) ¹⁹F-NMR(DMSO-d6, 376 MHz): δ (ppm) = −74.7 | Cyclohexyl-SO₂-N⁻-SO₂CF₃, Na⁺ |
| B4-15 | ¹H-NMR(DMSO-d6, 400 MHz): δ (ppm) = 7.74-7.84 (m, 10H, ArH), 7.61 (s, 2H, ArH), 4.49-4.62 (m, 2H, norbornane), 3.24 (m, 1H, norbornane), 2.44-2.54 (m, 2H, norbornane), 2.13 (m, 3H, adamantane), 1.91-2.06 (m, 8H, norbornane + adamantane), 1.57-1.67 (m, 8H, norbornane + adamanatane) ¹⁹F-NMR(DMSO-d6, 376 MHz): δ (ppm) = −69.2, −76.0, −112.9 | Adamantyl-O-CF₂-CF₂-SO₂-N⁻-SO₂CF₃, Na⁺ |

| | Product | |
|---|---|---|
| Compound | Cation | Anion |
| B4-13 | ↑ | Adamantyl-CH₂-C(O)-N⁻-SO₂CF₃ |
| B4-14 | ↑ | Cyclohexyl-SO₂-N⁻-SO₂CF₃ |
| B4-15 | ↑ | Adamantyl-O-CF₂-CF₂-SO₂-N⁻-SO₂CF₃ |

TABLE 26

| Compound | NMR | Compound M⁺-X⁻ |
|---|---|---|
| B4-16 | ¹H-NMR(DMSO-d6, 400 MHz): δ (ppm) = 7.74-7.84 (m, 10H, ArH), 7.61 (s, 2H, ArH), 4.49-4.62 (m, 2H, norbornane), 3.24 (m, 1H, norbornane), 2.88 (d, 1H, anion CH), 2.66-2.74 (m, 1H, anion CH), 2.44-2.54 (m, 2H, norbornane), 2.37 (d, 1GH, anion CH), 2.17-2.24 (m, 1H, anion CH), 1.91-2.06 (m, 3H, norbornane + anion CH), 1.74-1.89 (m, 2H, anion CH2), 1.57-1.67 (m, 2H, norbornane), 1.22-1.29 (m, 2H, anion CH2), 1.03 (s, 3H, anion CH3), 0.71 (s, 3H, anion CH3) | |
| B4-17 | ¹H-NMR(DMSO-d6, 400 MHz): δ (ppm) = 7.74-7.84 (m, 10H, ArH), 7.61 (s, 2H, ArH), 4.40-4.62 (m, 6H, norbornane + anion CH2), 3.24 (m, 1H, norbornane), 2.44-2.54 (m, 2H, norbornane), 1.91-2.06 (m, 2H, norbornane), 1.57-1.67 (m, 2H, norbornane) <br> ¹⁹F-NMR(DMSO-d6, 376 MHz): δ (ppm) = −106.7, −154.0, −160.0, −161.5 | |
| B4-18 | ¹H-NMR(DMSO-d6, 400 MHz): δ (ppm) = 8.74-8.82 (m, 2H, Py-H), 7.74-7.84 (m, 12H, ArH + Py-H), 7.61 (s, 2H, ArH), 4.49-4.62 (m, 6H, norbornane + Py-H), 3.24 (m, 1H, norbornane), 2.44-2.54 (m, 2H, norbornane), 1.91-2.06 (m, 2H, norbornane), 1.57-1.67 (m, 2H, norbornane) <br> ¹⁹F-NMR(DMSO-d6, 376 MHz): δ (ppm) = −106.5 | |

| | | Product | |
|---|---|---|---|
| Compound | Cation | Anion | |
| B4-16 | ↑ | | |
| B4-17 | ↑ | | |
| B4-18 | ↑ | | |

TABLE 27

| Compound | NMR | Compound M⁺-X⁻ |
|---|---|---|
| B4-19 | ¹H-NMR(DMSO-d6, 400 MHz): δ (ppm) = 7.74-7.84 (m, 10H, ArH), 7.61 (s, 2H, ArH), 5.46 (t, 1H, oxo-norbornane), 4.97 (s, 1H, oxo-norbornane), 4.71 (d, 1H, oxo-norbornane), 4.49-4.62 (m, 3H, norbornane + oxo-norbornane), 3.24 (m, 1H, norbornane), 2.69-2.73 (m, 1H, oxo-norbornane), 2.44-2.54 (m, 2H, norbornane), 1.91-2.16 (m, 4H, norbornane + oxo-norbornane), 1.57-1.67 (m, 2H, norbornane) <br> ¹⁹F-NMR(DMSO-d6, 376 MHz): δ (ppm) = −107.1 | |

TABLE 27-continued

| | | |
|---|---|---|
| B4-20 | $^1$H-NMR(DMSO-d6, 400 MHz): δ (ppm) = 7.74-7.84 (m, 10H, ArH), 7.61 (s, 2H, ArH), 4.41-4.62 (m, 4H, norbornane + anion CH2), 4.23 (t, 2H, anion CH2), 3.24 (m, 1H, norbornane), 0.79-2.89 (m, 27H, norbornane + undecanoyl)<br>$^{19}$F-NMR(DMSO-d6, 376 MHz): δ (ppm) = −106.8 | 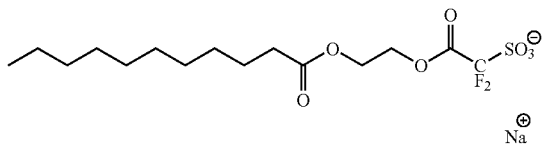 |
| B4-21 | $^1$H-NMR(DMSO-d6, 400 MHz): δ (ppm) = 7.74-7.84 (m, 10H, ArH), 7.61 (s, 2H, ArH), 4.40-4.62 (m, 4H, norbornane + anion CH2), 4.21 (t, 2H, anion CH2), 3.24 (m, 1H, norbornane), 2.44-2.54 (m, 2H, norbornane), 1.61-2.06 (m, 19H, norbornane + adamantane)<br>$^{19}$F-NMR(DMSO-d6, 376 MHz): δ (ppm) = −106.6 | 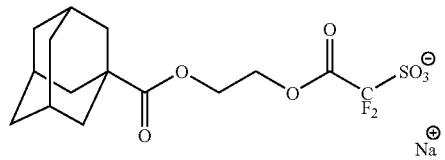 |

| | | Product | |
|---|---|---|---|
| Compound | Cation | | Anion |
| B4-19 | ↑ | | ![structure] |
| B4-20 | ↑ | | ![structure] |
| B4-21 | ↑ | | ![structure] |

TABLE 28

| Compound | NMR | Compound $M^+$-$X^-$ |
|---|---|---|
| B4-22 | $^1$H-NMR(DMSO-d6, 400 MHz): δ (ppm) = 7.74-7.84 (m, 10H, ArH), 7.61 (s, 2H, ArH), 4.40-4.62 (m, 4H, norbornane + anion CH2), 4.20 (t, 2H, anion CH2), 3.24 (m, 1H, norbornane), 2.44-2.54 (m, 2H, norbornane), 1.53-2.06 (m, 21H, norbornane + anion CH2 + adamantane)<br>$^{19}$F-NMR(DMSO-d6, 376 MHz): δ (ppm) = −111.2 | ![structure] |
| B4-23 | $^1$H-NMR(DMSO-d6, 400 MHz): δ (ppm) = 7.74-7.84 (m, 10H, ArH), 7.61 (s, 2H, ArH), 4.49-4.62 (m, 4H, norbornane + CF2CH2), 3.24 (m, 1H, norbornane), 2.44-2.54 (m, 2H, norbornane), 1.91-2.06 (m, 5H, norbornane + adamantane), 1.82 (m, 6H, m adamantane), 1.57-1.67 (m, 8H, norbornane + adamantane)<br>$^{19}$F-NMR(DMSO-d6, 376 MHz): δ (ppm) = −111.2 | ![structure] |
| B4-24 | $^1$H-NMR(DMSO-d6, 400 MHz): δ (ppm) = 7.74-7.84 (m, 10H, ArH), 7.61 (s, 2H, ArH), 4.78 (m, 1H, sultone), 4.49-4.66 (m, 3H, norbornane + sultone), 3.88 (t, 1H, sultone), 3.34 (m, 1H, sultone), 3.24 (m, 1H, norbornane), 2.44-2.54 (m, 3H, norbornane + sultone), 1.73-2.21 (m, 6H, norbornane + sultone), 1.57-1.67 (m, 2H, norbornane)<br>$^{19}$F-NMR(DMSO-d6, 376 MHz): δ (ppm) = −107.7 | ![structure] |

TABLE 28-continued

| | Compound | Product Cation | Anion |
|---|---|---|---|
| | B4-22 | ↑ |  |
| | B4-23 | ↑ | 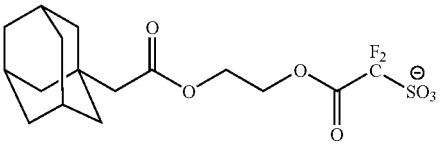 |
| | B4-24 | ↑ | 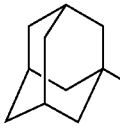 |

<Evaluation of Decomposability in Alkali Developing Solution>

With respect to the compounds obtained in Examples 1 to 96, the decomposability in an alkali developing solution was evaluated.

The evaluation was performed by dissolving 0.1 g of a compound in 0.9 g of a 2.38% by weight aqueous tetramethylammonium hydroxide (TMAH) solution at 23° C., and the resulting solution was analyzed by liquid chromatography.

As a result, it was confirmed that all of the compounds obtained in Examples 1 to 96 could be decomposed by the action of the alkali developing solution to form a carboxylic acid.

Production of Resist Composition

Examples 97 to 108, Comparative Example 1

The components shown in Table 29 were mixed together and dissolved to obtain positive resist compositions.

TABLE 29

| | Component (A) | Component (B) | Component (D) | Component (E) | Component (S) | |
|---|---|---|---|---|---|---|
| Example 97 | (A)-1 [100] | (B)-1 [11.61] | (D)-1 [1.20] | (E)-1 [1.32] | (S)-1 [2400] | (S)-2 [10] |
| Example 98 | (A)-1 [100] | (B)-2 [11.96] | (D)-1 [1.20] | (E)-1 [1.32] | (S)-1 [2400] | (S)-2 [10] |
| Example 99 | (A)-1 [100] | (B)-3 [12.42] | (D)-1 [1.20] | (E)-1 [1.32] | (S)-1 [2400] | (S)-2 [10] |
| Example 100 | (A)-1 [100] | (B)-4 [11.14] | (D)-1 [1.20] | (E)-1 [1.32] | (S)-1 [2400] | (S)-2 [10] |
| Example 101 | (A)-1 [100] | (B)-5 [11.48] | (D)-1 [1.20] | (E)-1 [1.32] | (S)-1 [2400] | (S)-2 [10] |
| Example 102 | (A)-1 [100] | (B)-6 [11.81] | (D)-1 [1.20] | (E)-1 [1.32] | (S)-1 [2400] | (S)-2 [10] |
| Example 103 | (A)-1 [100] | (B)-7 [11.28] | (D)-1 [1.20] | (E)-1 [1.32] | (S)-1 [2400] | (S)-2 [10] |
| Example 104 | (A)-1 [100] | (B)-8 [11.62] | (D)-1 [1.20] | (E)-1 [1.32] | (S)-1 [2400] | (S)-2 [10] |
| Example 105 | (A)-1 [100] | (B)-9 [12.07] | (D)-1 [1.20] | (E)-1 [1.32] | (S)-1 [2400] | (S)-2 [10] |
| Example 106 | (A)-1 [100] | (B)-10 [11.11] | (D)-1 [1.20] | (E)-1 [1.32] | (S)-1 [2400] | (S)-2 [10] |
| Example 107 | (A)-1 [100] | (B)-11 [11.45] | (D)-1 [1.20] | (E)-1 [1.32] | (S)-1 [2400] | (S)-2 [10] |
| Example 108 | (A)-1 [100] | (B)-12 [11.78] | (D)-1 [1.20] | (E)-1 [1.32] | (S)-1 [2400] | (S)-2 [10] |
| Comparative Example 1 | (A)-1 [100] | (B)-13 [8.00] | (D)-1 [1.20] | (E)-1 [1.32] | (S)-1 [2400] | (S)-2 [10] |

In Table 29, the reference characters indicate the following. Further, the values in brackets [ ] indicate the amount (in terms of parts by weight) of the component added.

(A)-1: a polymeric compound 1 represented by chemical formula (A1-11-1) shown below with Mw=10,000 and Mw/Mn=2.0. In the chemical formula shown below, the subscript numerals shown to the bottom right of the parentheses ( ) indicate the percentage (molar ratio) of the respective structural units within the polymeric compound 1.

[Chemical Formula 90]

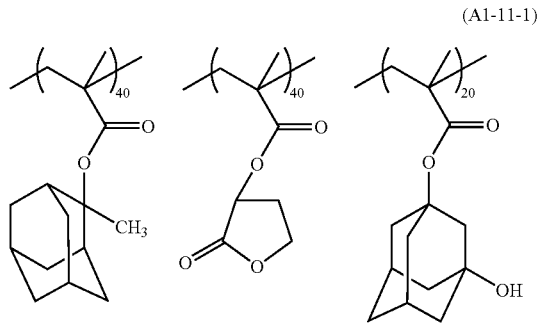

(A1-11-1)

(B)-1: the aforementioned compound (B1-2)
(B)-2: the aforementioned compound (B1-23)
(B)-3: the aforementioned compound (B1-24)
(B)-4: the aforementioned compound (B2-2)
(B)-5: the aforementioned compound (B2-23)
(B)-6: the aforementioned compound (B2-24)
(B)-7: the aforementioned compound (B3-2)
(B)-8: the aforementioned compound (B3-23)
(B)-9: the aforementioned compound (B3-24)
(B)-10: the aforementioned compound (B4-2)
(B)-11: the aforementioned compound (B4-23)
(B)-12: the aforementioned compound (B4-24)
(B)-13: (4-methylphenyl)diphenylsulfonium nonafluoro-n-butanesulfonate
(D)-1: tri-n-pentylamine
(E)-1: salicylic acid
(S)-1: a mixed solvent of PGMEA/PGME=6/4 (weight ratio)
(S)-2: γ-butyrolactone <Evaluation of Lithography Properties>

Using the obtained resist compositions, resist patterns were formed in the following manner, and the lithography properties were evaluated.

[Formation of Resist Pattern]

An organic anti-reflection film composition (product name: ARC29A, manufactured by Brewer Science Ltd.) was applied onto an 8-inch silicon wafer using a spinner, and the composition was then baked at 205° C. for 60 seconds, thereby forming an organic anti-reflection film having a film thickness of 82 nm. Then, each of the resist compositions obtained above was applied onto the anti-reflection film using a spinner, and was then prebaked (FAB) on a hotplate at 110° C. for 60 seconds and dried, thereby forming a resist film having a film thickness of 150 nm.

Subsequently, the resist film was selectively irradiated with an ArF excimer laser (193 um) through a mask pattern (6% halftone), using an ArF exposure apparatus NSR-S302 (manufactured by Nikon Corporation; NA (numerical aperture)=0.60, ⅔ annular illumination).

Thereafter, a post exposure bake (PEB) treatment was conducted at 110° C. for 60 seconds, followed by development for 30 seconds at 23° C. in a 2.38% by weight aqueous solution of tetramethylammonium hydroxide (TMAH). Then, the resist film was washed for 30 seconds with pure water, followed by drying by shaking.

As a result, in each of the examples, a line and space pattern (hereafter, referred to as "LS pattern") having a line width of 120 nm and a pitch of 240 nm was formed on the resist film.

[Sensitivity]

The optimum exposure dose Eop (mJ/cm$^2$; sensitivity) with which the LS pattern having a line width of 120 nm and a pitch of 240 nm could be formed was determined. The results are shown in Tables 30 and 31.

[Evaluation of Line Width Roughness (LWR)]

With respect to each of the LS patterns formed with the above Eop and having a line width of 120 nm and a pitch of 240 nm, the line width at 5 points in the lengthwise direction of the line were measured using a measuring scanning electron microscope (SEM) (product name: S-9220, manufactured by Hitachi, Ltd.; acceleration voltage: 800V), and from the results, the value of 3 times the standard deviation s (i.e., 3s) was calculated as a yardstick of LWR. The results are shown in Tables 30 and 31. The smaller this 3s value is, the lower the level of roughness of the line width, indicating that a LS pattern with a uniform width was obtained.

[Evaluation of EL Margin]

The exposure dose with which an LS pattern having a dimension of the target dimension (line width: 120 nm)±5% (i.e., 114 nm to 126 nm) was formed was determined, and the EL margin (unit: %) was determined by the following formula. The results are shown in Tables 30 and 31.

$$\text{EL margin (\%)} = (|E1-E2|/Eop) \times 100$$

In the formula, E1 represents the exposure dose (mJ/cm$^2$) for forming an LS pattern having a line width of 114 nm, and E2 represents the exposure dose (mJ/cm$^2$) for forming a LS pattern having a line width of 126 mu.

[Evaluation of Mask Error Factor (MEF)]

With the above Eop, LS patterns were formed using a mask pattern targeting a line width of 130 nm and a pitch of 260 nm, and a mask pattern targeting a line width of 120 nm and a pitch of 260 nm, and the MEF value was calculated by the following formula. The results are shown in Tables 30 and 31.

$$MEF = |CD_{130} - CD_{120}| / |MD_{130} - MD_{120}|$$

In the formula, $CD_{130}$ and $CD_{120}$ represent the respective line widths (mu) of the actual LS patterns respectively formed using the mask pattern targeting a line width of 130 nm and the mask pattern targeting a line width of 120 nm. $MD_{130}$ and $MD_{120}$ represent the respective target line widths (nm), meaning $MD_{130}$=130, and $MD_{120}$=120.

A MEF value closer to 1 indicates that a resist pattern faithful to the mask pattern was formed.

[Evaluation of Resist Pattern Shape]

Each of the LS patterns having a line width of 120 nm and a pitch of 240 nm and formed with the above Eop was observed using a scanning electron microscope (SEM), and the cross-sectional shape of the LS pattern was evaluated. The results are shown in Tables 30 and 31.

TABLE 30

| | Example 97 | Example 98 | Example 99 | Example 100 | Example 101 | Example 102 | Example 103 | Example 104 | Example 105 |
|---|---|---|---|---|---|---|---|---|---|
| Eop (mJ/cm$^2$) | 47.1 | 61.2 | 64.0 | 46.2 | 60.0 | 62.7 | 42.0 | 54.6 | 57.1 |
| LWR (nm) | 10.1 | 9.79 | 10.2 | 11.1 | 10.7 | 11.2 | 9.8 | 9.5 | 9.9 |
| EL margin (%) | 8.9 | 9.5 | 9.8 | 8.7 | 9.3 | 9.6 | 7.0 | 7.4 | 7.7 |
| MEF | 2.26 | 1.78 | 2.77 | 2.48 | 1.95 | 2.99 | 2.98 | 2.35 | 2.10 |
| Shape | Rectangular | Rectangular | Rectangular | Rectangular | Rectangular | Rectangular | Rectangular | Rectangular | Rectangular |

TABLE 31

| | Example 106 | Example 107 | Example 108 | Comparative Example 1 |
|---|---|---|---|---|
| Eop (mJ/cm$^2$) | 45.9 | 59.7 | 62.4 | 31.7 |
| LWR (nm) | 10.4 | 10.0 | 10.5 | 13.0 |
| EL margin (%) | 8.7 | 9.3 | 9.6 | 6.7 |
| MEF | 2.44 | 1.92 | 2.99 | 3.01 |
| Shape | Rectangular | Rectangular | Rectangular | Rounded top |

From the results shown in Tables 30 and 31, it was confirmed that the resist composition of Examples 97 to 108 according to the present invention were superior to the resist composition of Comparative Example 1 in that they exhibited excellent lithography properties and a resist pattern having an excellent shape could be formed.

Further, from the results above, it is expected that the compounds of Examples 1 to 96 which were not used as an acid generator in Examples 97 to 108 also exhibit the same effects, i.e., exhibit excellent lithography properties and a resist pattern having an excellent shape can be formed.

Production of Resist Composition

Examples 109 and 110, Reference Example 1

The components shown in Table 32 were mixed together and dissolved to obtain positive resist compositions.

TABLE 32

| | Component (A) | | Component (B) | Component (S) |
|---|---|---|---|---|
| Reference Example 1 | (A)-2 [50] | (A)-3 [50] | (B)-14 [9.7] | (S)-1 [2900] |
| Example 109 | (A)-2 [50] | (A)-3 [50] | (B)-3 [10.1] | (S)-1 [2900] |
| Example 110 | (A)-2 [50] | (A)-3 [50] | (B)-3 [10.1] | (S)-3 [2900] |

In Table 32, the reference characters indicate the following. Further, the values in brackets [ ] indicate the amount (in terms of parts by weight) of the component added.

(A)-2: polymeric compound 2 shown below (A)-3: polymeric compound 3 shown below

[Chemical Formula 91]

Polymeric compound 2

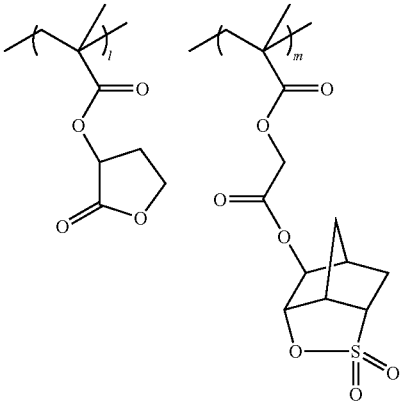

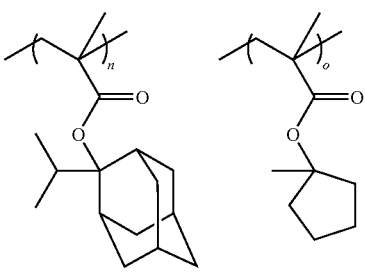

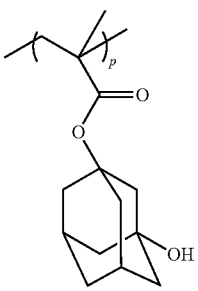

[l/m/n/o/p=35/21/24/13/7, Mw7900, Mw/Mn1.78]

[Chemical Formula 92]

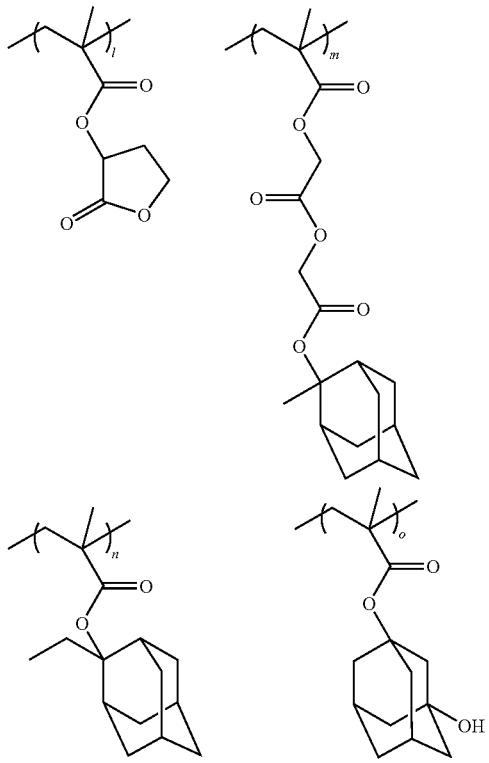

Polymeric compound 3

[l/m/n/o=50/10/30/10, Mw9200, Mw/Mn1.88]
(B)-3: the aforementioned compound (B1-24)
(B)-14: a compound represented by a chemical formula shown below

[Chemical Formula 93]

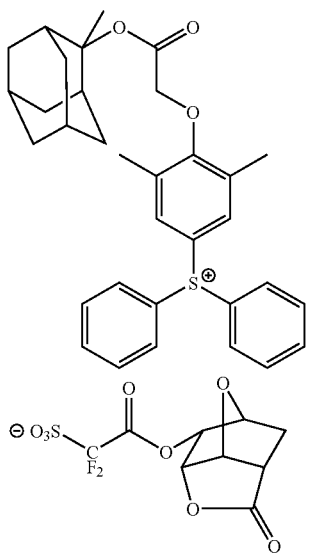

(S)-1: a mixed solvent of PGMEA/PGME=6/4 (weight ratio)
(S)-3: a mixed solvent of PGMEA/PGME/cyclohexanone=45/30/25 (weight ratio)

<Evaluation of Lithography Properties>

Using the obtained resist compositions, resist patterns were formed in the following manner, and evaluations were performed as follows.

[Formation of Resist Pattern]

An organic anti-reflection film composition (product name: ARC29A, manufactured by Brewer Science Ltd.) was applied onto an 12-inch silicon wafer using a spinner, and the composition was then baked at 205° C. for 60 seconds, thereby forming an organic anti-reflection film having a film thickness of 89 nm. Then, each of the resist compositions of Examples 109 and 110 and Reference Example 1 was applied onto the anti-reflection film using a spinner, and was then prebaked (PAB) on a hotplate at 90° C. for 60 seconds and dried, thereby forming a resist film having a film thickness of 100 nm.

Subsequently, a coating solution for forming a protection film (product name: TJLC-075; manufactured by Tokyo Ohka Kogyo Co., Ltd.) was applied onto the resist film using a spinner, and then heated at 90° C. for 60 seconds, thereby forming a top coat with a film thickness of 35 nm.

Thereafter, using an ArF exposure apparatus for immersion lithography (product name: NSR-S609B, manufactured by Nikon Corporation, NA (numerical aperture)=1.07, σ0.97), the resist film having a top coat formed thereon was selectively irradiated with an ArF excimer laser (193 nm) through a mask pattern for forming a hole pattern.

Next, a post exposure bake (PEB) treatment was conducted at a temperature indicated in Table 33 for 60 seconds, followed by alkali development for 30 seconds at 23° C. in a 2.38% by weight aqueous solution of tetramethylammonium hydroxide (TMAH) (product name: NMD-3; manufactured by Tokyo Ohka Kogyo Co., Ltd.). Then, the resist was washed for 25 seconds with pure water, followed by drying by shaking.

As a result, in each of the examples, a contact hole pattern in which holes having a diameter of 90 nm were equally spaced (pitch: 140 nm) was formed on the resist film (hereafter, this contact hole pattern is referred to as "dense CH pattern").

Subsequently, using the optimum exposure dose Eop (mJ/cm$^2$) with which the aforementioned dense CH pattern was formed, a contact hole pattern in which holes having a hole diameter of 90 nm were equally spaced (pitch: 540 nm) were formed in the same manner as in the formation of the dense CH pattern (hereafter, this contact hole pattern is referred to as "isolated CH pattern").

[Sensitivity]

The optimum exposure dose Eop (mJ/cm$^2$) with which the aforementioned dense CH pattern and isolated CH pattern were formed was determined. The results are shown in Table 33.

[Evaluation of Depth of Focus (DOF)]

With respect to each of the resist compositions, the exposure dose was changed at predetermined intervals, and the depth of focus (DOF) was determined for each exposure dose. (As a matter of form, for example, patterns were formed while changing the depth of focus at a predetermined exposure dose, and the depth of focus with which a pattern could be formed with a predetermined size range was determined. This procedure was performed for each exposure dose. Finally, a matrix data x-direction: exposure dose, y-direction: depth of focus, and cell: size of pattern formed was obtained.)

Subsequently, on the basis of the data obtained by the measurement, a graph was plotted, taking the EL margin (unit: %) on the vertical axis and DOF (unit: μm) on the horizontal axis, by a process window analysis method using a ProDATA software (FINLE Technologies, Inc.). By this method, the DOF (or EL margin) with which a specific EL margin (or DOF) could be obtained can be standardized, and the comparison of properties between different resist samples can be precisely assessed. As one example, a graph showing the relationship between the EL margin and DOF with respect to a dense CH pattern is illustrated by FIG. 1.

The DOF value (unit: μm) at an EL margin of 5% is shown in Table 33. With respect to dense CH patterns, the DOF value at an EL margin of 10% is also shown.

The larger the DOF value, the better the DOF properties.

In the graph of FIG. 1, the larger the EL margin value against DOF (i.e., larger the area beneath the curve on the graph), the better the process window.

carbonate and 1N-HClaq in this order. Thereafter, the solvent was distilled off under reduced pressure, and the resulting product was dried, thereby obtaining a compound (7).

The results of instrumental analysis of the obtained compound (7) were as follows.

$^1$H-NMR (CDCl$_3$, 400 MHz): δ(ppm)=6.22 (s, 1H, H$^a$), 5.70 (s, 1H, H$^b$), 4.71-4.85 (m, 2H, H$^{c,d}$), 4.67 (s, 2H, H$^k$), 3.40-3.60 (m, 2H$^{e,f}$), 2.58-2.70 (m, 1H, H$^g$), 2.11-2.21 (m, 2H, H$^h$), 2.00 (s, 3H, H$^i$), 1.76-2.09 (m, 2H, H$^j$).

TABLE 33

| | Dense CH pattern | | | Isolated CH pattern | | |
|---|---|---|---|---|---|---|
| | PEB temperature (° C.) | Eop (mJ/cm$^2$) | DOF (5% EL) (μm) | DOF (10% EL) (μm) | PEB temperature (° C.) | Eop (mJ/cm$^2$) | DOF (5% EL) (μm) |
| Ref. Ex. 1 | 85 | 38.2 | 3.2 | 0.10 | 85 | 39.9 | 0.13 |
| Ex. 109 | 90 | 31.3 | 3.5 | 0.14 | 90 | 32.2 | 0.15 |
| Ex. 110 | 90 | 27.7 | 3.5 | 0.17 | 90 | 27.9 | 0.15 |

From the results shown in Table 33, it was confirmed that the resist compositions of Examples 109 and 110 according to the present invention exhibit excellent DOF, as compared to the resist composition of Reference Example 1.

From the results of DOF (10% EL) shown in Table 33 and the graph of FIG. 1, the resist composition of Example 110 exhibited larger process window than the resist composition of Example 109, as seen from the fact that the area beneath the curve on the graph is larger.

[Evaluation of Resist Pattern Shape]

With respect to the CH patterns formed using the resist compositions of Examples 109 and 110 and Reference Example 1, the shape of the holes was observed using a scanning electron microscope (SEM) (product name: SEM S-9220, manufactured by Hitachi, Ltd.).

As a result, it was confirmed that all CH patterns exhibited excellent circularity and in-plane uniformity, and the CH pattern formed using the resist composition of Example 109 exhibited particularly good properties.

<Synthesis of Resin Component (A1)>

The aforementioned polymeric compounds 2 and 3 were synthesized in accordance with the following polymer synthesis examples. The compound (7) and the compound (6) used in the polymer synthesis examples were synthesized as follows.

Synthesis Example of Compound (7)

300 ml of a THF solution containing 20 g (105.14 mmol) of an alcohol (1), 30.23 g (157.71 mmol) of ethyldiisopropylaminocarbodiimide (EDCI) hydrochloride and 0.6 g (5 mmol) of dimethylaminopyridine (DMAP) was added to a 500 ml three-necked flask in nitrogen atmosphere, and 16.67 g (115.66 mmol) of a precursor (1) was added thereto while cooling with ice (0° C.), followed by stirring at room temperature for 12 hours.

After conducting thin-layer chromatography (TLC) to confirm that the raw materials had been consumed, 50 ml of water was added to stop the reaction. Then, the reaction solvent was concentrated under reduced pressure, and extraction was conducted with ethyl acetate three times. The obtained organic phase was washed with water, saturated sodium hydrogen-

[Chemical Formula 94]

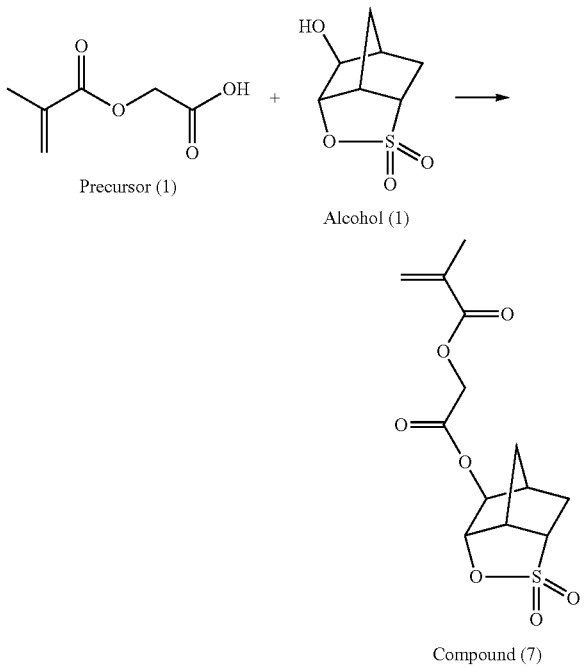

Precursor (1)

Alcohol (1)

Compound (7)

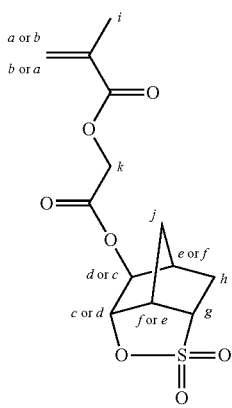

Synthesis Example of Compound (6)

(i) Synthesis of 2-(2-(2-methyl-2-adamantyloxy)-2-oxoethoxy)-2-oxoethanol 37.6 g (494 mmol) of glycolic acid, 700 mL of DMF, 86.5 g (626 mmol) of potassium carbonate, and 28.3 g (170 mmol) of potassium iodide were added to a 2 L three-necked flask equipped with a thermometer, a cooling pipe, and a stirrer, followed by stirring at room temperature for 30 minutes. Then, 300 ml of a dimethylformaldehyde solution containing 100 g (412 mmol) of 2-methyl-2-adamantyl chloroacetate was gradually added thereto. The resultant was heated to 40° C., and stirred for 4 hours. Subsequently, 2,000 ml of diethylether was added to the reaction mixture, followed by filtration. The resulting solution was washed with 500 ml of distilled water three times. Then, crystallization was conducted using a mixed solvent containing 300 ml of toluene and 200 ml of heptane, thereby obtaining 78 g of an objective compound (2-(2-(2-methyl-2-adamantyloxy)-2-oxoethoxy)-2-oxoethanol) in the form of a colorless solid (yield: 67%, GC purity: 99%).

The results of instrumental analysis of the obtained compound were as follows.

$^1$H-NMR: 1.59 (d, 2H, J=12.5 Hz), 1.64 (s, 3H), 1.71-1.99 (m, 10H), 2.29 (m, 2H), 2.63 (t, 1H, J=5.2 Hz), 4.29 (d, 2H, J=5.2 Hz), 4.67 (s, 2H).

$^{13}$C-NMR: 22.35, 26.56, 27.26, 32.97, 34.54, 36.29, 38.05, 60.54, 61.50, 89.87, 165.97, 172.81.

GC-MS: 282 (M+, 0.02%), 165 (0.09%), 149 (40%), 148 (100%), 133 (22%), 117 (2.57%), 89 (0.40%),

From the results above, it was confirmed that the obtained compound was 2-(2-(2-methyl-2-adamantyloxy)-2-oxoethoxy)-2-oxoethanol.

(ii) Synthesis of Compound (6)

Subsequently, 165 g (584 mmol) of 2-(2-(2-methyl-2-adamantyloxy)-2-oxoethoxy)-2-oxoethanol, 2,000 ml of THF, 105 ml (754 mmol) of triethylamine, and 0.165 g (1,000 ppm) of p-methoxyphenol were added to and dissolved in a 2 L three-necked flask equipped with a thermometer, a cooling pipe, and a stirrer.

Then, 62.7 ml (648 mmol) of methacryloyl chloride was gradually added thereto while cooling in an ice bath. The temperature of the resultant was elevated to room temperature, and the resultant was stirred for 3 hours. Subsequently, 1,000 ml of diethylether was added thereto, followed by washing with 200 ml of distilled water 5 times. Thereafter, the extraction liquid was concentrated, thereby obtaining 198 g of an objective compound (compound (6)) in the form of a colorless liquid (yield: 97%, GC purity: 99%).

The results of instrumental analysis of the obtained compound (6) were as follows.

$^1$H-NMR: 1.58 (d, J=12.5 Hz, 2H), 1.63 (s, 3H), 1.71-1.89 (m, 8H), 1.98 (s, 3H), 2.00 (m, 2H), 2.30 (m, 2H), 4.62 (s, 2H), 4.80 (s, 2H), 5.66 (m, 1H), 6.23 (m, 1H).

$^{13}$C-NMR: 18.04, 22.15, 26.42, 27.14, 32.82, 34.38, 36.11, 37.92, 60.44, 61.28, 89.42, 126.79, 135.18, 165.61, 166.30, 167.20.

GC-MS: 350 (M+, 1.4%), 206 (0.13%), 149 (47%), 148 (100%), 133 (20%), 69 (37%).

Polymer Synthesis Example

The type of monomers, the initial molar ratio, and the amount of the polymerization initiator were appropriately selected depending on the objective polymer to be produced, and the polymeric compound 2 and the polymeric compound 3 were produced as follows.

Predetermined monomers selected from monomers (6) to (12) were added to a three-necked flask equipped with a thermometer and a reflux tube and dissolved in methyl ethyl ketone (MEK), and 2,2'-azobis(isobutyrate) (V-601) as a polymerization initiator was added to and dissolved therein. The resultant was dropwise added to MEK heated to 78° C. in a nitrogen atmosphere over 3 hours. Thereafter, the reaction solution was heated for 4 hour while stirring, and then cooled to room temperature. The obtained reaction polymer solution was dropwise added to an excess amount of n-heptane, and an operation to deposit a polymer was conducted. Thereafter, the precipitated white powder was separated by filtration, followed by washing with a n-heptane/isopropylalcohol mixed solvent and drying, thereby obtaining the respective polymeric compounds as objective compounds.

With respect to the polymeric compound 2, the weight average molecular weight (Mw) and the dispersity (Mw/Mn) were determined by the polystyrene equivalent value as measured by gel permeation chromatography (GPC). As a result, it was found that the weight average molecular weight was 7,900, and the dispersity was 1.78.

Further, as a result of an analysis by carbon 13 nuclear magnetic resonance spectroscopy (600 MHz, $^{13}$C-NMR), it was found that the composition of the copolymer (ratio (molar ratio) of the respective structural units within the structural formula) was l/m/n/o/p=35/21/24/13/7.

[Chemical Formula 95]

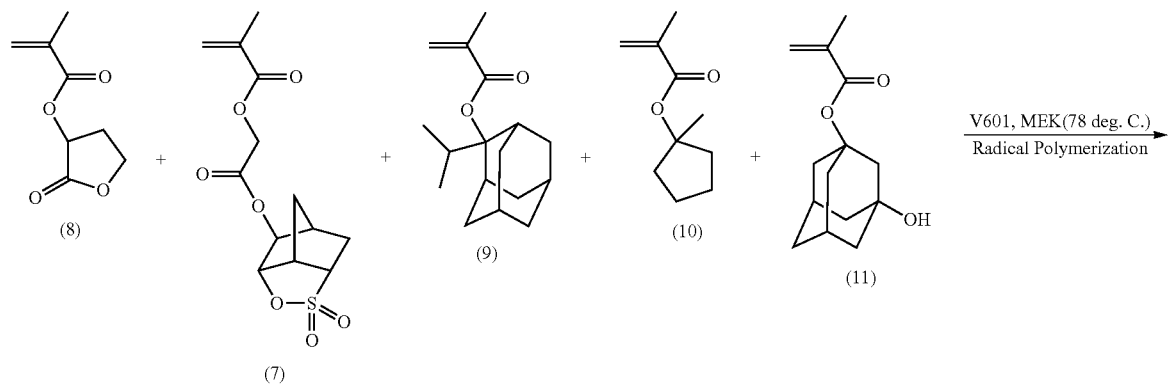

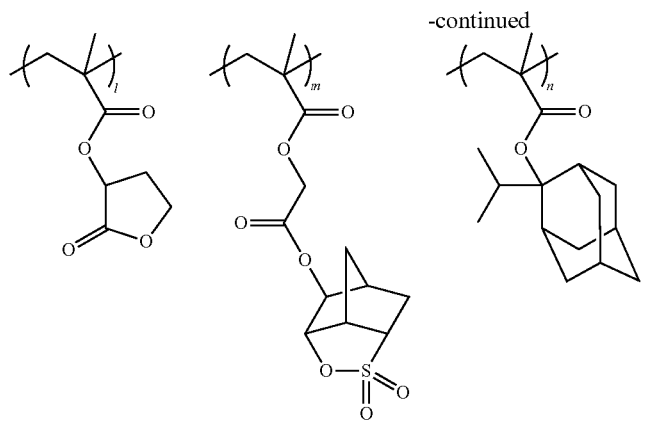

Polymeric compound 2

With respect to the polymeric compound 3, the weight average molecular weight (Mw) and the dispersity (Mw/Mn) were determined in the same manner as described above. As a result, it was found that the weight average molecular weight was 9,200, and the dispersity was 1.88.

Further, the composition of the copolymer (ratio (molar ratio) of the respective structural units within the structural formula) was l/m/n/o=50/10/30/10.

[Chemical Formula 96]

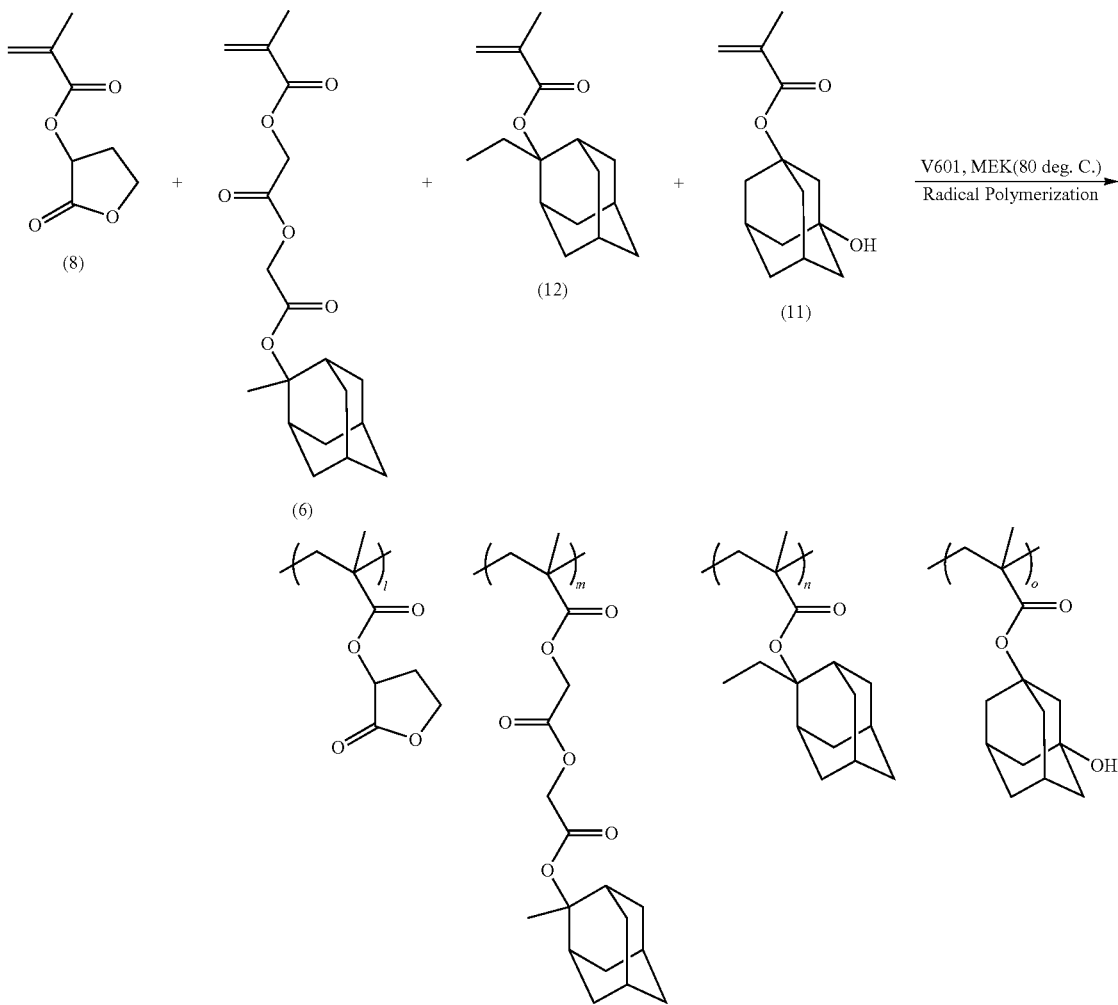

Polymeric compound 3

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition comprising a base component (A) which exhibits changed solubility in an alkali developing solution under action of acid and an acid-generator component (B) which generates acid upon exposure, said acid-generator component (B) comprising an acid generator (B1) comprised of a compound having a cation moiety comprising a group represented by general formula (I) shown below:

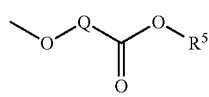

wherein $R^5$ represents an organic group having a carbonyl group, an ester bond or a sulfonyl group; and Q represents a linear or branched alkylene group or a hetero atom-containing linking group.

2. The resist composition according to claim 1, wherein said acid-generator component (B1) is a compound represented by general formula (b1-11) shown below:

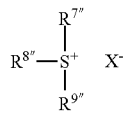

wherein each of $R^{7\prime\prime}$ to $R^{9\prime\prime}$ independently represents an aryl group or an alkyl group, and two of $R^{7\prime\prime}$ to $R^{9\prime\prime}$ may be bonded to each other to form a ring with the sulfur atom, with the provision that at least one of $R^{7\prime\prime}$ to $R^{9\prime\prime}$ represents a substituted aryl group having a group represented by general formula (I) as a substituent; and $X^-$ represents an anion.

3. The resist composition according to claim 2, wherein $X^-$ represents an anion selected from the group consisting of a sulfonate anion, an imide anion, a methide anion and a halogen anion.

4. The resist composition according to claim 1, wherein said base component (A) is a base component which exhibits increased solubility in an alkali developing solution under action of acid.

5. The resist composition according to claim 4, wherein said base component (A) comprises a resin component (A1) comprised of a structural unit (a1) derived from an acrylate ester containing an acid dissociable, dissolution inhibiting group.

6. The resist composition according to claim 5, wherein said resin component (A1) further comprises a structural unit (a2) derived from an acrylate ester containing a lactone-containing cyclic group.

7. The resist composition according to claim 5, wherein said resin component (A1) further comprises a structural unit (a3) derived from an acrylate ester containing a polar group-containing aliphatic hydrocarbon group.

8. The resist composition according to claim 1, which further comprises a nitrogen-containing organic compound (D).

9. A method of forming a resist pattern, comprising: forming a resist film with the resist composition of claim 1; conducting exposure of said resist film; and alkali-developing said resist film to form a resist pattern.

10. A compound represented by general formula (b1-11) shown below:

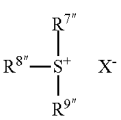

wherein each of $R^{7\prime\prime}$ to $R^{9\prime\prime}$ independently represents an aryl group or an alkyl group, and two of $R^{7\prime\prime}$ to $R^{9\prime\prime}$ may be bonded to each other to form a ring with the sulfur atom, with the provision that at least one of $R^{7\prime\prime}$ to $R^{9\prime\prime}$ represents a substituted aryl group having a group represented by general formula (I) shown below as a substituent; and $X^-$ represents an anion; and

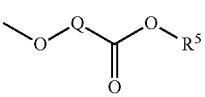

wherein $R^5$ represents an organic group selected from the group consisting of an aromatic hydrocarbon group having 3 to 30 carbon atoms and a carbonyl group, an ester bond or a sulfonyl group; a linear or branched saturated hydrocarbon group having 3 to 15 carbon atoms and; a carbonyl group, an ester bond or sulfonyl group; a cyclic saturated hydrocarbon group having 3 to 20 carbon atoms and a carbonyl group, an ester bond or a sulfonyl group; and a linear or branched unsaturated aliphatic hydrocarbon group having 2 to 5 carbon atoms and a carbonyl group, an ester bond or a sulfonyl group; and Q represents a linear or branched alkylene group or a hetero atom-containing linking group.

11. The compound according to claim 10, wherein $X^-$ represents an anion selected from the group consisting of a sulfonate anion, an imide anion, a methide anion and a halogen anion.

12. An acid generator comprising the compound of claim 10.

13. A resist composition comprising a base component (A) which exhibits changed solubility in an alkali developing solution under action of acid and an acid-generator component (B) which generates acid upon exposure, said acid-generator component (B) comprising an acid generator (B1) comprised of a compound having a cation moiety comprising a group represented by general formula (I) shown below:

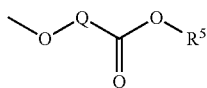
(I)

wherein R⁵ represents an organic group having a sulfonyl group, a linear or branched aliphatic hydrocarbon group having an ester group or a carbonyl group, an aromatic hydrocarbon group having an ester group or a carbonyl group, or a saturated aliphatic cyclic group in which hydrogen atoms bonded to a carbon atom of the cyclic group have been replaced by an oxygen atom; and Q represents a divalent linking group.

14. The resist composition according to claim 13, wherein said acid-generator component (B1) is a compound represented by general formula (b1-11) shown below:

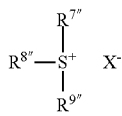
(b1-11)

wherein each of $R^{7\prime\prime}$ to $R^{9\prime\prime}$ independently represents an aryl group or an alkyl group, and two of $R^{7\prime\prime}$ to $R^{9\prime\prime}$ may be bonded to each other to form a ring with the sulfur atom, with the provision that at least one of $R^{7\prime\prime}$ to $R^{9\prime\prime}$ represents a substituted aryl group having a group represented by general formula (I) as a substituent; and $X^-$ represents an anion.

15. The resist composition according to claim 14, wherein X⁻ represents an anion selected from the group consisting of a sulfonate anion, an imide anion, a methide anion and a halogen anion.

16. The resist composition according to claim 13, wherein said base component (A) is a base component which exhibits increased solubility in an alkali developing solution under action of acid.

17. The resist composition according to claim 16, wherein said base component (A) comprises a resin component (A1) comprised of a structural unit (a1) derived from an acrylate ester containing an acid dissociable, dissolution inhibiting group.

18. The resist composition according to claim 17, wherein said resin component (A1) further comprises a structural unit (a2) derived from an acrylate ester containing a lactone-containing cyclic group.

19. The resist composition according to claim 17, wherein said resin component (A1) further comprises a structural unit (a3) derived from an acrylate ester containing a polar group-containing aliphatic hydrocarbon group.

20. The resist composition according to claim 13, which further comprises a nitrogen-containing organic compound (D).

21. A method of forming a resist pattern, comprising: forming a resist film with the resist composition of claim 13; conducting exposure of said resist film; and alkali-developing said resist film to form a resist pattern.

22. A compound represented by general formula (b1-11) shown below:

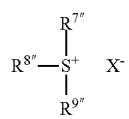
(b1-11)

wherein each of $R^{7\prime\prime}$ to $R^{9\prime\prime}$ independently represents an aryl group or an alkyl group, and two of $R^{7\prime\prime}$ to $R^{9\prime\prime}$ may be bonded to each other to form a ring with the sulfur atom, with the provision that at least one of $R^{7\prime\prime}$ to $R^{9\prime\prime}$ represents a substituted aryl group having a group represented by general formula (I) shown below as a substituent; and X⁻ represents an anion; and

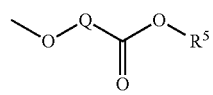
(I)

wherein R⁵ represents an organic group having a sulfonyl group; a linear or branched aliphatic hydrocarbon group having 3 to 15 carbon atoms and an ester bond or a carbonyl group; an aromatic hydrocarbon group having 3 to 30 carbon atoms and an ester bond or a carbonyl group; or a saturated aliphatic cyclic group having 3 to 20 carbon atoms in which hydrogen atoms bonded to a carbon atom of the cyclic group have been replaced by an oxygen atom; and Q represents a divalent linking group.

23. The compound according to claim 22, wherein X⁻ represents an anion selected from the group consisting of a sulfonate anion, an imide anion, a methide anion and a halogen anion.

24. An acid generator comprising the compound of claim 22.

* * * * *